(12) United States Patent
Park et al.

(10) Patent No.: US 9,079,903 B2
(45) Date of Patent: Jul. 14, 2015

(54) HETEROCYCLIC COMPOUND AND ORGANIC LIGHT-EMITTING DEVICE INCLUDING THE SAME

(75) Inventors: Bum-Woo Park, Yongin (KR); Yoon-Hyun Kwak, Yongin (KR); Sun-Young Lee, Yongin (KR); Chang-Ho Lee, Yongin (KR); Se-Jin Cho, Yongin (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 588 days.

(21) Appl. No.: 13/408,596

(22) Filed: Feb. 29, 2012

(65) Prior Publication Data

US 2013/0112946 A1 May 9, 2013

(30) Foreign Application Priority Data

Nov. 3, 2011 (KR) .................. 10-2011-0114115

(51) Int. Cl.
| | |
|---|---|
| *H01L 51/50* | (2006.01) |
| *C07D 471/06* | (2006.01) |
| *C07D 495/06* | (2006.01) |
| *H01L 51/00* | (2006.01) |

(52) U.S. Cl.
CPC ............ *C07D 471/06* (2013.01); *C07D 495/06* (2013.01); *H01L 51/0073* (2013.01); *H01L 51/0074* (2013.01); *H01L 51/5072* (2013.01); *H01L 2251/308* (2013.01)

(58) Field of Classification Search
None
See application file for complete search history.

(56) References Cited

U.S. PATENT DOCUMENTS

| 5,635,308 A | 6/1997 | Inoue et al. |
| 5,645,948 A | 7/1997 | Shi et al. |

(Continued)

FOREIGN PATENT DOCUMENTS

| JP | 08012600 | 1/1996 |
| JP | 2000003782 | 1/2000 |

(Continued)

OTHER PUBLICATIONS

Mikami et al., Asymmetric Catalysis of Homo-Coupling of 3-Substituted Naphthylamine and Hetero-Coupling with 3-Substituted Naphthol Leading to 3,3'-Dimethyl-2,2'-Damonobinaphthyl and -2-amino-2'-hydrobinaphthyl, 2010, Chirality, vol. 22, pp. 224-228).*

(Continued)

*Primary Examiner* — Gregory Clark
(74) *Attorney, Agent, or Firm* — Robert E. Bushnell, Esq.

(57) ABSTRACT

A heterocyclic compound represented by Formula 1 below and an organic light-emitting device including the heterocyclic compound:

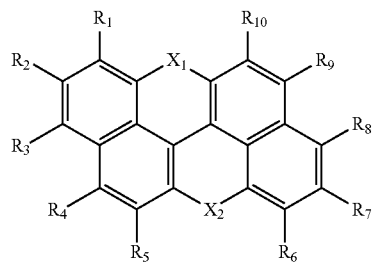

Formula 1 wherein $X_1$ and $X_2$, $X_1$ and $R_1$ to $R_{10}$ are defined as in the specification.

20 Claims, 2 Drawing Sheets

(56) References Cited

U.S. PATENT DOCUMENTS

| | | | |
|---|---|---|---|
| 5,972,247 | A | 10/1999 | Shi et al. |
| 6,465,115 | B2 | 10/2002 | Shi et al. |
| 6,596,415 | B2 | 7/2003 | Shi et al. |
| 7,785,720 | B2 | 8/2010 | Cho et al. |
| 2003/0132703 | A1* | 7/2003 | Sakaguchi ............ 313/504 |
| 2006/0118789 | A1* | 6/2006 | Suh et al. ............ 257/72 |
| 2007/0018569 | A1* | 1/2007 | Kawamura et al. ........ 313/504 |
| 2007/0278938 | A1 | 12/2007 | Yabunouchi et al. |
| 2008/0106190 | A1 | 5/2008 | Yabunouchi et al. |
| 2008/0166594 | A1 | 7/2008 | Ito et al. |
| 2008/0258615 | A1* | 10/2008 | Begley et al. ........... 313/504 |
| 2010/0066241 | A1 | 3/2010 | Cho et al. |
| 2010/0181556 | A1* | 7/2010 | Wang ............ 257/40 |
| 2012/0205629 | A1* | 8/2012 | Wigglesworth et al. ....... 257/40 |

FOREIGN PATENT DOCUMENTS

| | | |
|---|---|---|
| KR | 1020060051621 | 5/2006 |
| KR | 1020060082668 | 7/2006 |
| KR | 1020070101752 | 10/2007 |
| KR | 1020080031872 | 4/2008 |
| KR | 1020080112325 | 12/2008 |
| KR | 1020090040895 | 4/2009 |
| KR | 1020100000772 | 1/2010 |
| KR | 1020100003624 | 1/2010 |

OTHER PUBLICATIONS

Yamaguchi et al., Diphenylamino-Substituted 2,5-Diarylsiloles for Single-Layer Organic Electroluminescent Devices, Chem. Lett. (2001) pp. 98-99.

Sakamoto et al., Synthesis, Characterization, and Electron-Transport Property of Perfluorinated Phenylene Dendrimers, J. Am. Chem. Soc. (2000) 122, pp. 1832-1833.

Adachi et al., Confinement of charge carriers and molecular excitons within 5-nm-thick emitter layer in organic electroluminescent devices with a double heterostructure, Appl. Phys. Lett. (1990) 57, pp. 531-533.

Tang et al., Organic electroluminescent diodes, Appl. Phys. Lett. (1987) 51, pp. 913-915.

* cited by examiner

HETEROCYCLIC COMPOUND AND ORGANIC LIGHT-EMITTING DEVICE INCLUDING THE SAME

CLAIM OF PRIORITY

This application claims the benefit of Korean Patent Application No. 10-2011-0114115, filed on 3 Nov. 2011 in the Korean Intellectual Property Office, the disclosure of which is incorporated herein in its entirety by reference.

BACKGROUND OF THE INVENTION

1. Field of the Invention

The present invention relates to a heterocyclic compound represented by Formula 1 and an organic light-emitting device including the heterocyclic compound.

2. Description of the Related Art

Light-emitting devices are self-emission type display devices and have a wide viewing angle, a high contrast ratio, and a short response time. Due to these characteristics, light-emitting devices are drawing more attention. Such light-emitting devices can be roughly classified into inorganic light-emitting devices that include emission layers containing inorganic compounds, and organic light-emitting devices that include emission layers containing organic compounds. Specifically, organic light-emitting devices have higher luminance, lower driving voltages, and shorter response times than inorganic light-emitting devices, and can render multi-colored displays. Thus, much research into such organic light-emitting devices has been conducted. Typically, an organic light-emitting device has a stack structure including an anode, a cathode and an organic emission layer interposed therebetween. However, a hole injection layer and/or a hole transport layer may be further stacked between the anode and the organic emission layer, and/or an electron transport layer may be further stacked between the organic emission layer and the cathode. In other words, an organic light-emitting device may have a stack structure of anode/hole transport layer/organic emission layer/cathode or a stack structure of anode/hole transport layer/organic emission layer/electron transport layer/cathode.

As a material for forming the organic emission layer, naphthalene derivatives can be used. However, organic light-emitting devices including such materials may not have satisfactory life span, efficiency, and power consumption characteristics, thereby improvement in this regard still being necessary.

SUMMARY OF THE INVENTION

The present invention provides a novel heterocyclic compound having improved electrical characteristics, charge transporting capabilities and light-emission capabilities.

The present invention provides an organic light-emitting device including the heterocyclic compound.

The present invention provides a flat panel display device including the organic light-emitting device.

According to an aspect of the present invention, there is provided a compound represented by Formula 1 below:

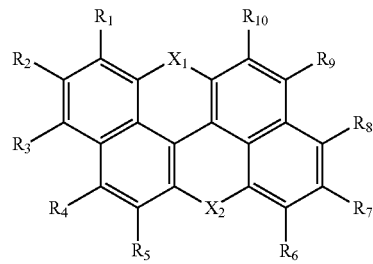

Formula 1 wherein, in Formula 1, $R_1$ to $R_{10}$ are each independently a hydrogen atom, a deuterium atom, a halogen group, a cyano group, a substituted or unsubstituted $C_1$-$C_{60}$ alkyl group, a substituted or unsubstituted alkenyl group, a substituted or unsubstituted $C_5$-$C_{60}$ aryl group, an amino group substituted with a substituted or unsubstituted $C_5$-$C_{60}$ aryl group, a substituted or unsubstituted $C_3$-$C_{60}$ heteroaryl group, or a substituted or unsubstituted $C_6$-$C_{60}$ condensed polycyclic group;

$X_1$ and $X_2$ are each independently —N($R_{20}$)— or —S—;

adjacent substituents among $R_1$ to $R_5$ or those among $R_6$ to $R_{10}$ are optionally linked to form a ring; and $R_{20}$ is a hydrogen atom, a deuterium atom, a halogen group, a cyano group, a substituted or unsubstituted $C_1$-$C_{60}$ alkyl group, a substituted or unsubstituted $C_1$-$C_{50}$ alkenyl group, a substituted or unsubstituted $C_5$-$C_{60}$ aryl group, an amino group substituted with a substituted or unsubstituted $C_5$-$C_{60}$ aryl group, a substituted or unsubstituted $C_3$-$C_{60}$ heteroaryl group, or a substituted or unsubstituted $C_6$-$C_{60}$ condensed polycyclic group.

In Formula 1, $R_1$ to $R_{10}$ and $R_{20}$ may be each independently a hydrogen atom, a deuterium atom, a halogen group, a cyano group, a substituted or unsubstituted $C_1$-$C_{20}$ alkyl group, a substituted or unsubstituted alkenyl group, a substituted or unsubstituted $C_5$-$C_{30}$ aryl group, an amino group substituted with a substituted or unsubstituted $C_5$-$C_{30}$ aryl group, a substituted or unsubstituted $C_5$-$C_{30}$ heteroaryl group, or a substituted or unsubstituted $C_6$-$C_{30}$ condensed polycyclic group.

In Formula 1, $R_1$ to $R_{10}$ and $R_{20}$ may be each independently selected from the group consisting of a hydrogen atom, a deuterium atom, a halogen atom, a cyano group, a substituted or unsubstituted $C_1$-$C_{20}$ alkyl group, a substituted or unsubstituted $C_1$-$C_{20}$ alkenyl group, and groups represented by Formulae 2a to 2j below:

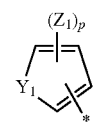

2a

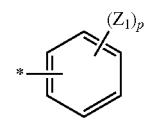

2b

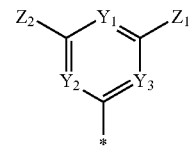

2c

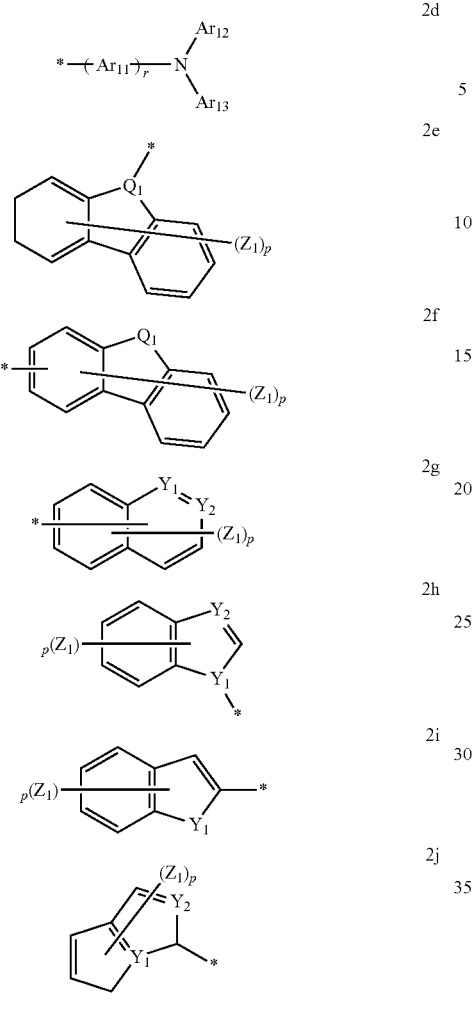

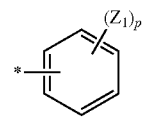
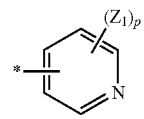
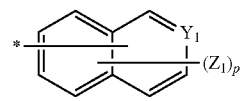
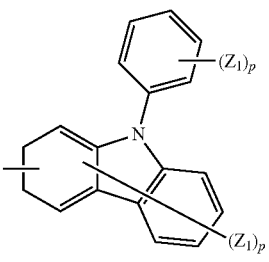
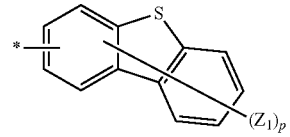
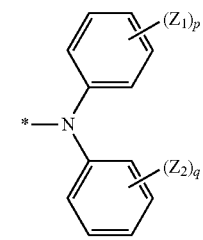
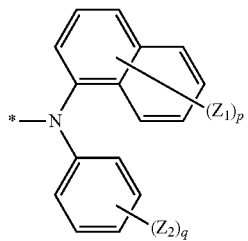
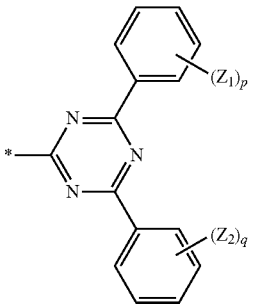

wherein, in Formulae 2a to 2j, $Q_1$ may be represented by —C($R_{30}$)($R_{31}$)—, —N($R_{32}$)—, —N(-*)-, —S—, or —O—;

$Y_1$, $Y_2$, and $Y_3$ may be each independently represented by —N═, —N(-*)-, —S—, —O—, —C($R_{33}$)═, or —C(-*)═.

$Z_1$, $Z_2$, $Ar_{12}$, $Ar_{13}$, $R_{30}$, $R_{31}$, $R_{32}$, and $R_{33}$ may be each independently selected from the group consisting of a lone pair electron, a hydrogen atom, a deuterium atom, a halogen group, a cyano group, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a nitro group, a hydroxyl group, and a carboxy group;

$Ar_{11}$ may be selected from the group consisting of a substituted or unsubstituted $C_1$-$C_{20}$ alkylene group, a substituted or unsubstituted $C_5$-$C_{20}$ arylene group, and a substituted or unsubstituted $C_3$-$C_{20}$ heteroarylene group;

p may be an integer from 1 to 10;

r may be an integer from 0 to 5; and

* indicates a binding site.

In Formula 1, $R_1$ to $R_{10}$ and $R_{20}$ may be each independently selected from the group consisting of a hydrogen atom, a deuterium atom, a halogen group, a cyano group, a substituted or unsubstituted $C_1$-$C_{20}$ alkyl group, a substituted or unsubstituted alkenyl group, and groups represented by Formulae 3a to 3h below:

wherein, in Formulae 3a to 3h, $Y_1$ may be represented by —N═, —S—, —O—, or —C($R_{34}$)—;

$Z_1$ and $Z_2$ may be each independently selected from the group consisting of a hydrogen atom, a deuterium atom, a halogen group, a cyano group, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a nitro group, a hydroxyl group, and a carboxy group;

p and q may be each independently an integer from 1 to 7; and

* indicates a binding site.

The compound represented by Formula 1 may be symmetrical.

In Formula 1, $R_1$ to $R_{10}$ and $R_{20}$ may be each independently selected from the group consisting of a hydrogen atom, a deuterium atom, a halogen group, a cyano group, a substituted or unsubstituted $C_1$-$C_{20}$ alkyl group, a substituted or unsubstituted $C_1$-$C_{20}$ alkenyl group, and groups represented by Formulae 2a to 2j below; and the compound represented by Formula 1 may be symmetrical:

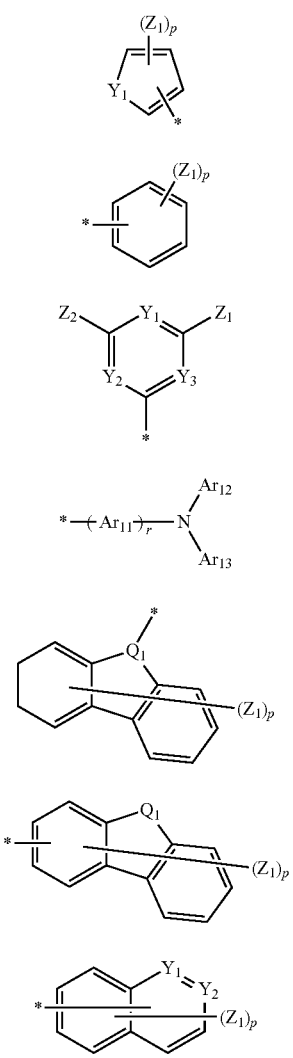

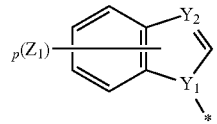

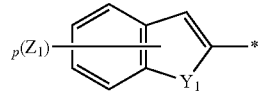

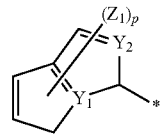

wherein, in Formulae 2a to 2j, $Q_1$ may be represented by —$C(R_{30})(R_{31})$—, —$N(R_{32})$—, —$N(-*)$-, —S—, or —O—;

$Y_1$, $Y_2$, and $Y_3$ may be each independently represented by —N=, —N(-*)-, —S—, —O—, —$C(R_{33})$=, or —$C(-*)$=;

$Z_1$, $Z_2$, $Ar_{12}$, $Ar_{13}$, $R_{30}$, $R_{31}$, $R_{32}$, and $R_{33}$ may be each independently selected from the group consisting of a lone pair electron, a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, and a carboxy group;

$Ar_{11}$ may be selected from the group consisting of a substituted or unsubstituted $C_1$-$C_{20}$ alkylene group, a substituted or unsubstituted $C_5$-$C_{20}$ arylene group, and a substituted or unsubstituted heteroarylene group;

p may be an integer from 1 to 10;

r may be an integer from 0 to 5; and

* indicates a binding site.

The compound of Formula 1 may be one of the compounds below:

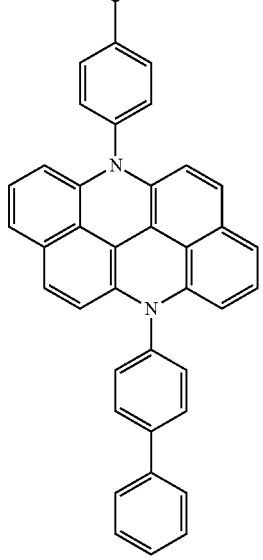

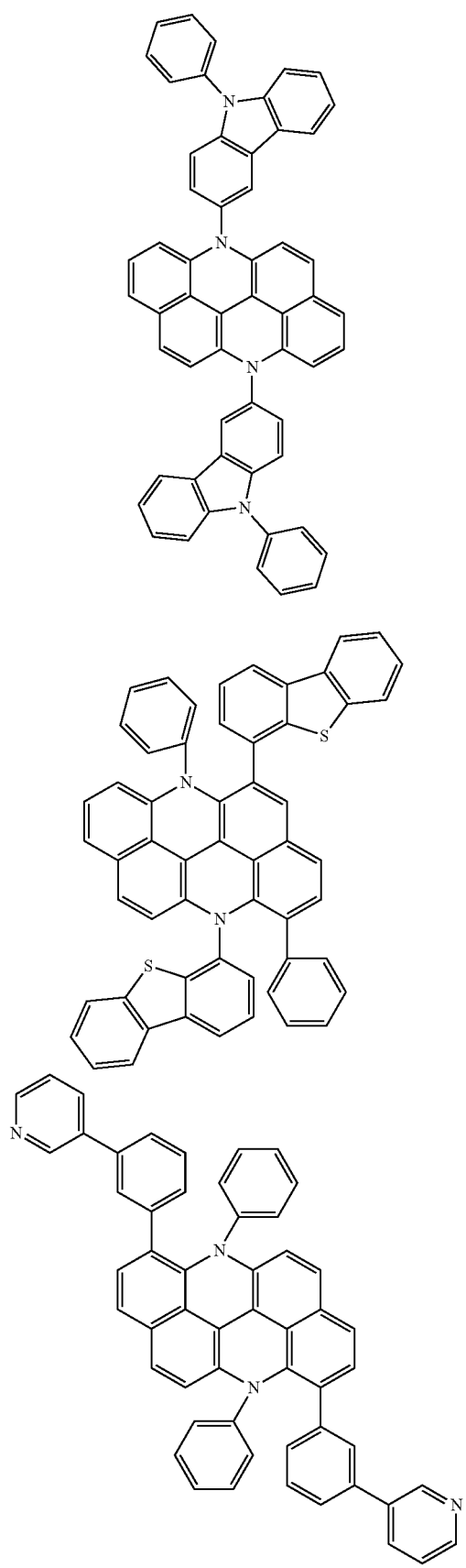
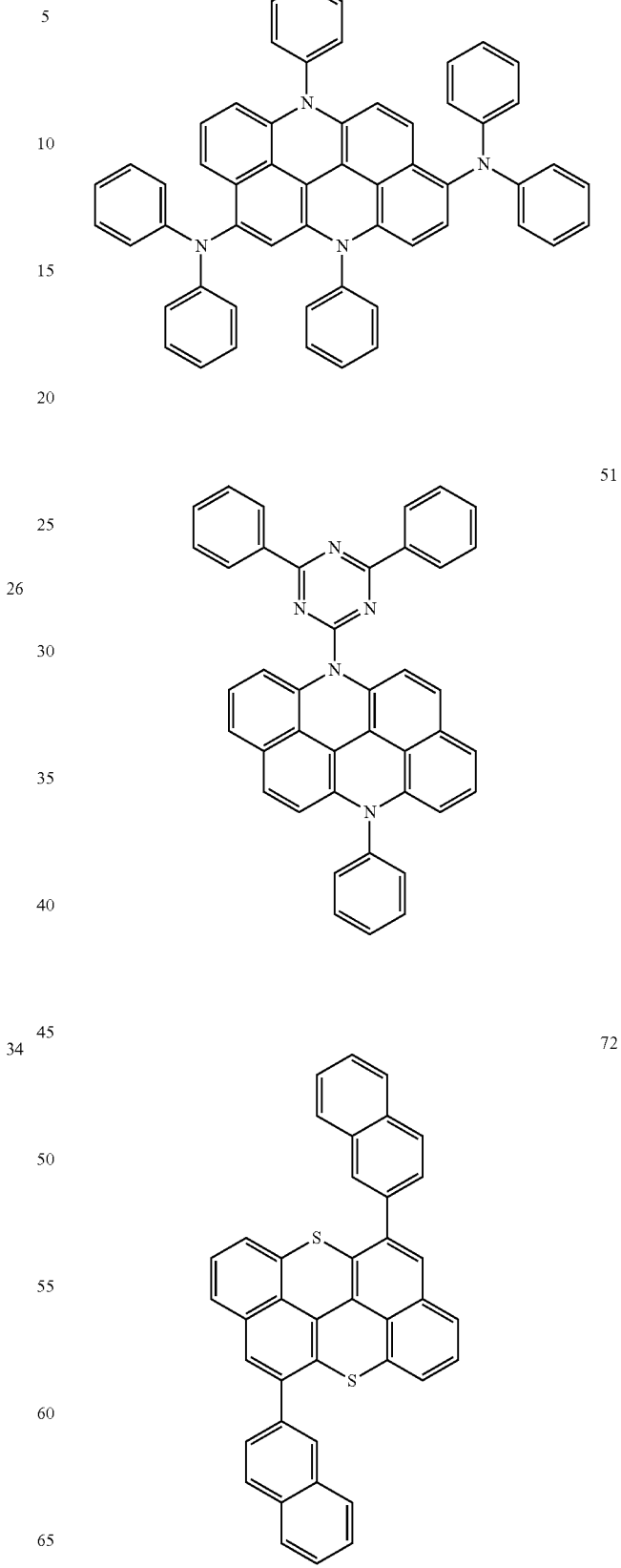

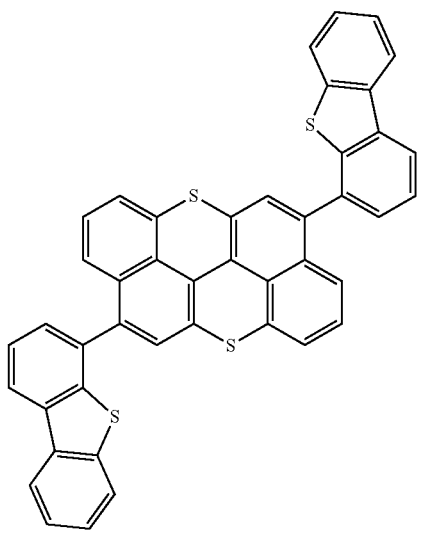

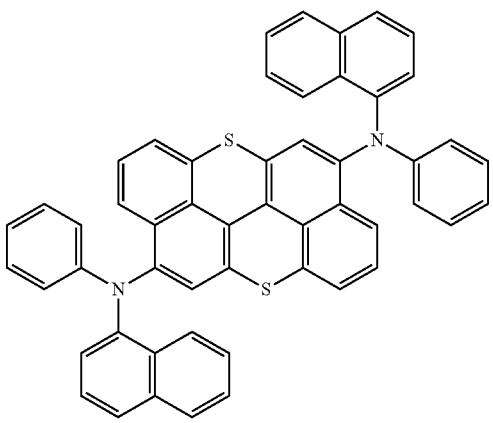

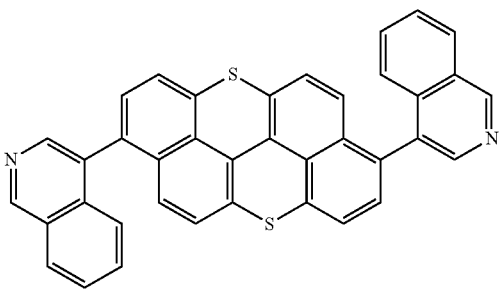

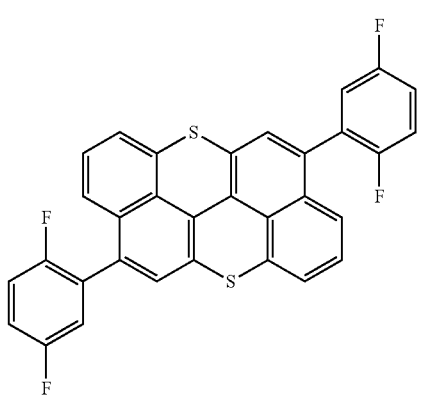

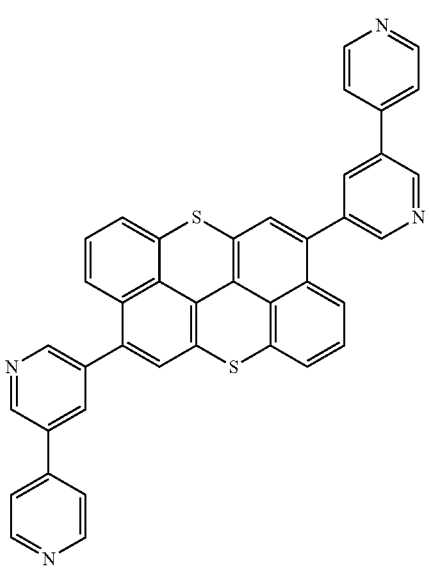

According to another aspect of the present invention, there is provided an organic light-emitting device including: a first electrode; a second electrode; and an organic layer between the first electrode and the second electrode, wherein the organic layer includes a first layer including the compound of Formula 1 above.

The first layer may include at least one layer selected from the group consisting of a hole injection layer, a hole transport layer, a functional layer having both hole injection and hole transport capabilities, an electron injection layer, an electron transport layer, and a functional layer having both electron injection and electron transport capabilities.

The organic layer may be an emission layer comprising the compound of Formula 1 as a host for a fluorescence or phosphorescence device.

The organic layer may include an emission layer, a hole transport layer, and an electron transport layer; and the first layer may be an emission layer that further includes an anthracene compound, an arylamine compound, or a styryl compound.

The organic layer may include an emission layer, a hole transport layer, and an electron transport layer; and the first layer may be an emission layer of which a red layer, a green layer, a blue layer, or a white layer further includes a phosphorescent compound.

The first layer may be a blue emission layer.

The first layer may be a blue emission layer, and the compound of Formula 1 may be used as a blue host.

The organic layer may further include a hole injection layer, a hole transport layer, a functional layer having both hole injection and hole transport capabilities, an emission layer, a hole blocking layer, an electron transport layer, an electron injection layer, or a combination of at least two thereof.

At least one of the hole injection layer, the hole transport layer, and the functional layer having hole injection and hole transport capabilities may further include a charge generating material.

The electron transport layer may include an electron transporting organic material and a metal-containing material.

The metal-containing material may include a lithium (Li) complex.

The first layer may be formed from the compound of Formula 1 of claim 1 using a wet process.

According to another aspect of the present invention, there is provided a flat panel display device including the organic light-emitting device described above, wherein the first electrode of the organic light-emitting device is electrically connected to a source electrode or a drain electrode of a thin-film transistor.

BRIEF DESCRIPTION OF THE DRAWINGS

The above and other features and advantages of the present invention will become more apparent by describing in detail exemplary embodiments thereof with reference to the attached drawing in which.

DETAILED DESCRIPTION OF THE INVENTION

Figure 1:
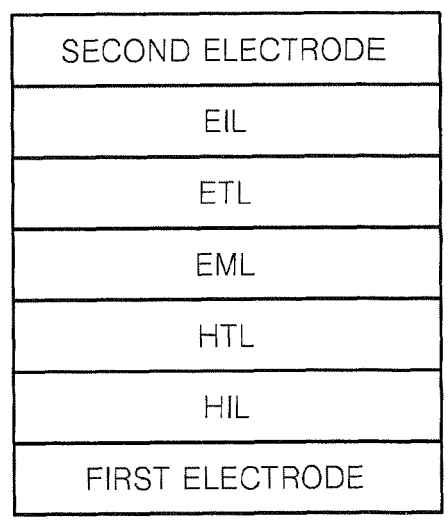
FIG. 1 illustrates the structure of an organic light-emitting device according to an embodiment of the present invention.

As used herein, the term "and/or" includes any and all combinations of one or more of the associated listed items. Expressions such as "at least one of," when preceding a list of elements, modify the entire list of elements and do not modify the individual elements of the list.

Anthracene derivatives are widely known as materials for an organic emission layer. Alq3, PBD, PF-6P, PyPySPyPy, and the like are known as electron transport materials. For example, an organic light-emitting device manufactured using a compound of phenylanthracene dimer or trimer is widely known. However, such organic light-emitting devices have a narrow energy gap and lower blue-light color purity since two or three oligomeric species of anthracene are linked by conjugation.

In addition, such compounds are highly vulnerable to oxidation and thus are liable to produce impurities, necessitating purification. In order to overcome these drawbacks, organic light-emitting devices manufactured using an anthracene compound including naphthalene substituted for anthracene at 1,9 positions or using a diphenylanthracene compound including an aryl group substituted for a phenyl group at m-position have been introduced. However, these organic light-emitting devices have a lower light-emission efficiency.

Organic light-emitting devices may also be manufactured using nathphalene-substituted monoanthracene derivatives. However, the light-emission efficiency thereof is low at about 1 cd/A, and thus such organic light-emitting devices are not suitable for practical use. Furthermore, organic light-emitting devices may be manufactured using phenylanthracene compounds including aryl substituents at m-position. Such a compound has excellent thermal resistance but leads to an unsatisfactorily low light-emission efficiency of about 2 cd/A.

The present invention will now be described more fully with reference to the accompanying drawings, in which exemplary embodiments of the invention are shown.

An aspect of the present invention provides a heterocyclic compound represented by Formula 1 below.

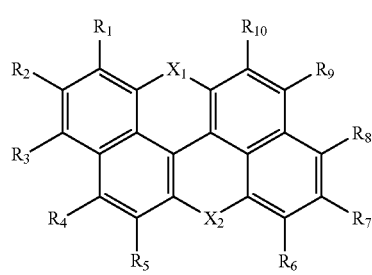

Formula 1

In Formula 1 above, $R_1$ to $R_{10}$ may be each independently a hydrogen atom, a deuterium atom, a halogen group, a cyano group, a substituted or unsubstituted $C_1$-$C_{60}$ alkyl group, a substituted or unsubstituted $C_1$-$C_{50}$ alkenyl group, a substituted or unsubstituted $C_5$-$C_{60}$ aryl group, an amino group substituted with a substituted or unsubstituted $C_5$-$C_{60}$ aryl group, a substituted or unsubstituted $C_3$-$C_{60}$ heteroaryl group, or a substituted or unsubstituted $C_6$-$C_{60}$ condensed polycyclic group: and $X_1$ and $X_2$ may be each independently —N($R_{20}$)— or —S—.

Optionally, adjacent substituents among $R_1$ to $R_5$ or those among $R_6$ to $R_{10}$ may be linked to form a ring.

$R_{20}$ is a hydrogen atom, a deuterium atom, a halogen group, a cyano group, a substituted or unsubstituted $C_1$-$C_{60}$ alkyl group, a substituted or unsubstituted $C_1$-$C_{50}$ alkenyl group, a substituted or unsubstituted $C_5$-$C_{60}$ aryl group, an amino group substituted with a substituted or unsubstituted $C_5$-$C_{60}$ aryl group, a substituted or unsubstituted $C_3$-$C_{60}$ heteroaryl group, or a substituted or unsubstituted $C_6$-$C_{60}$ condensed polycyclic group.

In some embodiments the heterocyclic compound of Formula 1 may be used as a light-emitting material, an electron-transporting material or an electron-injecting material.

An organic light-emitting device manufactured using the heterocyclic compound of Formula 1 above may have high durability when stored or operated.

Substituents in the heterocyclic compound of Formula 1 will now be described in detail.

In some embodiments, in Formula 1, $R_1$ to $R_{10}$ and $R_{20}$ may be each independently a hydrogen atom, a deuterium atom, a halogen group, a cyano group, a substituted or unsubstituted $C_1$-$C_{20}$ alkyl group, a substituted or unsubstituted $C_1$-$C_{20}$ alkenyl group, a substituted or unsubstituted $C_5$-$C_{30}$ aryl group, an amino group substituted with a substituted or unsubstituted $C_5$-$C_{30}$ aryl group, a substituted or unsubstituted $C_5$-$C_{30}$ heteroaryl group, or a substituted or unsubstituted $C_6$-$C_{30}$ condensed polycyclic group.

In some embodiments, in Formula 1, $R_1$ to $R_{10}$ and $R_{20}$ may be each independently selected from the group consisting of a hydrogen atom, a deuterium atom, a halogen atom, a cyano group, a substituted or unsubstituted $C_1$-$C_{20}$ alkyl group, a substituted or unsubstituted $C_1$-$C_{20}$ alkenyl group, and groups represented by Formulae 2a to 2j below:

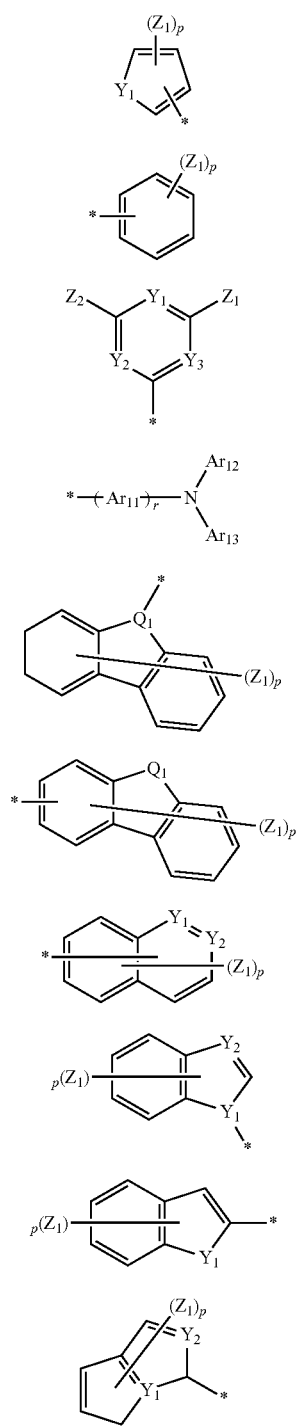

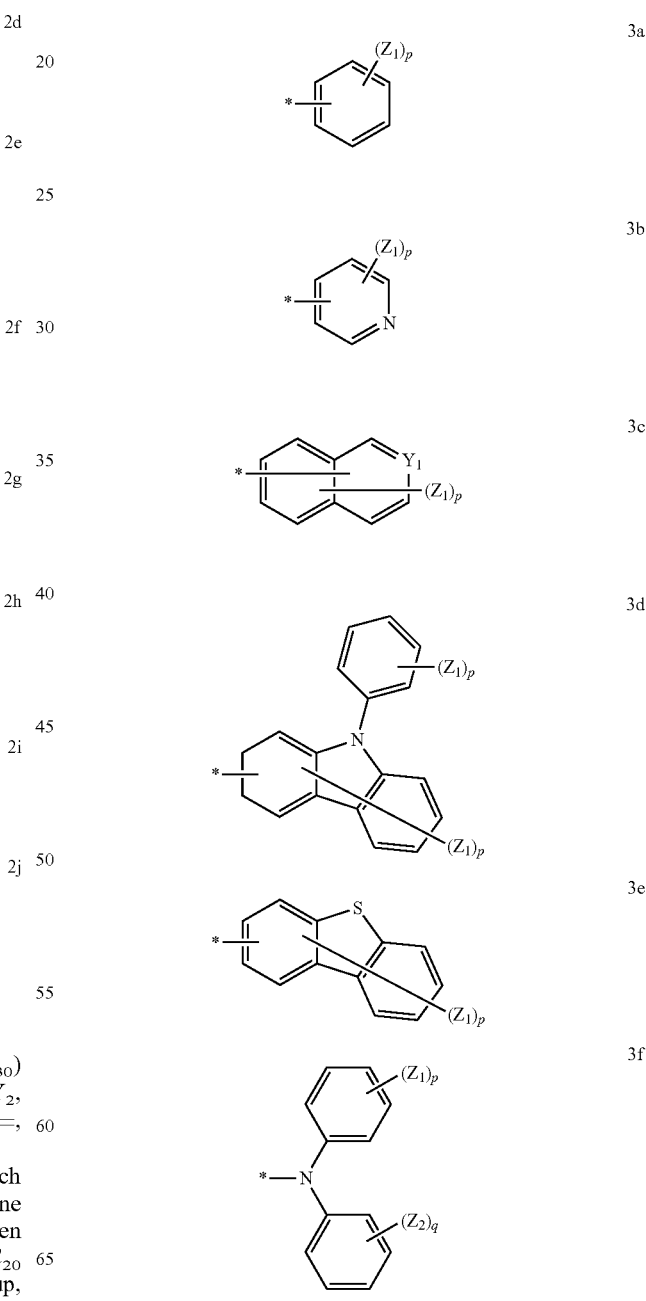

In Formulae 2a to 2j, $Q_1$ may be represented by —C($R_{30}$)($R_{31}$)—, —N($R_{32}$)—, —N(-*)-, —S—, or —O—; $Y_1$, $Y_2$, and $Y_3$ may be each independently represented by —N═, —N(-*)-, —S—, —O—, —C($R_{33}$)═, or —C(-*)═;

$Z_1$, $Z_2$, $Ar_{12}$, $Ar_{13}$, $R_{30}$, $R_{31}$, $R_{32}$, and $R_{33}$ may be each independently selected from the group consisting of a lone pair electron, a hydrogen atom, a deuterium atom, a halogen group, a cyano group, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a nitro group, a hydroxyl group, and a carboxy group;

$Ar_{11}$ may be selected from the group consisting of a substituted or unsubstituted $C_1$-$C_{20}$ alkylene group, a substituted or unsubstituted $C_5$-$C_{20}$ arylene group, and a substituted or unsubstituted $C_3$-$C_{20}$ heteroarylene group:

p may be an integer from 1 to 10; r is an integer from 0 to 5; and * indicates a binding site.

In some embodiments, in Formula 1, $R_1$ to $R_{10}$ and $R_{20}$ may be each independently selected from the group consisting of a hydrogen atom, a deuterium atom, a halogen group, a cyano group, a substituted or unsubstituted $C_1$-$C_{20}$ alkyl group, a substituted or unsubstituted $C_1$-$C_{20}$ alkenyl group, and groups represented by Formulae 3a to 3h below:

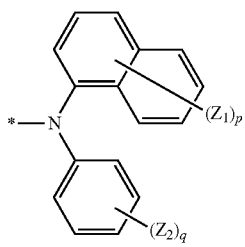

3g

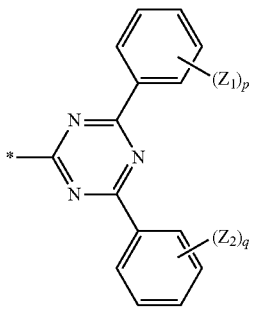

3h

In Formulae 3a to 3h, $Y_1$ may be represented by —N═, —S—, —O—, or —C($R_{34}$)═;

$Z_1$ and $Z_2$ may be each independently selected from the group consisting of a hydrogen atom, a deuterium atom, a halogen group, a cyano group, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a nitro group, a hydroxyl group, and a carboxy group;

p and q may be each independently an integer from 1 to 7; and

* indicates a binding site.

In an embodiment of the present invention, the heterocyclic compound of Formula 1 may be symmetrical. The term "symmetrical" generally means that the compound has one or more planes of symmetry.

In some embodiments, in Formula 1, $R_1$ to $R_{10}$ and $R_{20}$ may be each independently selected from the group consisting of a hydrogen atom, a deuterium atom, a halogen group, a cyano group, a substituted or unsubstituted $C_1$-$C_{20}$ alkyl group, a substituted or unsubstituted $C_1$-$C_{20}$ alkenyl group, and groups represented by Formulae 2a to 2j below and the heterocyclic compound of the Formula 1 may be symmetrical.

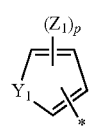

2a

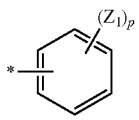

2b

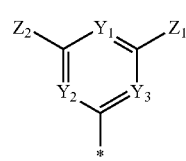

2c

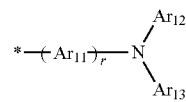

2d

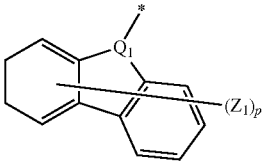

2e

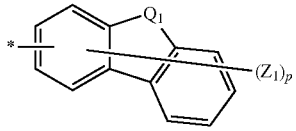

2f

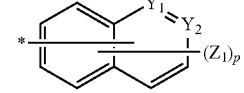

2g

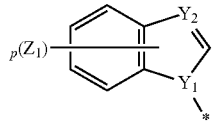

2h

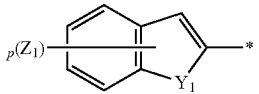

2i

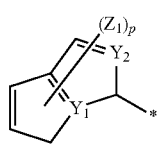

2j

In Formulae 2a to 2j, $Q_1$ may be represented by —C($R_{30}$)($R_{31}$)—, —N($R_{32}$)—, —S—, or —O—;

$Y_1$, $Y_2$, and $Y_3$ may be each independently represented by —N═, —N(-*)-, —S—, —O—, —C($R_{33}$)═, or —C(-*)═;

$Z_1$, $Z_2$, $Ar_{12}$, $Ar_{13}$, $R_{30}$, $R_{31}$, $R_{32}$, and $R_{33}$ may be each independently selected from the group consisting of a lone pair electron, a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, and a carboxy group;

$Ar_{11}$ may be selected from the group consisting of a substituted or unsubstituted $C_1$-$C_{20}$ alkylene group, a substituted or unsubstituted $C_5$-$C_{20}$ arylene group, and a substituted or unsubstituted $C_3$-$C_{20}$ heteroarylene group:

p may be an integer from 1 to 10;

r may be an integer from 0 to 5; and

* indicates a binding site.

Hereinafter, substituents described with reference to the above formulae will now be described in detail. In this regard, the numbers of carbons in substituents are presented only for illustrative purposes and do not limit the characteristics of the substituents.

The unsubstituted $C_1$-$C_{60}$ alkyl group used herein may be linear or branched. Examples of the alkyl group include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_2$-$C_{60}$ alkenyl group indicates an unsaturated alkyl groups having at least one carbon-carbon double bond in the center or at a terminal of the alkyl group. Examples of the alkenyl group include an ethenyl group, a propenyl group, a butenyl group, and the like. At least one hydrogen atom in the unsubstituted alkenyl group may be substituted with a substituent described above in conjunction with the alkyl group.

The unsubstituted $C_2$-$C_{60}$ alkynyl group indicates an alkyl group having at least one carbon-carbon triple bond in the center or at a terminal of the alkyl group. Examples of the unsubstituted alkynyl group include acetylene, propylene, phenylacetylene, naphthylacetylene, isopropylacetylene, t-butylacetylene, diphenylacetylene, and the like. At least one hydrogen atom in the alkynyl group may be substituted with a substituent described above in conjunction with the alkyl group.

The unsubstituted $C_3$-$C_{60}$ cycloalkyl group indicates a $C_3$-$C_{60}$ cyclic alkyl group wherein at least one hydrogen atom in the cycloalkyl group may be substituted with a substituent described above in conduction with the $C_1$-$C_{60}$ alkyl group.

The unsubstituted $C_1$-$C_{60}$ alkoxy group indicates a group having a structure of —OA wherein A is an unsubstituted $C_1$-$C_{60}$ alkyl group as described above. Nonlimiting examples of the unsubstituted $C_1$-$C_{60}$ alkoxy group include a methoxy group, an ethoxy group, a propoxy group, an isopropyloxy group, a butoxy group, and a pentoxy group. At least one hydrogen atom of the alkoxy group may be substituted with a substituent such as those described above in conjunction with the alkyl group.

The unsubstituted $C_5$-$C_{60}$ aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with a substituent described above in conjunction with the unsubstituted $C_1$-$C_{60}$ alkyl group.

Examples of the substituted or unsubstituted $C_5$-$C_{60}$ aryl group include, but are not limited to, a phenyl group, a $C_1$-$C_{10}$ alkylphenyl group (for example, ethylphenyl group), a halophenyl group (for example, o-, m-, and p-fluorophenyl group, dichlorophenyl group), a cyanophenyl group, dicyanophenyl group, a trifluoromethoxyphenyl group, a biphenyl group, a halobiphenyl group, a cyanobiphenyl group, a $C_1$-$C_{10}$ alkyl biphenyl group, a $C_1$-$C_{10}$ alkoxybiphenyl group, a o-, m-, and p-toryl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, fluoronaphthyl group), a $C_1$-$C_{10}$ alkylnaphthyl group (for example, methylnaphthyl group), a $C_1$-$C_{10}$ alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted $C_3$-$C_{60}$ heteroaryl group used herein includes one, two or three hetero atoms selected from N, O, P and S. At least two rings may be fused to each other or linked to each other by a single bond. Examples of the unsubstituted $C_4$-$C_{60}$ heteroaryl group include a pyrazolyl group, an imidazolyl group, an oxazolyl group, a thiazolyl, group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the heteroaryl group may be substituted with a substituent described above in conjunction with the unsubstituted $C_1$-$C_{60}$ alkyl group.

The unsubstituted $C_5$-$C_{60}$ aryloxy group is a group represented by —$OA_1$ wherein $A_1$ may be a $C_5$-$C_{60}$ aryl group. An example of the aryloxy group is a phenoxy group. At least one hydrogen atom in the aryloxy group may be substituted with a substituent described above in conjunction with the unsubstituted $C_1$-$C_{60}$ alkyl group.

The unsubstituted $C_5$-$C_{60}$ arylthio group is represented by —$SA_1$, wherein $A_1$ may be a $C_5$-$C_{60}$ aryl group. Nonlimiting examples of the arylthio group include a benzenethio group and a naphthylthio group. At least one hydrogen atom in the arylthio group may be substituted with a substituent described above in conjunction with the unsubstituted $C_1$-$C_{60}$ alkyl group.

The unsubstituted $C_6$-$C_{60}$ condensed polycyclic group used herein refers to a substituent including at least two rings wherein at least one aromatic ring and/or at least one non-aromatic ring are fused to each other, and is distinct from an aryl group or a heteroaryl group in terms of being non-aromatic.

Examples of the heterocyclic compound represented by Formula 1 are Compounds 1 to 126 represented by the following formulae. However, the heterocyclic compound of Formula 1 is not be limited to those compounds.

The followings are representative synthetic routes of the heterocyclic compound of Formula 1. Detailed synthetic processes will be described later in synthesis examples.

representative synthetic route 1
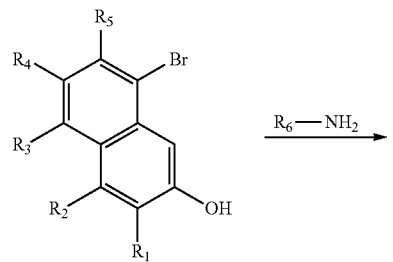
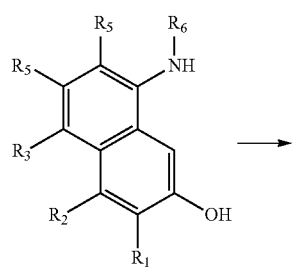
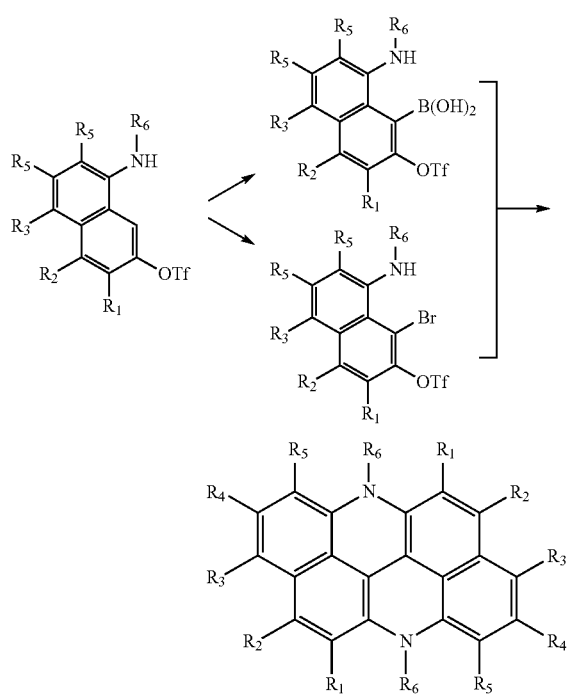
representative synthetic route 2
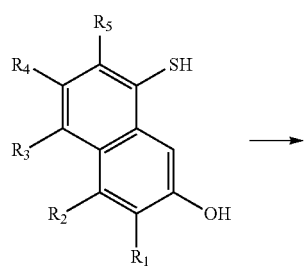
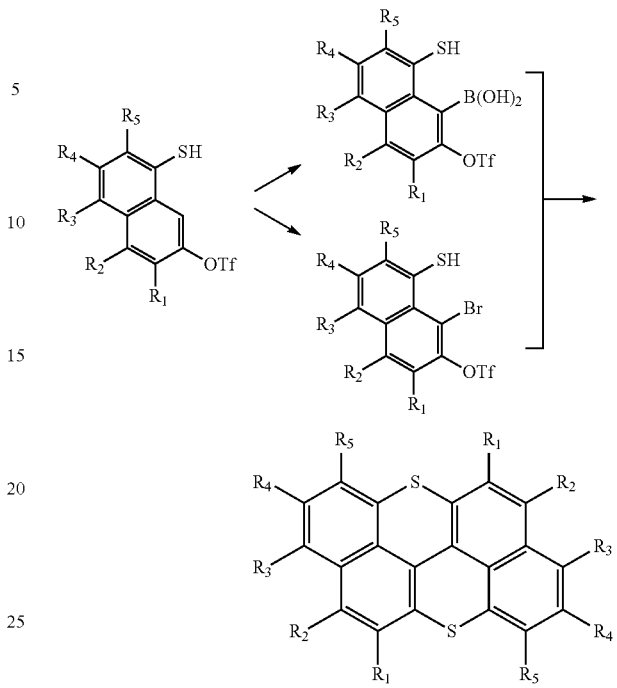
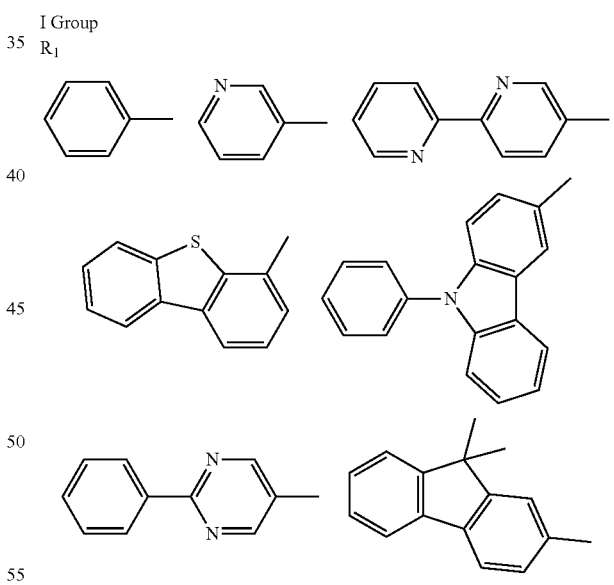
Examples of substituents in the synthetic routes are represented by the following formulae.
I Group
R₁
II Group
R₂
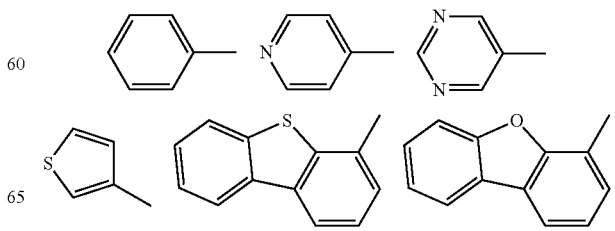

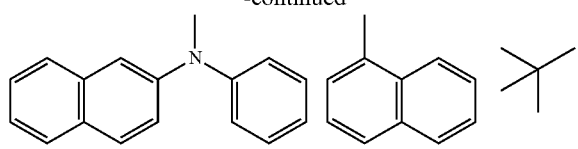
III Group
$R_3$
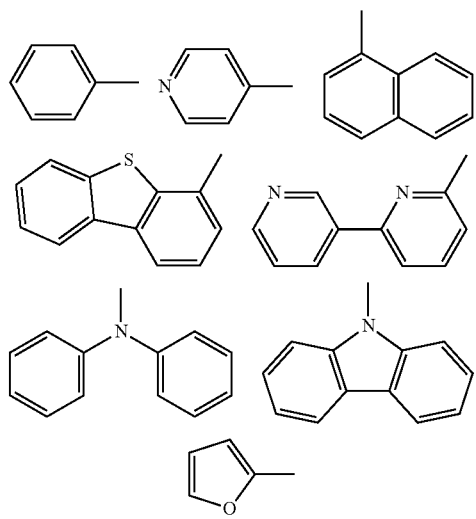
IV Group
$R_4$
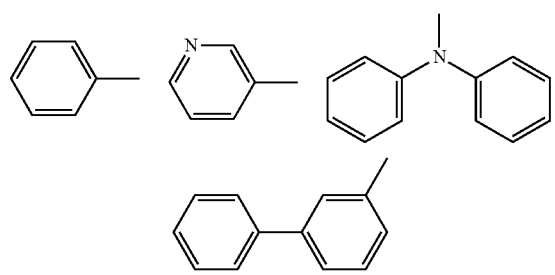
V Group
$R_5$
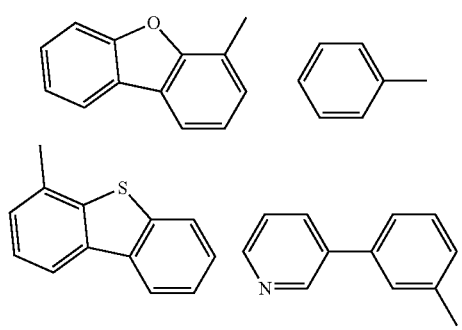
VI Group
$R_6$—$NH_2$
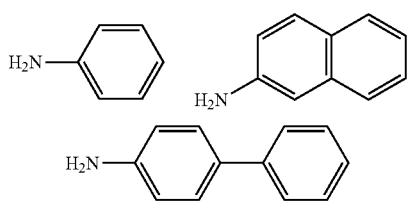
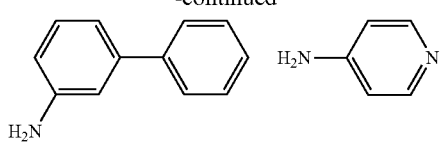
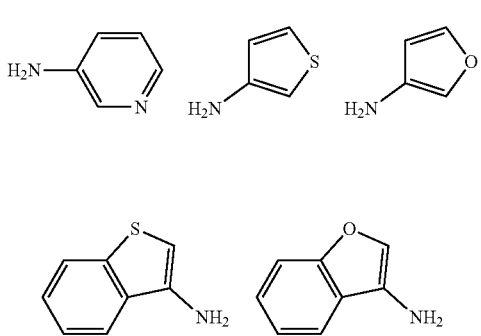
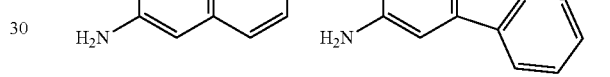
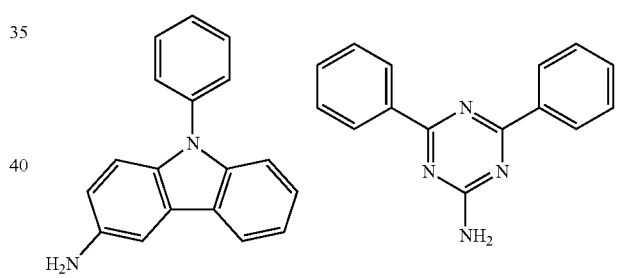
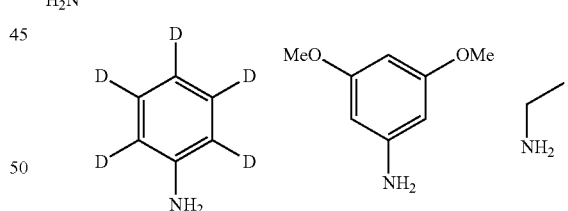
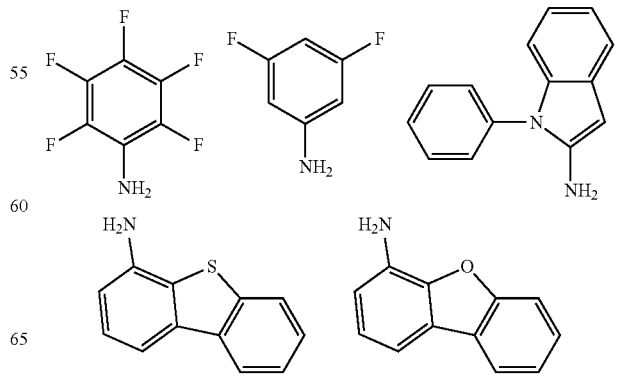

1
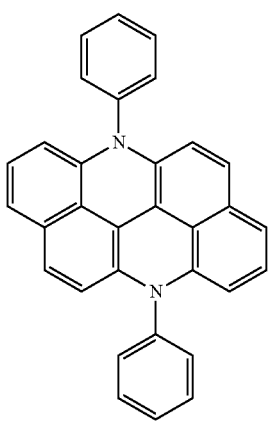
2
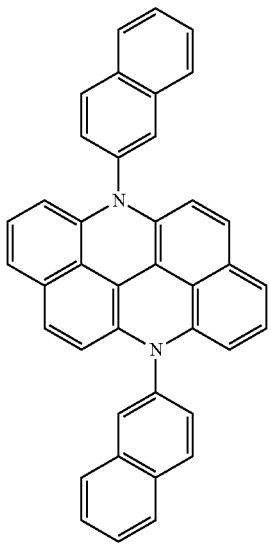
3
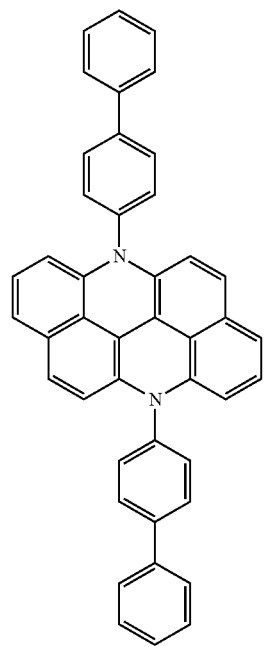
4
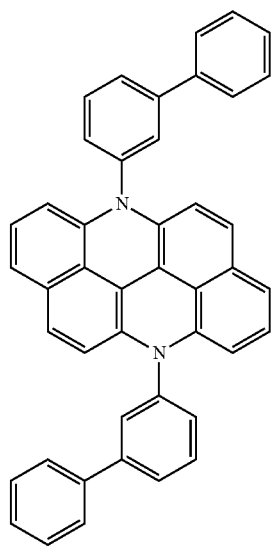
5
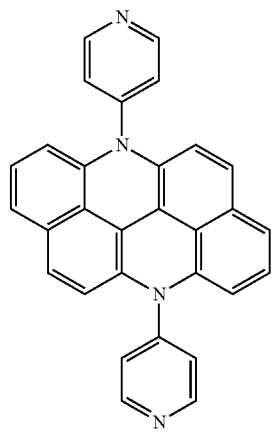
6

7
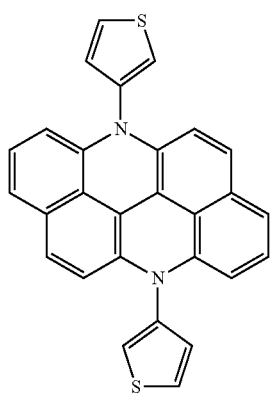
8
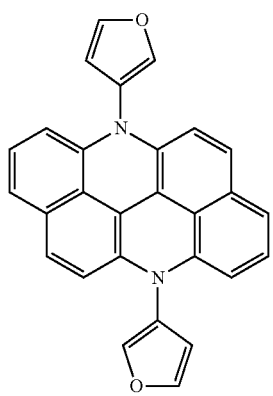
9
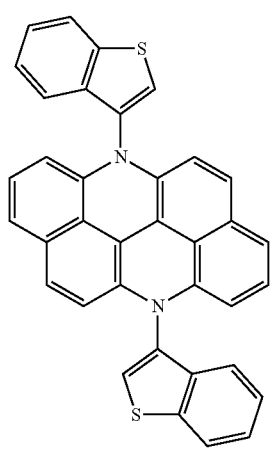
10
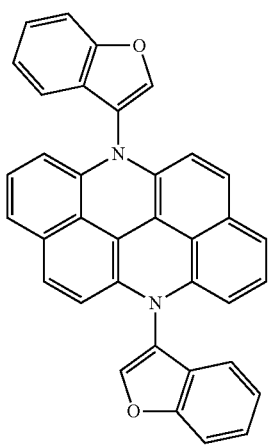
11
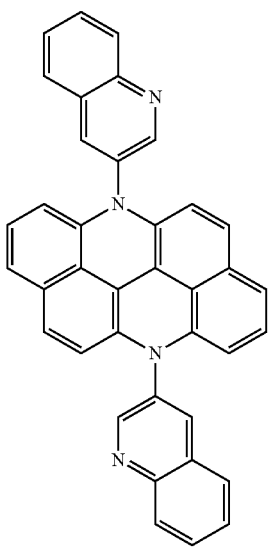
12
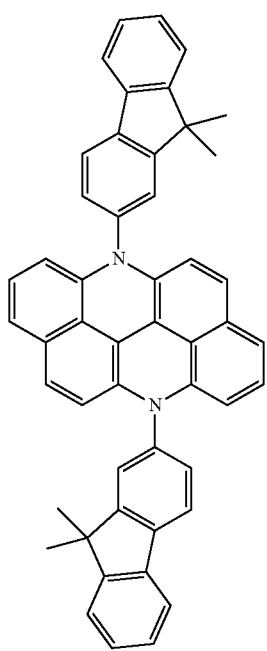

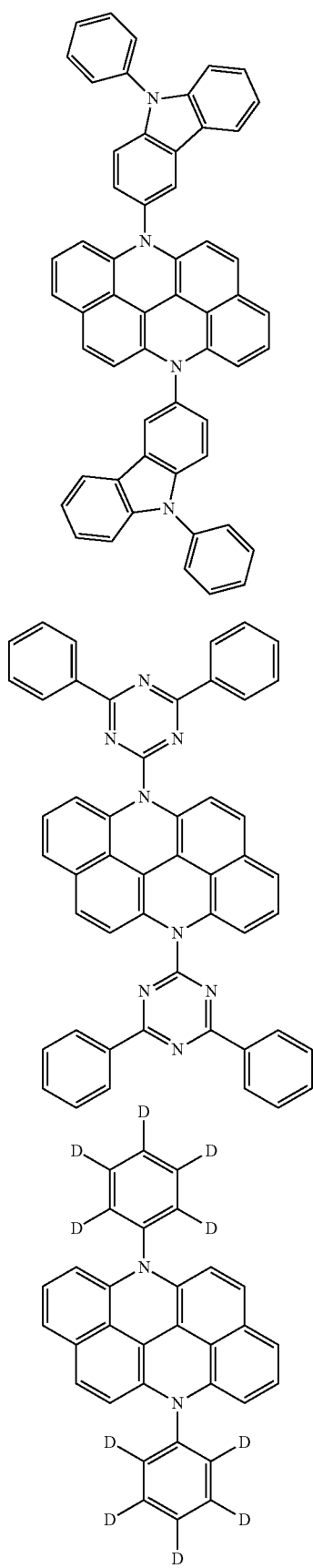
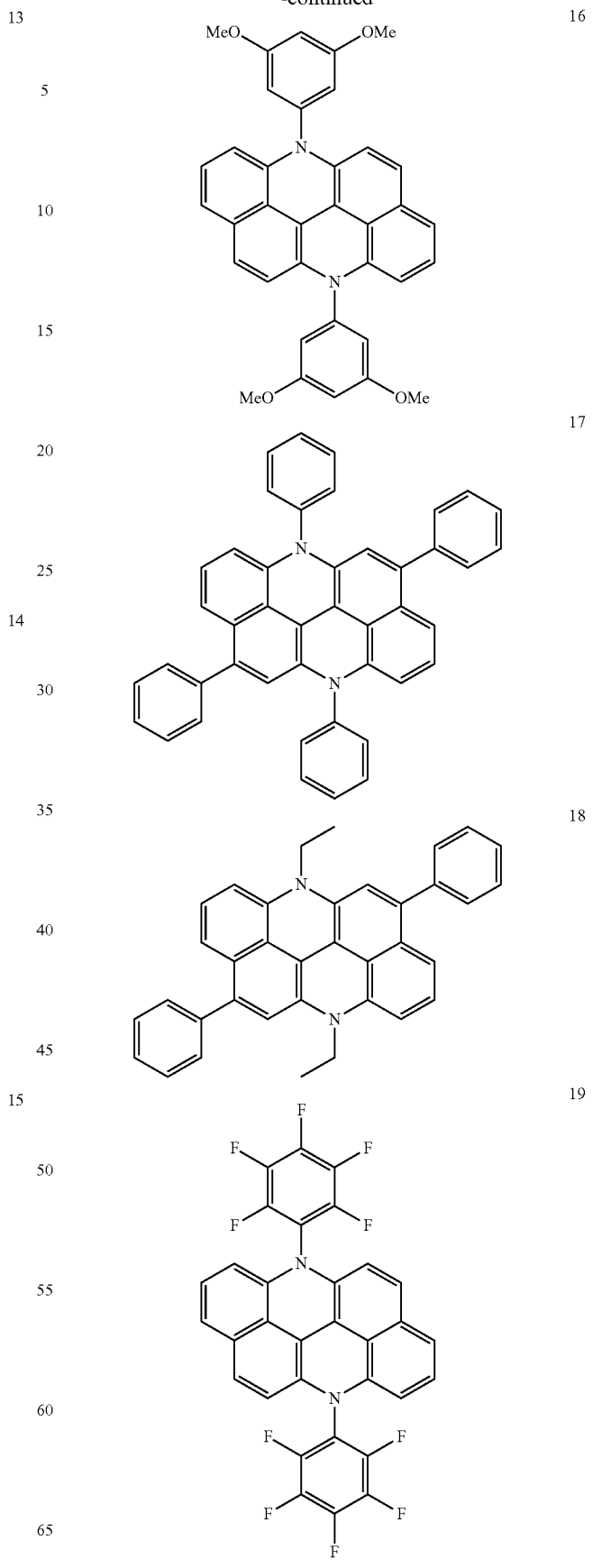

29
20
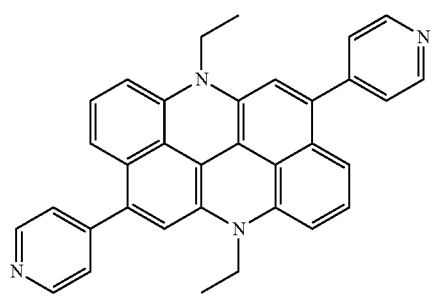
21
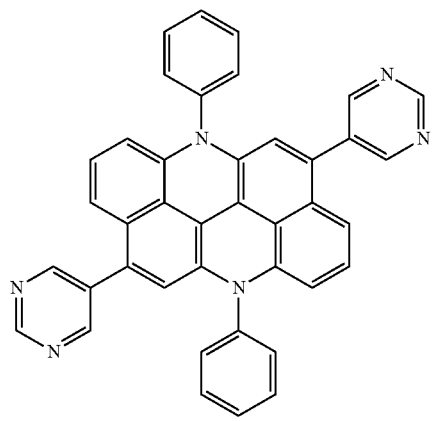
22
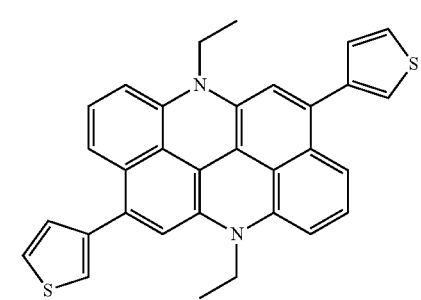
23
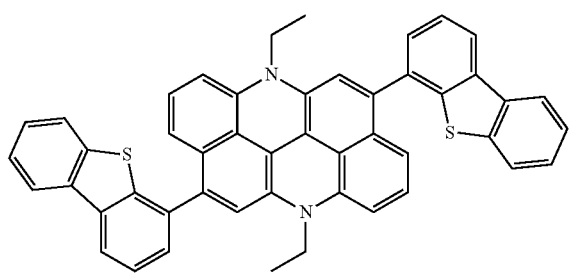
30
24
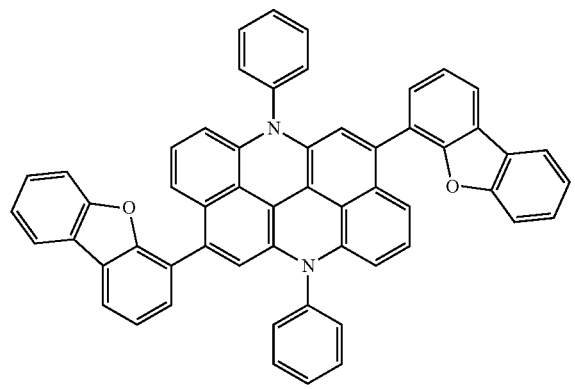
25
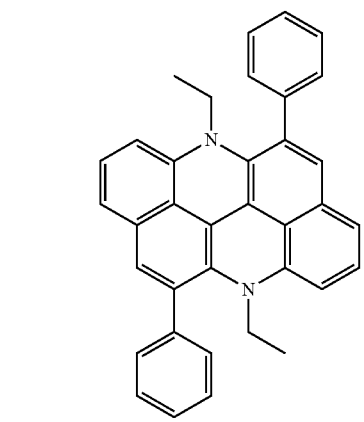
26
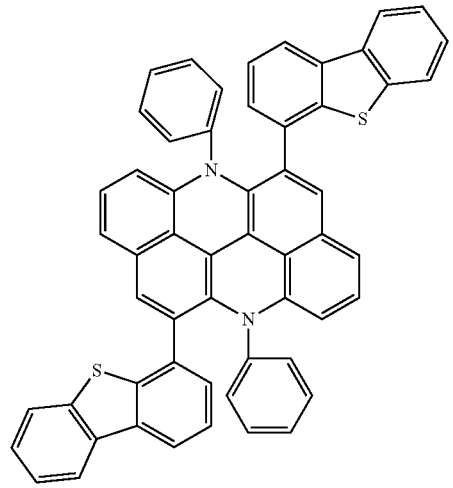

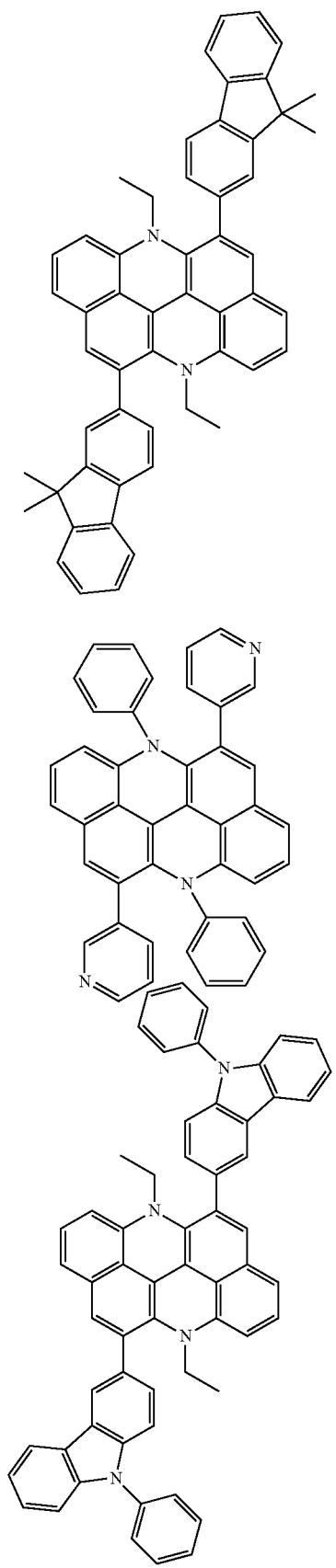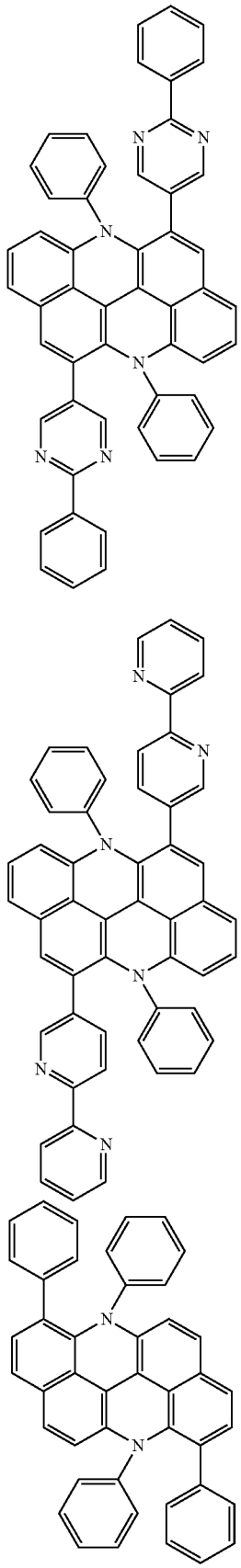

-continued
33
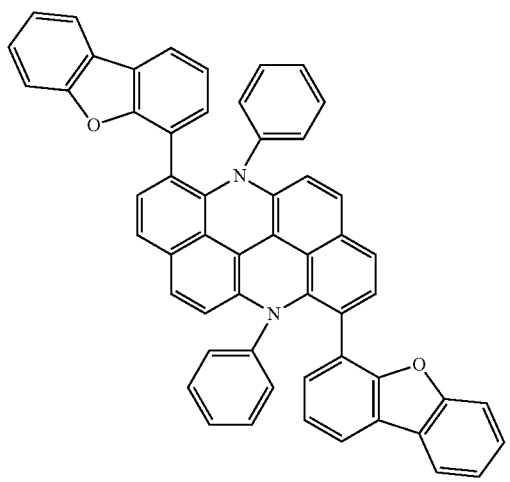
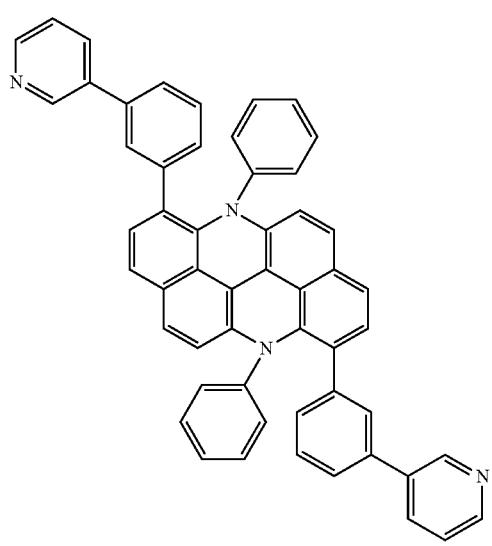
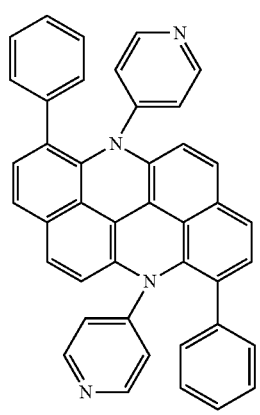
-continued
36
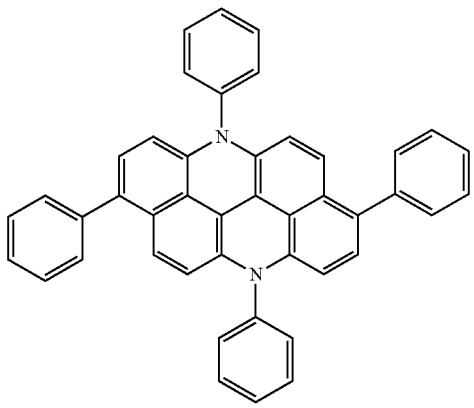
37
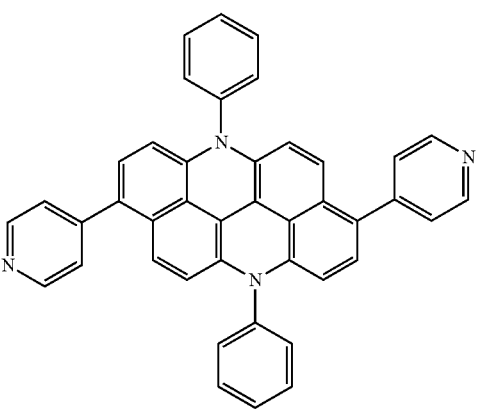
38
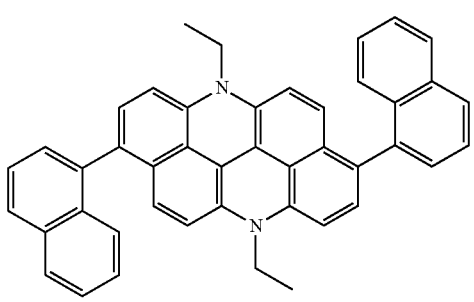
39
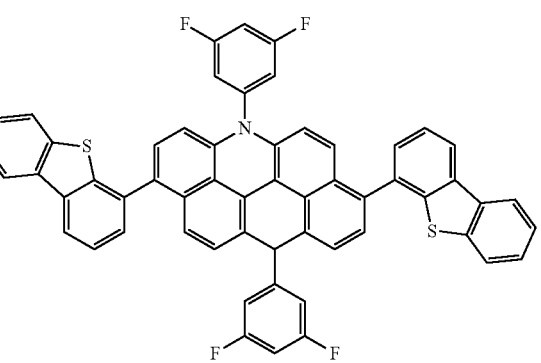

40
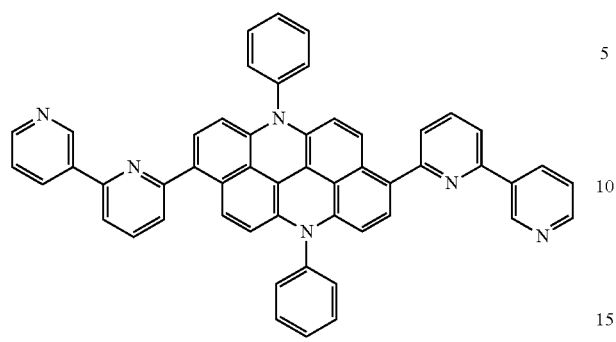
41
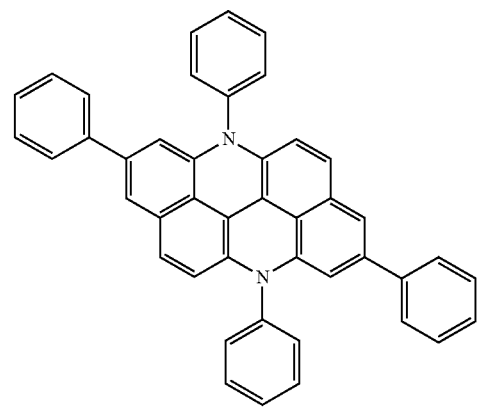
42
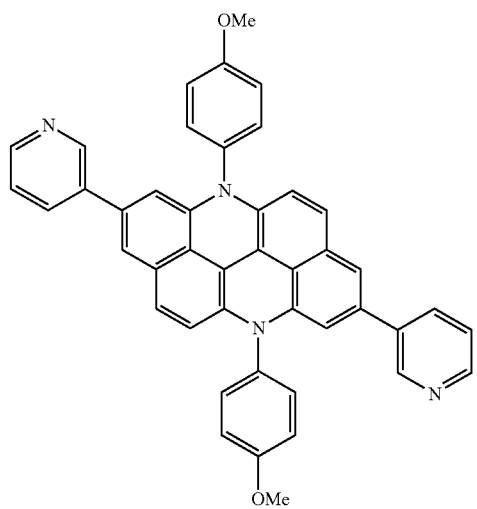
43
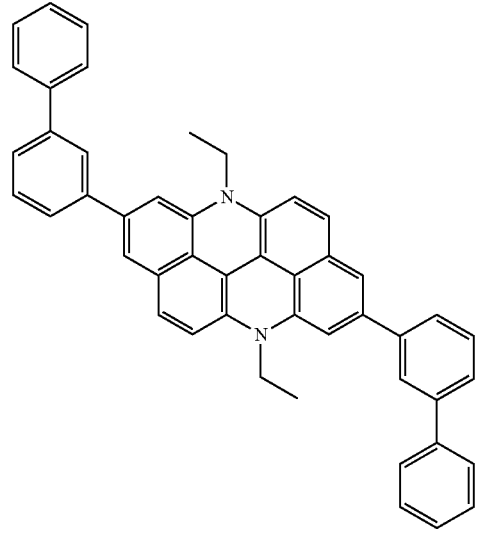
44
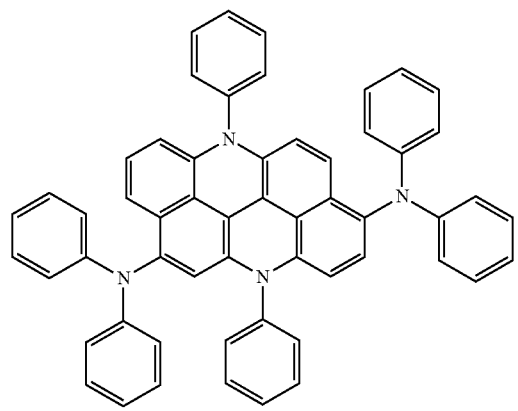
45
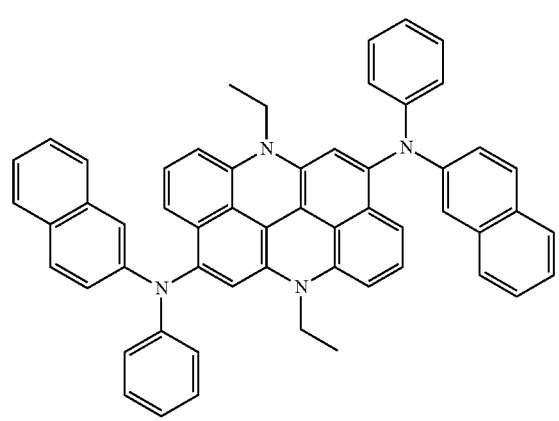

46
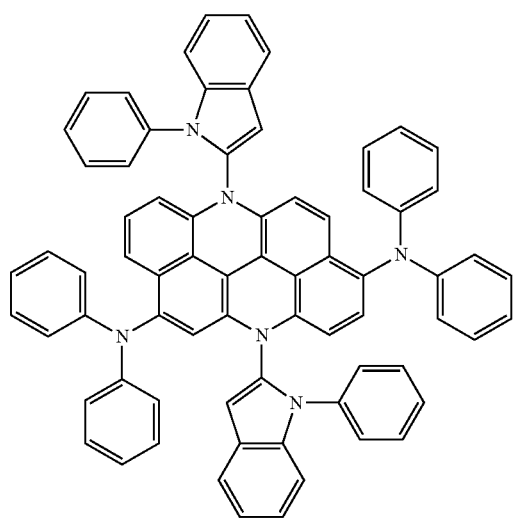
47
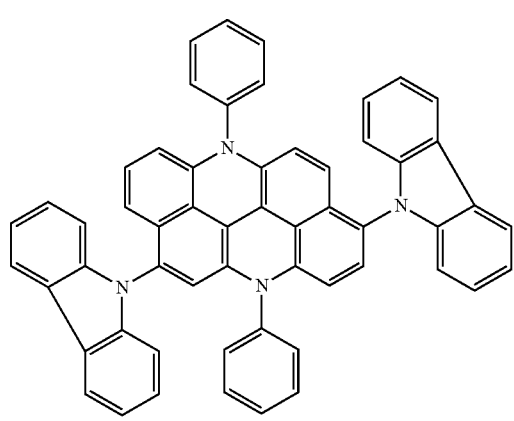
48
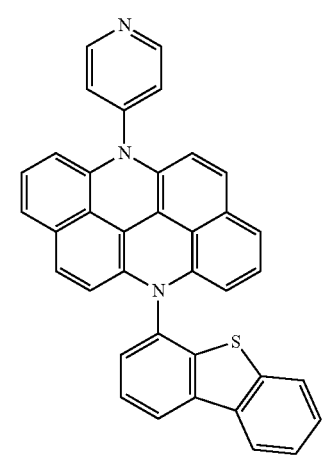
49
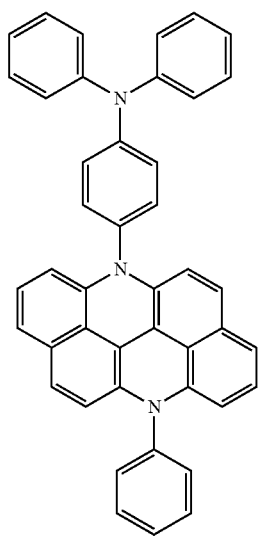
50
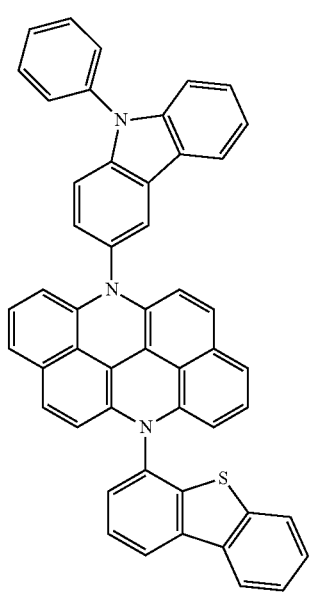
51
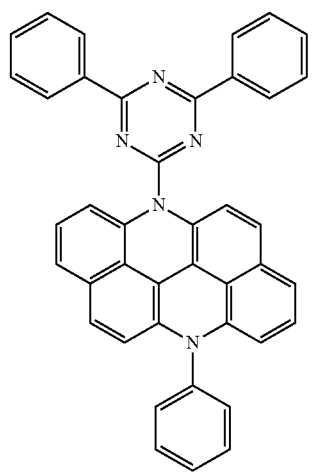

52
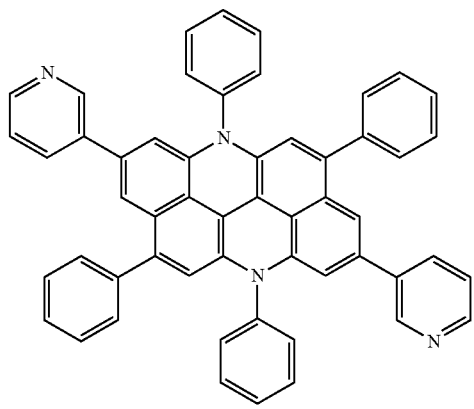
55
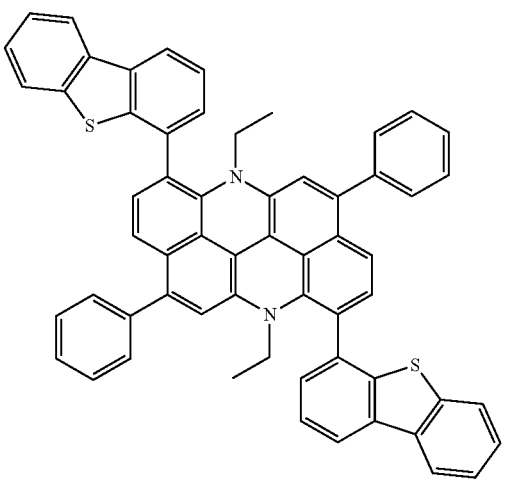
53
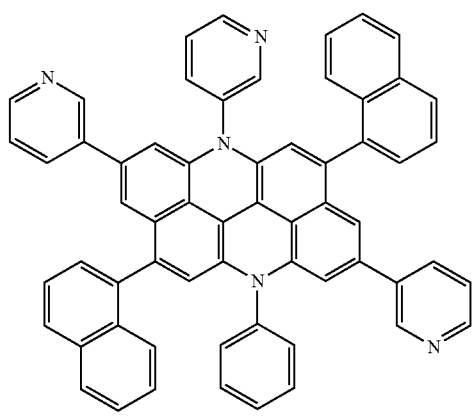
56
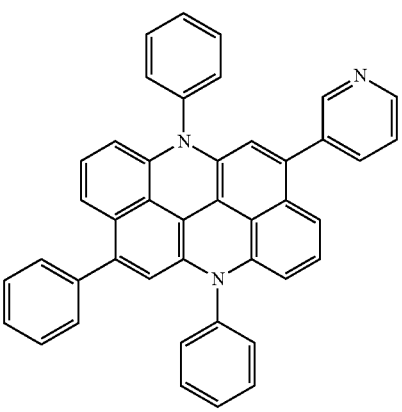
54
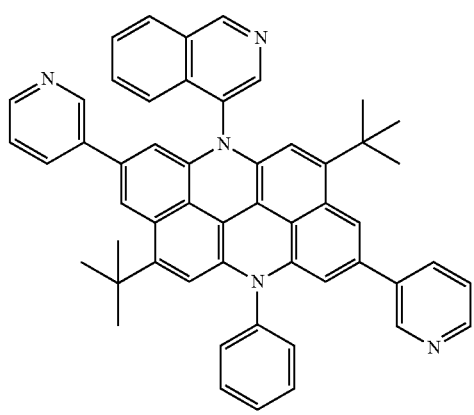
57
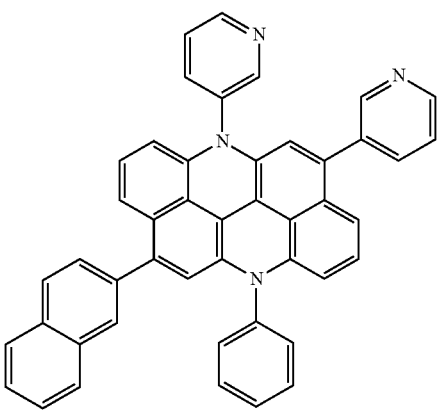

58
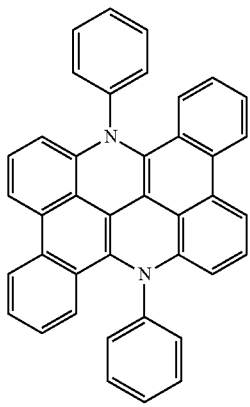
59
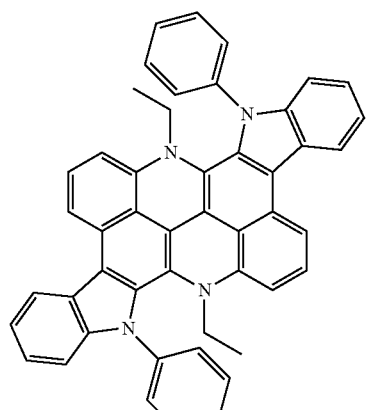
60
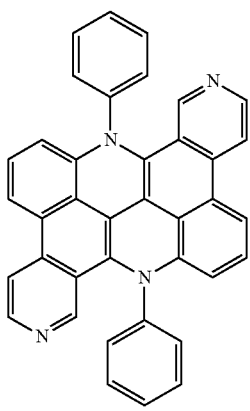
61
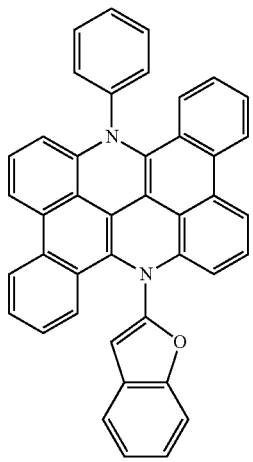
62
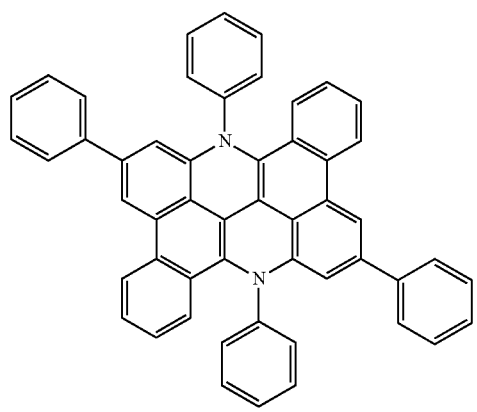
63
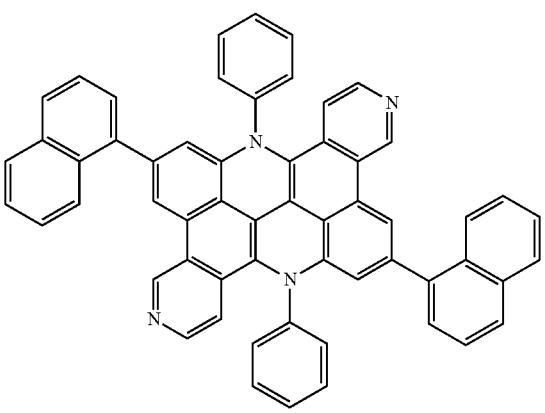

43
-continued
64
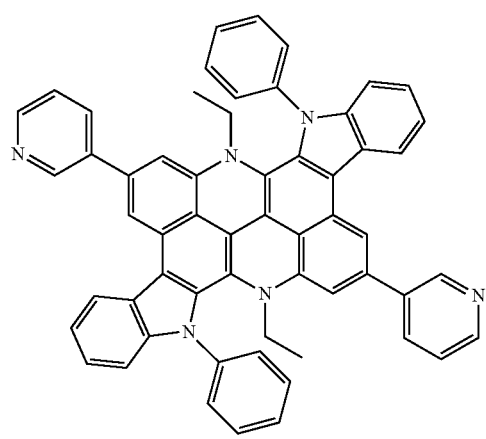
65
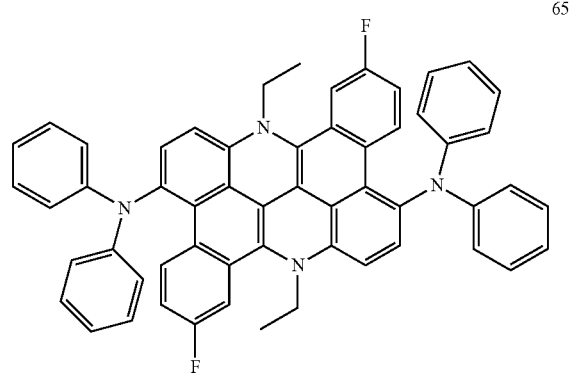
66
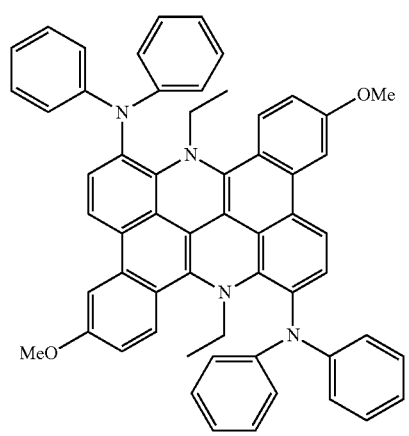
44
-continued
67
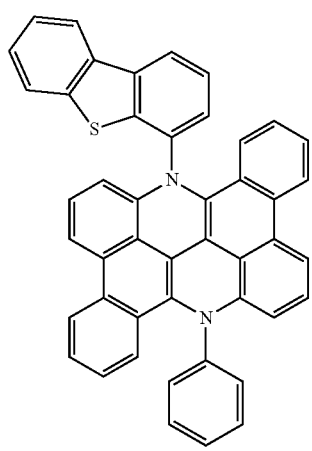
68
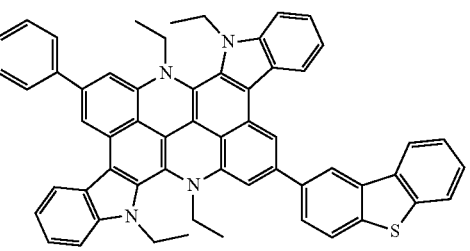
69
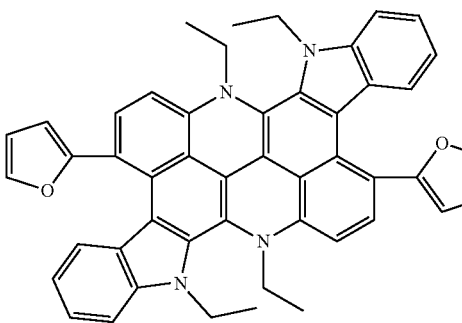

70
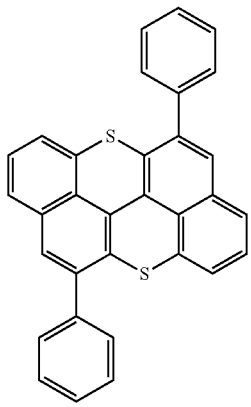
71
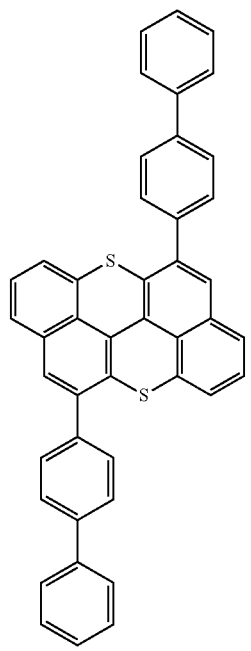
72
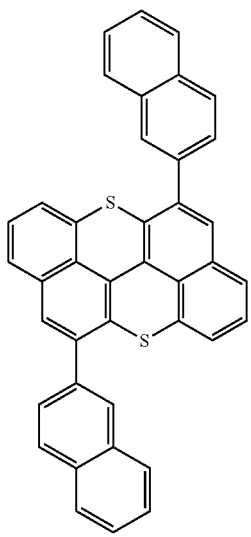
73
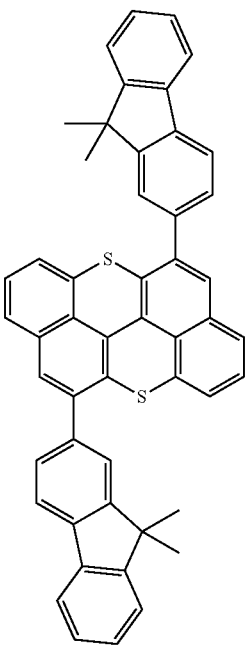
74
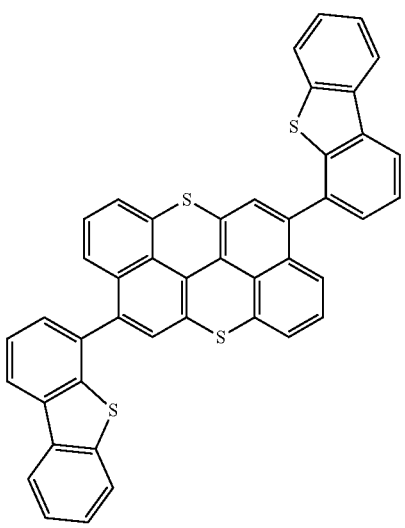
75
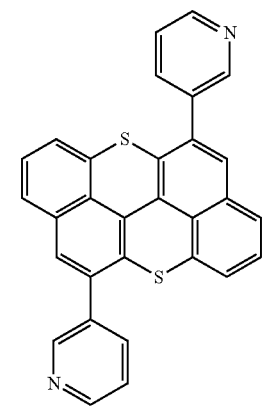

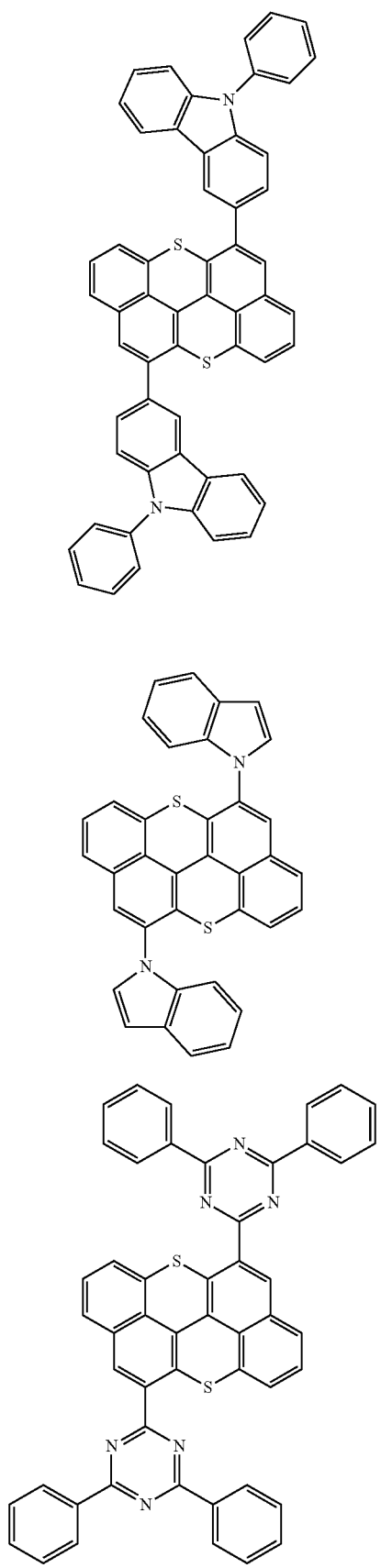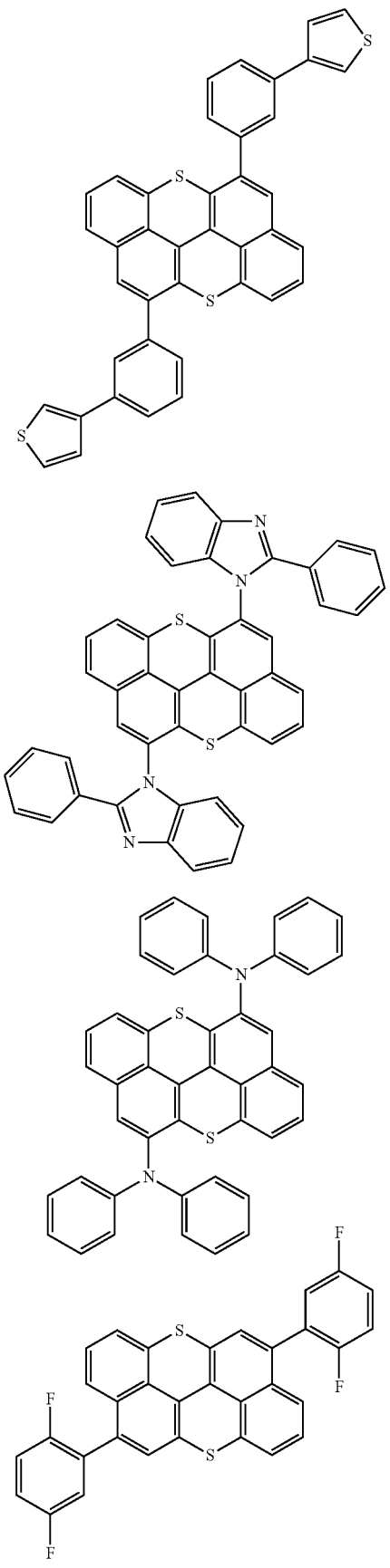

-continued
83
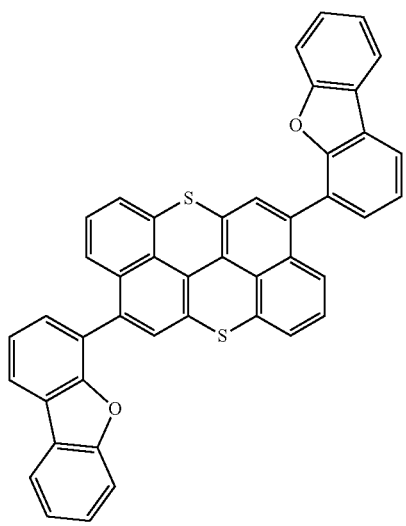
84
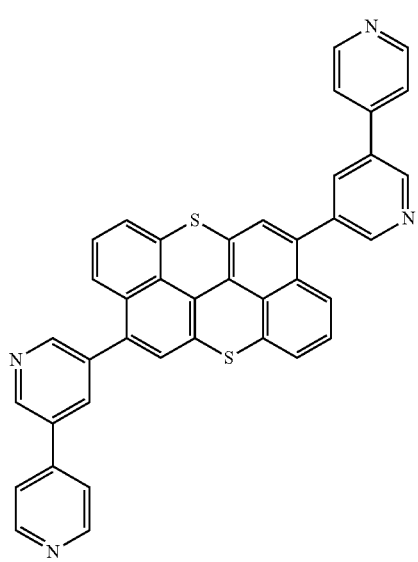
85
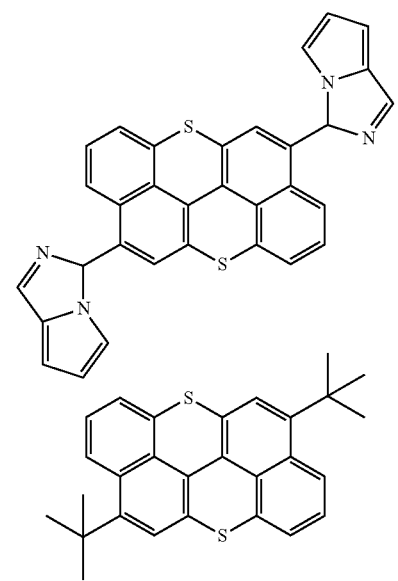
86
-continued
87
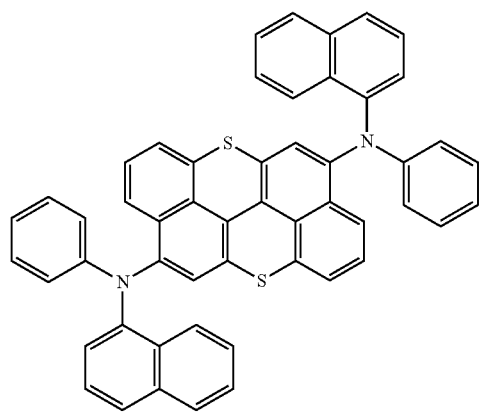
88
89
90

-continued
91
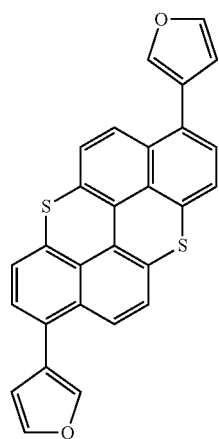
92
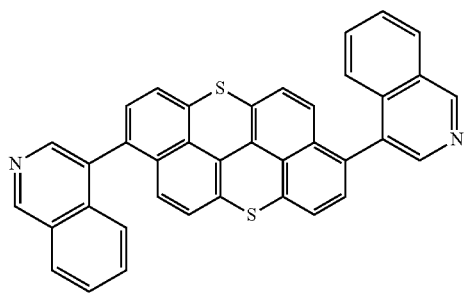
93
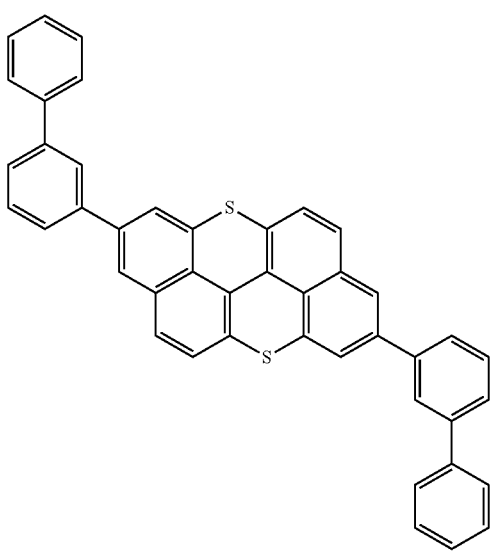
-continued
94
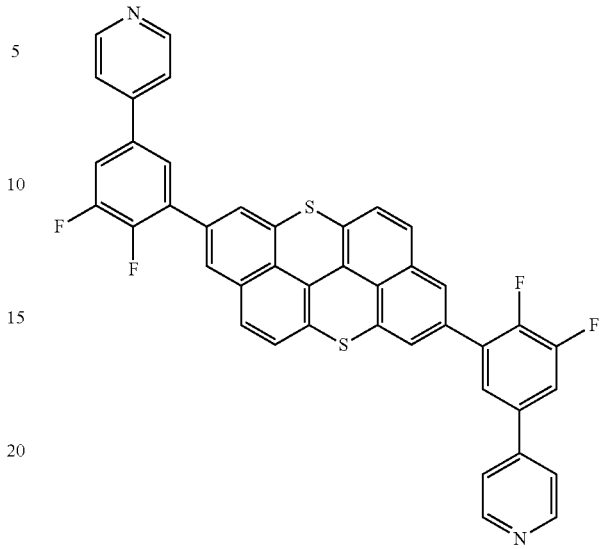
95
96
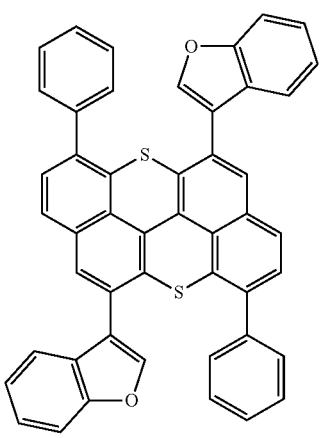

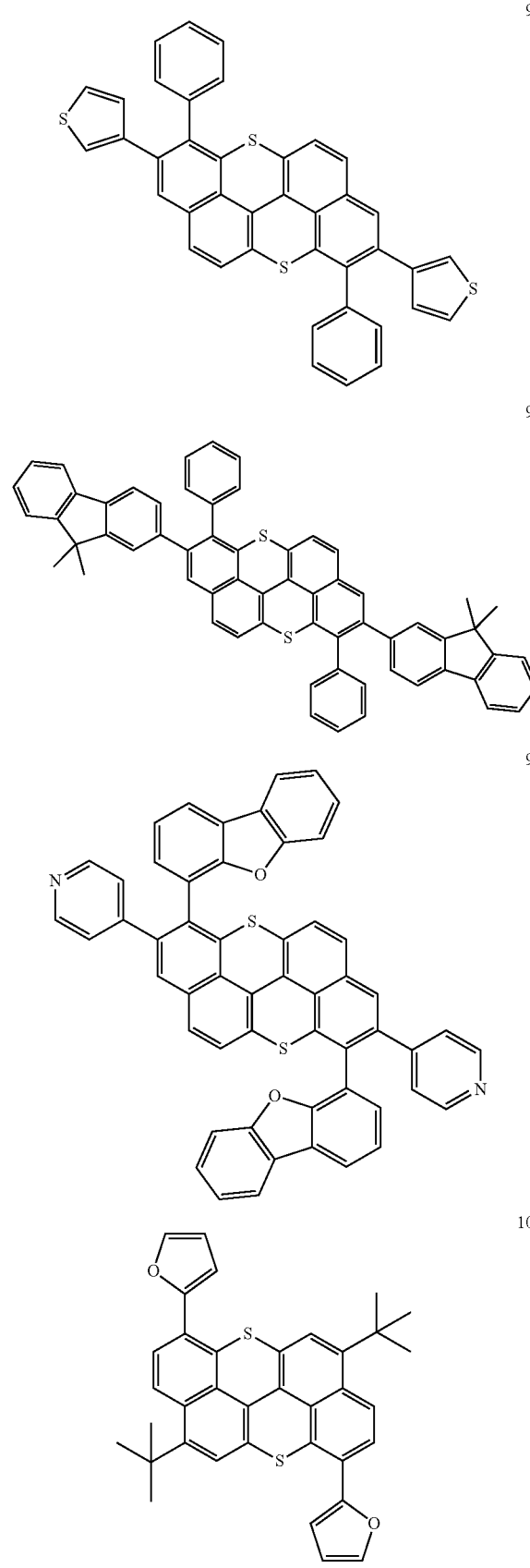

105
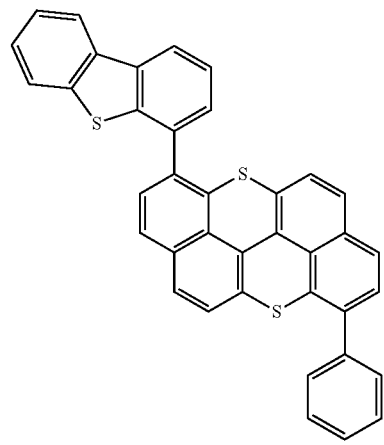
106
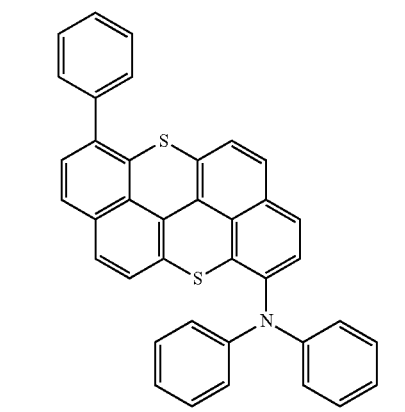
107
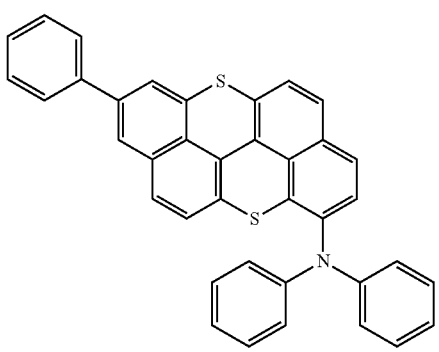
108
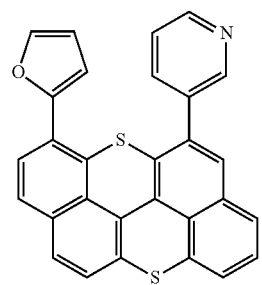
109
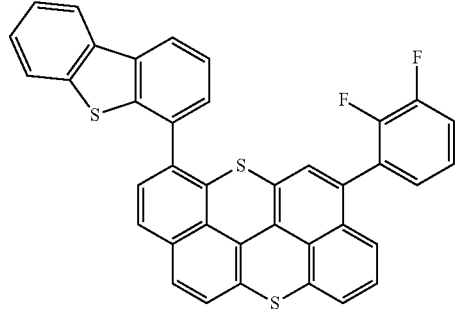
110
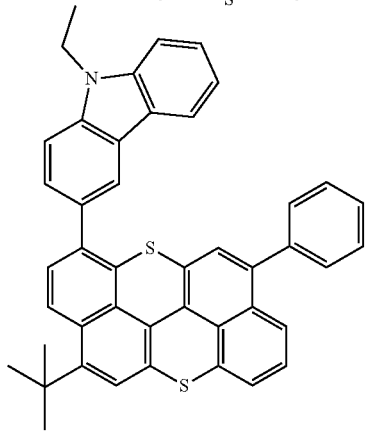
111
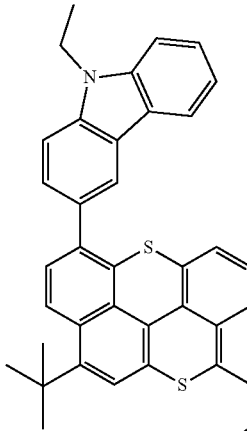
112
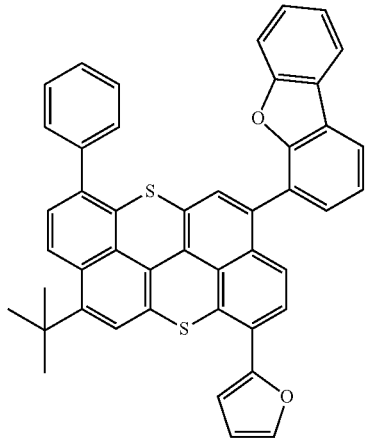

57
-continued
113
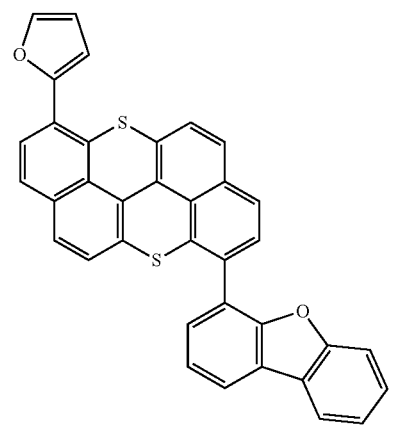
114
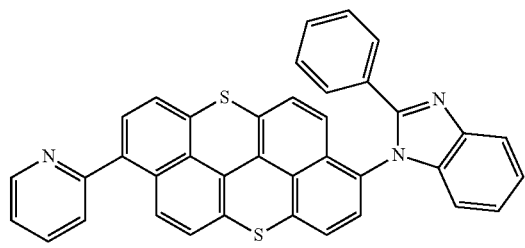
115
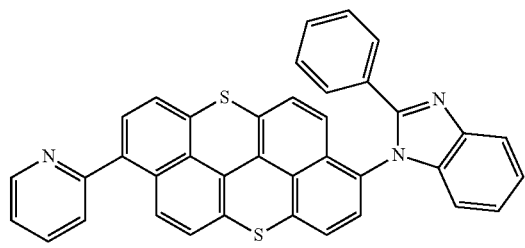
116
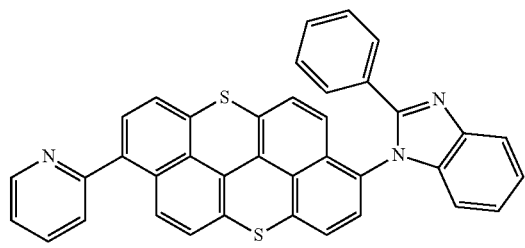
58
-continued
117
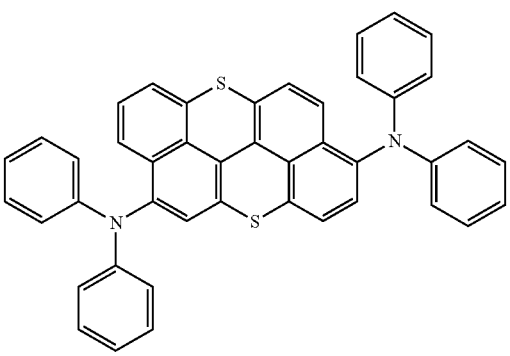
118
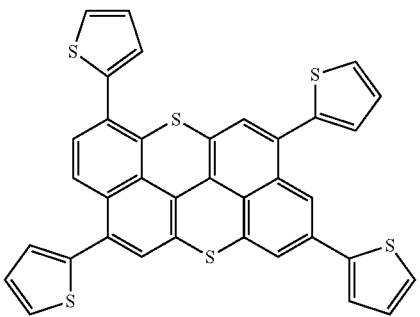
119
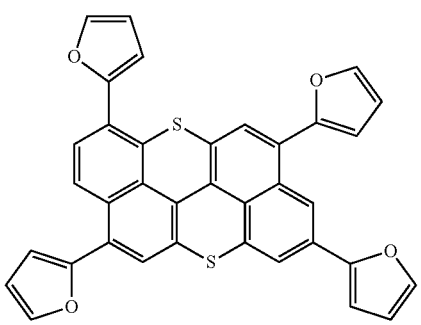
120
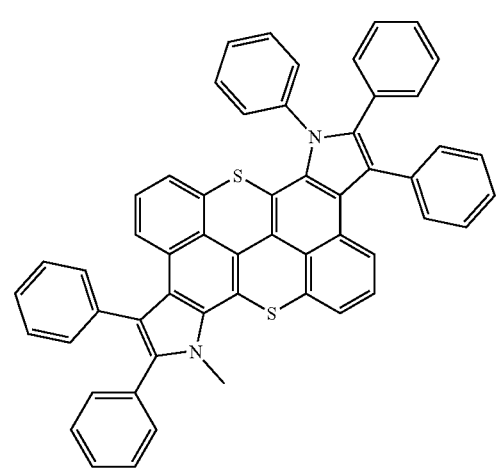

121

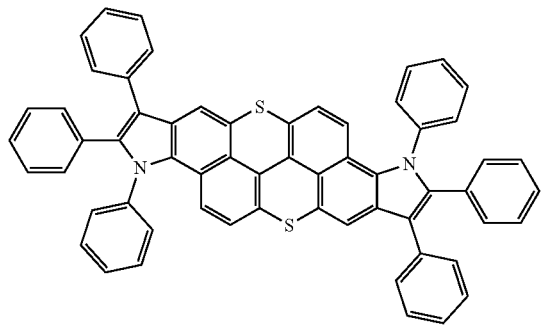

122

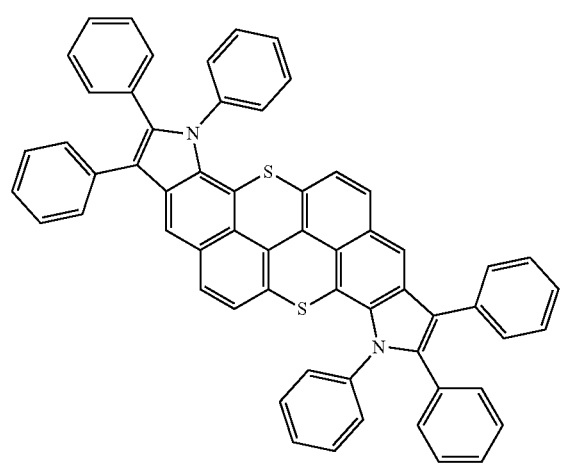

123

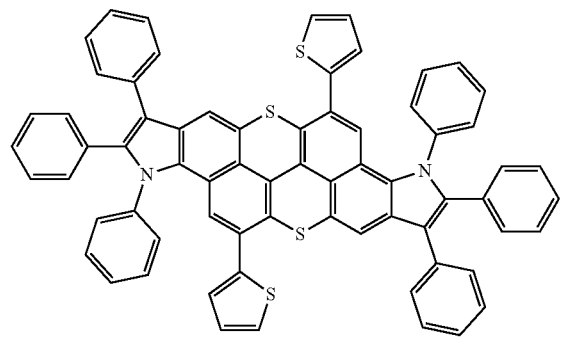

124

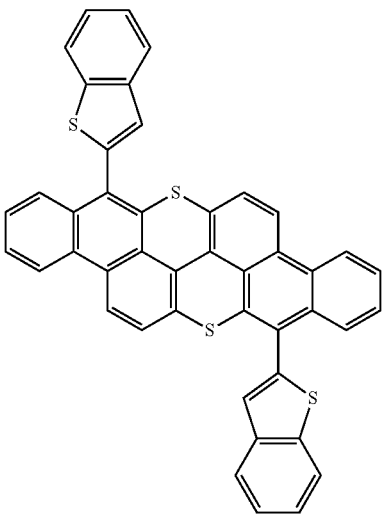

125

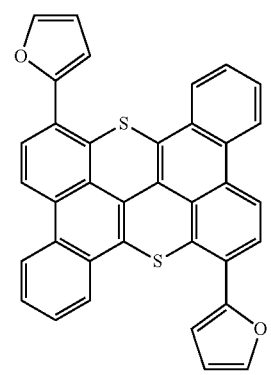

126

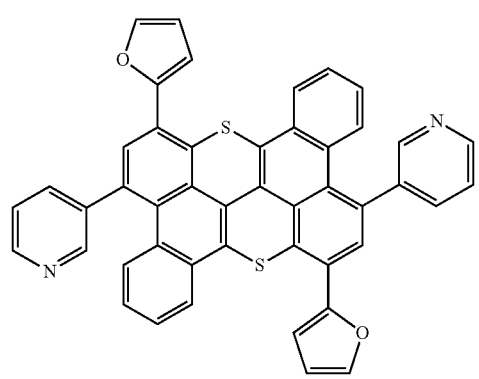

Another aspect of the present invention provides an organic light-emitting device including a first electrode, a second electrode, and an organic layer disposed between the first electrode and the second electrode, wherein the organic layer may include a first layer containing the heterocyclic compound of Formula 1 described above.

The first layer may be at least one layer selected from the group consisting of a hole injection layer, a hole transport layer, a functional layer having both hole injection and hole transport capabilities, an electron injection layer, an electron transport layer, and a functional layer having both electron injection and electron transport capabilities.

The first layer may be an emission layer, and the heterocyclic compound Formula 1 may be used as a host or dopant for a fluorescence or phosphorescence device.

In some embodiments the organic layer of the organic light-emitting device may include an emission layer, a hole transport layer and an electron transport layer. The first layer may be an emission layer that further includes a common anthracene compound, arylamine compound, or styryl compound.

In addition, at least one hydrogen atom in the anthracene, arylamine or styryl compound may be substituted with a substituent described above in conjunction with the unsubstituted $C_1$-$C_{60}$ alkyl group. The arylamine refers to a $C_5$-$C_{60}$ arylamine group.

In some embodiments the organic layer of the organic light-emitting device may include an emission layer, a hole transport layer, and an electron transport layer, and the first layer may be an emission layer of which one of a red emission layer, a green emission layer, a blue emission layer, and a white emission layer may further include a widely-known phosphorescent compound.

In an embodiment the organic layer of the organic light-emitting device may be a blue emission layer. When the first layer of the organic light-emitting device is a blue emission layer, the heterocyclic compound of Formula 1 may be used as a blue host.

The first electrode may be an anode, and the second electrode may be a cathode, but the reverse is also possible.

In some embodiments, the organic light-emitting device may have a first electrode/hole injection layer/emission layer/ second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure. In some other embodiments, the organic light-emitting device may have a first electrode/single layer having both hole injection and hole transport capabilities/emission layer/ electron transport layer/second electrode structure, or a first electrode/single layer having both hole injection and hole transport capabilities/emission layer/electron transport layer/ electron injection layer/second electrode structure. In still some other embodiments, the organic light-emitting device may have a first electrode/hole transport layer/emission layer/ single layer having both electron injection and electron transport capabilities/second electrode structure, a first electrode/ hole injection layer/emission layer/single layer having both electron injection and electron transport capabilities/second electrode structure, or a first electrode/hole injection layer/ hole transport layer/emission layer/single layer having both electron injection and electron transport capabilities/second electrode structure.

In some embodiments of the present invention, the organic light-emitting device may have any of a variety of structures, for example, may be either a top-emission organic light-emitting device or a bottom-emission organic light-emitting device.

In some embodiments, the organic layer of the organic light-emitting device may further include, but are not limited to, a hole injection layer, a hole transport layer, a functional layer having both hole injection and hole transport capabilities, an emission layer, a hole blocking layer, an electron transport layer, an electron injection layer, or a combination of at least two thereof. At least one of the hole injection layer, the hole transport layer, and the functional layer having both hole injection and hole transport capabilities may further include a charge generating material for improved layer conductivity, in addition to the heterocyclic compound of Formula 1 described above, a widely-known hole injection material, and a widely-known hole transport material.

The charge generating material may be, for example, a p-dopant. Non-limiting examples of the p-dopant are quinone derivatives such as tetracyanoquinonedimethane (TCNQ), 2,3,5,6-tetrafluoro-tetracyano-1,4-benzoquinonedimethane (F4TCNQ), and the like; metal oxides such as tungsten oxide, molybdenum oxide, and the like; and cyano-containing compounds such as Compound 100 below.

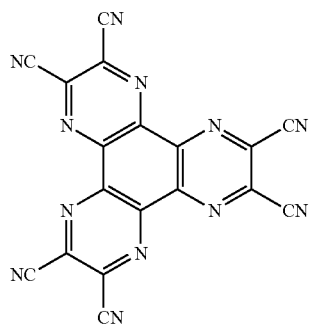

Compound 100

When the hole injection layer, the hole transport layer, or the functional layer having both hole injection and hole transport capabilities further includes a charge generating material, the charge generating material may be, but not limited to, homogeneously dispersed or inhomogeneously distributed in the layer.

In some embodiments the electron transport layer of the organic light-emitting device may further include an electron-transporting organic compound and a metal-containing material. Non-limiting examples of the electron-transporting organic compound include 9,10-di(naphthalen-2-yl)anthracene (ADN), and anthracene-based compounds, such as Compounds 101 and 102 below.

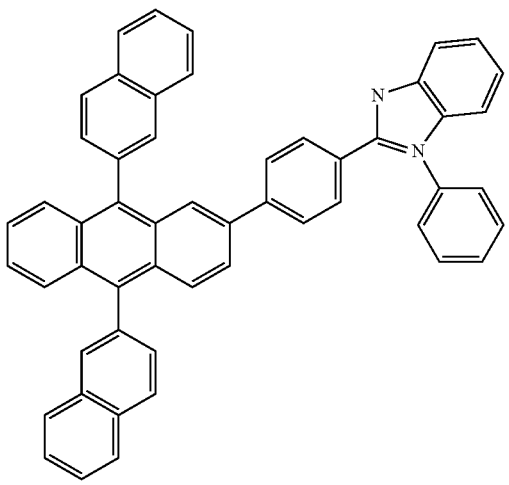

Compound 101

Compound 102

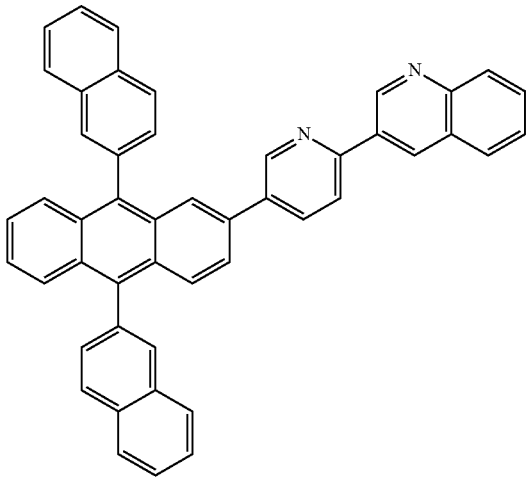

The metal-containing material may include a lithium (Li) complex. Non-limiting examples of the Li complex include lithium quinolate (LiQ) and Compound 103 below:

Compound 103

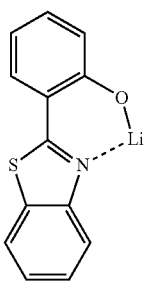

Figure 2:
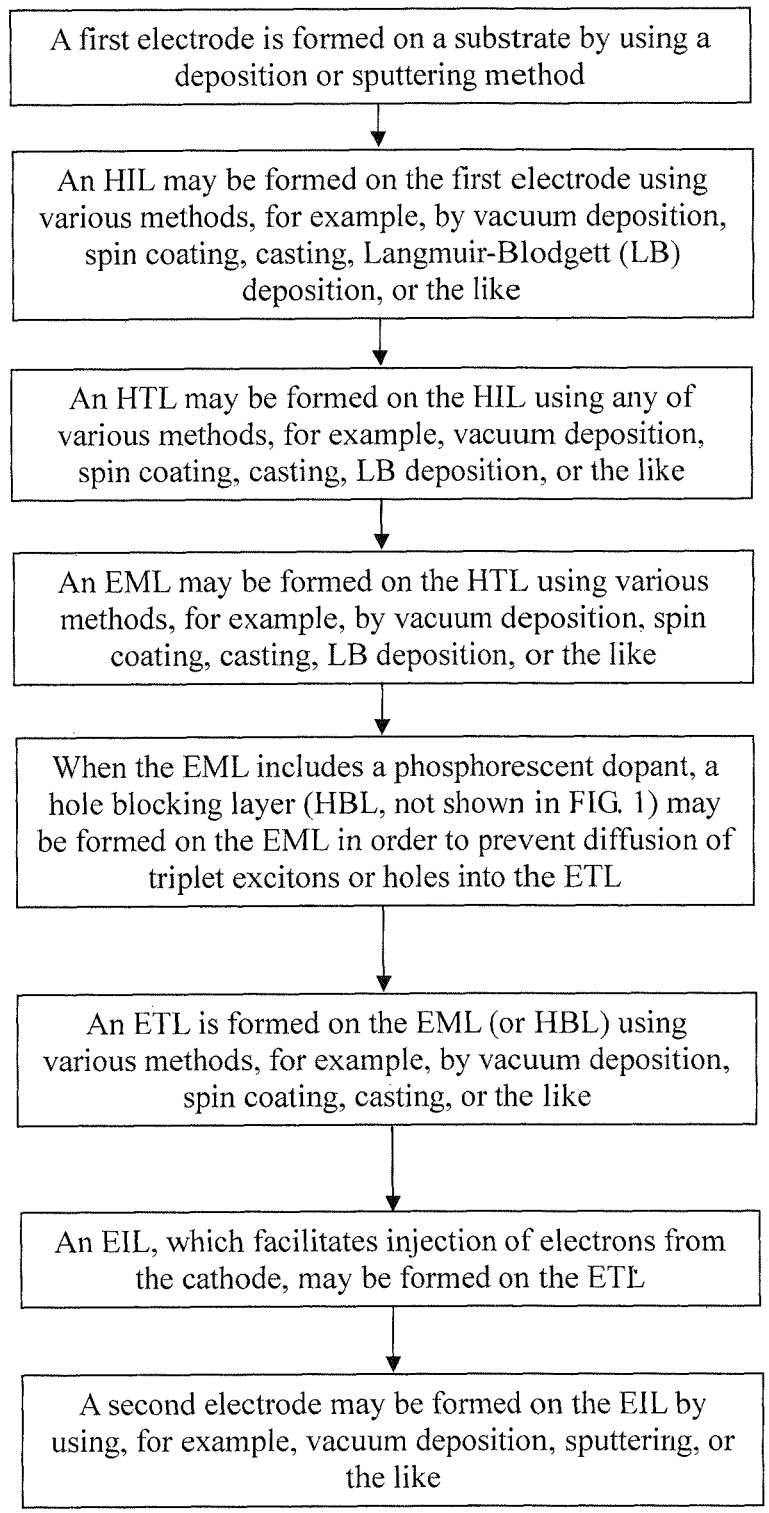
FIG. 2 illustrates a method of making an organic light-emitting device of the present invention.

Hereinafter, a method of manufacturing an organic light-emitting device according to an embodiment of the present invention will be described with reference to FIG. 1. FIG. 1 illustrates the structure of an organic light-emitting device according to an embodiment of the present invention. FIG. 2 shows a method of manufacturing an organic light-emitting device according to an embodiment of the present invention. Referring to FIG. 1, the organic light-emitting device according to the present embodiment includes a substrate (not shown), a first electrode (anode), a hole injection layer (HIL), a hole transport layer (HTL), an emission layer (EML), an electron transport layer (ETL), an electron injection layer (EIL), and a second electrode (cathode).

First, a first electrode is formed on a substrate by using a deposition or sputtering method. The first electrode may be formed from a first electrode material having a high work function. The first electrode may constitute an anode or a cathode. The substrate may be a substrate conventionally used in organic light-emitting devices, and may be, for example, a glass substrate or a transparent plastic substrate with strong mechanical strength, thermal stability, transparency, surface smoothness, ease of handling, and water resistance. Examples of the first electrode material are materials, such as indium tin oxide (ITO), indium zinc oxide (IZO), tin oxide ($SnO_2$), zinc oxide (ZnO), aluminum (Al), silver (Ag), and magnesium (Mg), which have high conductivity. The first electrode may be formed as a transparent or reflective electrode.

Next, the HIL may be formed on the first electrode using various methods, for example, by vacuum deposition, spin coating, casting, Langmuir-Blodgett (LB) deposition, or the like.

When the HIL is formed using vacuum deposition, the deposition conditions may vary according to the material that is used to form the HIL, and the structure and thermal characteristics of the HIL. For example, the deposition conditions may include a deposition temperature of about 100 to about 500° C., a vacuum pressure of about $10^{-8}$ to about $10^{-3}$ torr, and a deposition rate of about 0.01 to about 100 Å/sec.

When the HIL is formed using spin coating, coating conditions may vary according to the material used to form the HIL, and the structure and thermal properties of the HIL. For example, the coating conditions may include a coating speed of about 2000 rpm to about 5000 rpm, and a thermal treatment temperature of about 80° C. to about 200° C. at which the solvent remaining after coating may be removed.

The HIL may be formed of any material that is commonly used to form a HIL. Examples of the material that can be used to form the HIL are a phthalocyanine compound such as copperphthalocyanine, 4,4',4"-tris(3-methylphenylphenylamino)triphenylamine (m-MTDATA), N,N'-di(1-naphthyl)-N,N'-diphenylberrzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOTIPSS), polyaniline/camphor sulfonic acid (Pani/CSA), and polyaniline)/poly(4-styrenesulfonate (PANI/PSS), but are not limited thereto.

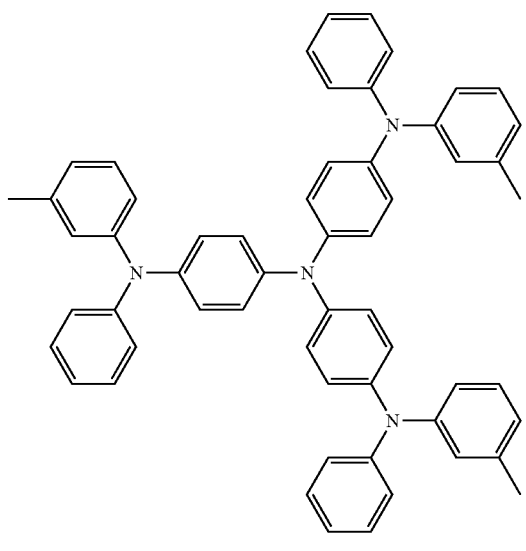

m-MTDATA

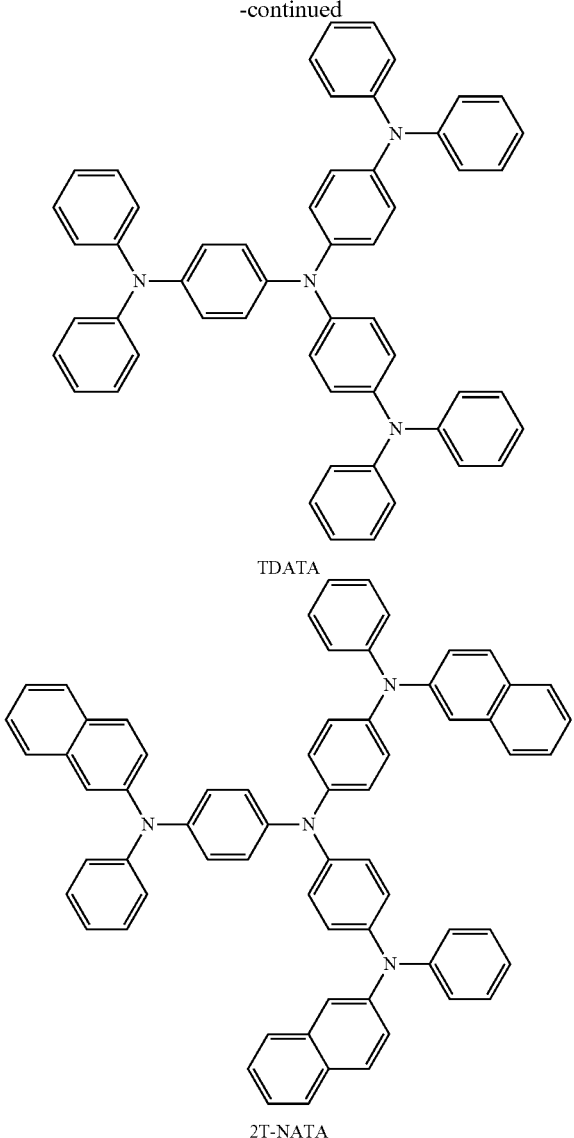

TDATA

2T-NATA

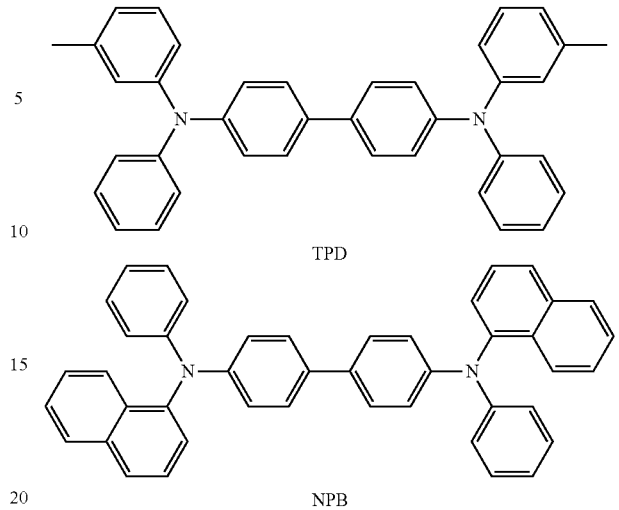

TPD

NPB

The HTL may have a thickness of about 50 Å to about 1000 Å, and in some embodiments, may have a thickness of about 100 Å to about 600 Å. When the thickness of the HTL is within these ranges, the HTL may have good hole transport characteristics without a substantial increase in driving voltage.

Next, the EML may be formed on the HTL using any of a variety of methods, for example, by vacuum deposition, spin coating, casting, LB deposition, or the like. When the EML is formed using vacuum deposition or spin coating, the deposition or coating conditions may be similar to those applied to form the HIL, though the deposition or coating conditions may vary according to the material that is used to form the EML.

The EML may include the heterocyclic compound of Formula 1 described above. For example, the heterocyclic compound of Formula 1 may be used as a host or a dopant. The EML may be formed using any of a variety of well-known light-emitting materials, in addition to the heterocyclic compound of Formula 1. In some embodiments the EML may also be formed using a well-known host and a dopant. Dopants that may be used to form the EML may be either a fluorescent dopant or a phosphorescent dopant which are widely known in the art.

Non-limiting examples of the host are Alq3, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-certbutyl-9,10-di-2-naphthylanthracene (TBADN), E3, and distyrylarylene (DSA).

The HIL may have a thickness of about 100 Å to about 10000 Å, and in some other embodiments, may have a thickness of about 100 Å to about 1000 Å. When the thickness of the HIL is within these ranges, the HIL may have good hole injection characteristics without an increase in driving voltage.

Next, the HTL may be formed on the HIL using any of a variety of methods, for example, vacuum deposition, spin coating, casting, LB deposition, or the like. When the HTL is formed using vacuum deposition or spin coating, the deposition or coating conditions may be similar to those applied to form the HIL, though the deposition or coating conditions may vary according to the material that is used to form the HTL.

The HTL may be formed of the heterocyclic compound of Formula 1 above or any known HTL material. Non-limiting examples of such HTL materials include carbazole derivatives such as N-phenylcarbazole or polyvinylcarbazole, and amine derivatives having an aromatic condensed ring, such as NPB, N,N'-bis(3-methylphenyl)-N,N'-diphenyl-[1,1-biphenyl]-4,4'-diamine (TPD), or the like.

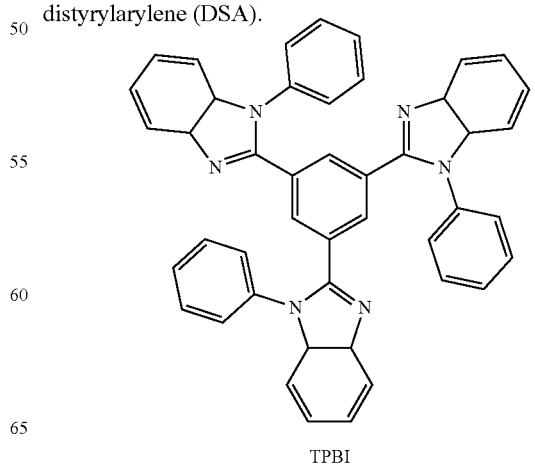

TPBI

-continued

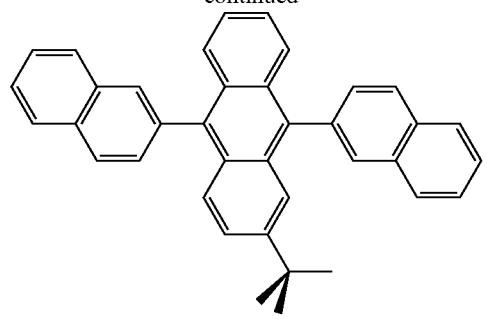
TBADN

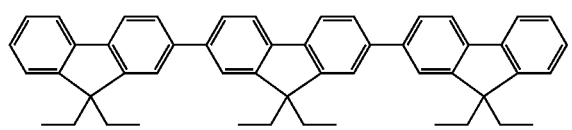
E3

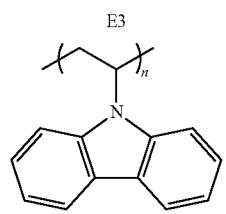
PVK

Examples of red dopants include, but are not limited to, platinum(II) oclaethylporphyrin (PtOEP), Ir(piq)$_3$, Btp$_2$Ir(acac), and DCJTB.

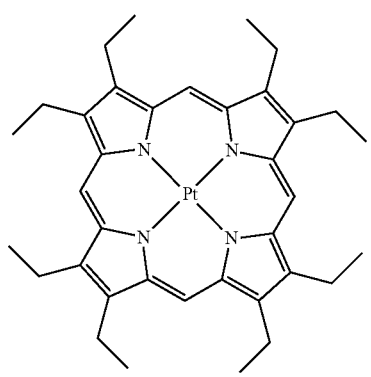
PtOEP

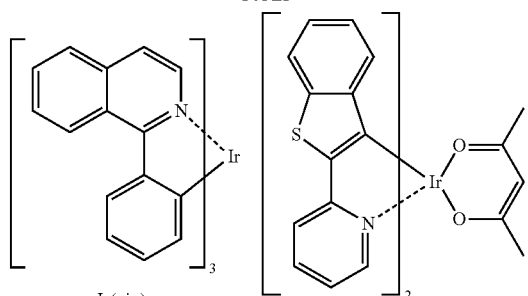
Ir(piq)$_3$

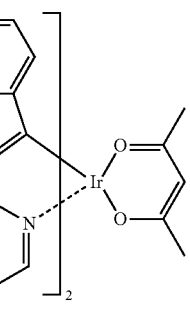
Btp$_2$Ir(acac)

Examples of green dopants may include, but are not limited to, Ir(ppy)$_3$ (where "ppy" denotes phenylpyridine), Ir(ppy)$_2$(acac), Ir(mpyp)$_3$, and C545T.

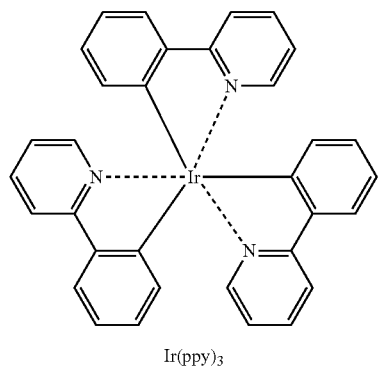
Ir(ppy)$_3$

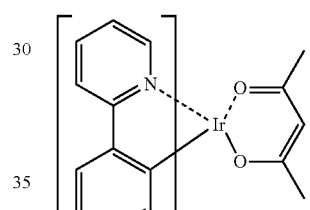
Ir(ppy)$_2$(acac)

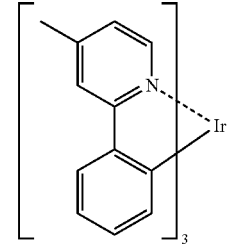
Ir(mpyp)$_3$

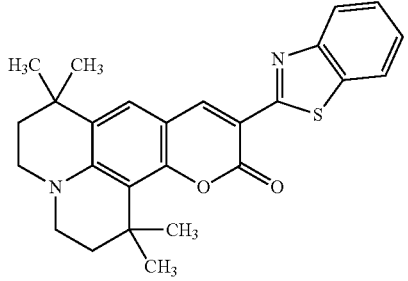
C545T

Examples of blue dopants include F$_2$Irpic, (F$_2$ppy)$_2$Ir(tmd), Ir(dfppz)$_3$, ter-fluorene, 4,4'-bis(4-diphenylaminostyryl)biphenyl (DPAVB1), and 2,5,8,11-tetra-t-butyl phenylene (TBP), but are not limited thereto.

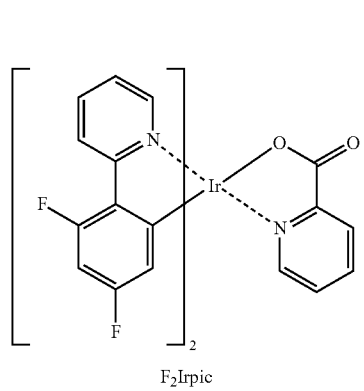
F₂Irpic

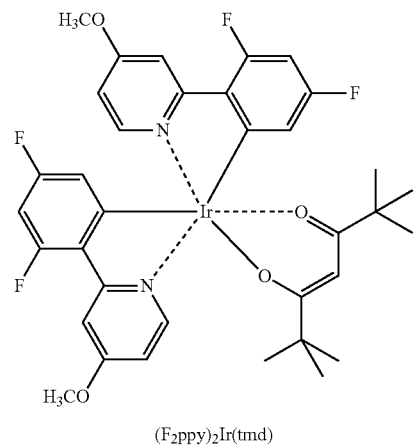
(F₂ppy)₂Ir(tmd)

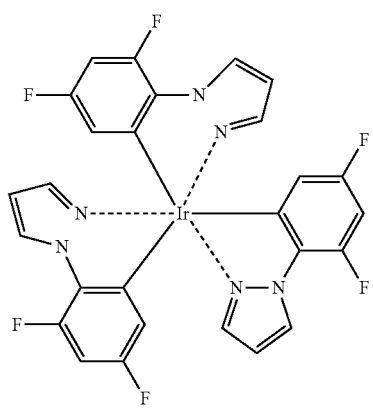
Ir(dfppz)₃

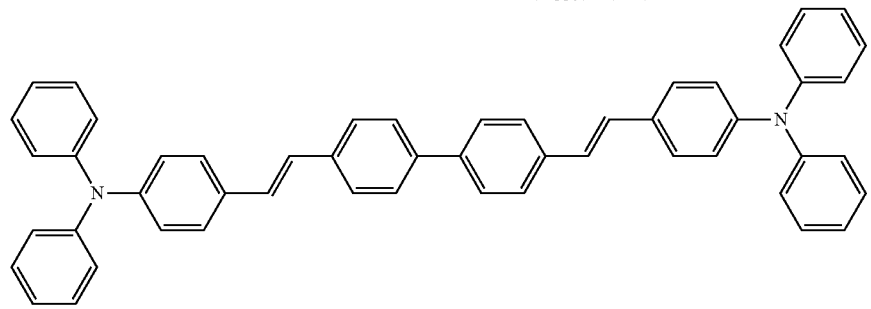
DPAVBi

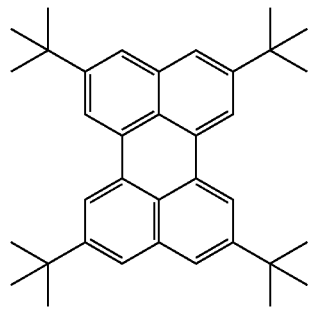
TBP

The amount of the dopant may be from about 0.1 to about 20 parts by weight, and in some other embodiments, may be from about 0.5 to about 12 parts by weight, based on 100 parts by weight of the EML material (equivalent to the total weight of the host and dopant). When the amount of the dopant is within these ranges, concentration quenching may be substantially prevented.

The EML may have a thickness of about 100 Å to about 1,000 Å, and in some embodiments, may have a thickness of about 200 Å to about 600 Å. When the thickness of the EML is within these ranges, the EML may have good light-emitting characteristics without a substantial increase in driving voltage.

When the EML includes a phosphorescent dopant, a hole blocking layer (HBL, not shown in FIG. 1) may be formed on the EML in order to prevent diffusion of triplet excitons or holes into the ETL. In this case, the HBL may be formed from any material commonly used to form a HBL. Examples of such HBL materials are, but are not limited to, oxadiazole derivatives, triazole derivatives, phenathroline derivatives, Balq, and BCP.

The HBL may have a thickness of about 50 Å to about 1,000 Å, and in some embodiments, may have a thickness of about 100 Å to about 300 Å. When the thickness of the HBL is within these ranges, diffusion of triplet exitons or holes into the ETL may be readily prevented without a substantial increase in driving voltage. Next, the ETL is formed on the EML (or HBL) using various methods, for example, by vacuum deposition, spin coating, casting, or the like. When the ETL is formed using vacuum deposition or spin coating, the deposition or coating conditions may be similar to those applied to form the HIL, though the deposition or coating conditions may vary according to the material that is used to form the ETL.

The ETL material may be the heterocyclic compound of Formula 1 described above, and in some embodiments, may be any arbitrary material selected from among electron transporting materials widely known in the art. Examples of the ETL material include, but are not limited to, quinoline derivatives, such as tris(8-quinolinolate)aluminum (Alq3), TAZ, and BAlq.

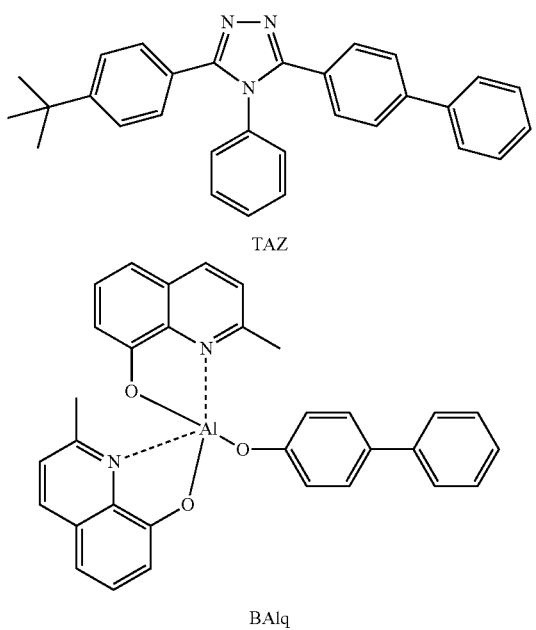

TAZ

BAlq

The ETL may have a thickness of about 100 Å to about 1,000 Å, and in some other embodiments, may have a thickness of about 100 Å to about 500 Å. When the thickness of the ETL is within these ranges, the ETL may have good electron transport characteristics without a substantial increase in driving voltage.

In addition, the EIL, which facilitates injection of electrons from the cathode, may be formed on the ETL.

The EIL may be formed using any known materials used to form an EIL layer, for example, LiF, NaCl, CsF, $Li_2O$, BaO, or the like. The deposition or coating conditions may be similar to those applied to form the HIL, although the deposition and coating conditions may vary according to the material that is used to form the EIL.

The EIL may have a thickness of about 1 Å to 100 Å, and in some embodiments, may have a thickness of about 5 Å to about 90 Å. When the thickness of the EIL is within these ranges, the EIL may have good electron injection characteristics without a substantial increase in driving voltage.

Finally, the second electrode may be formed on the EIL by using, for example, vacuum deposition, sputtering, or the like. The second electrode may constitute a cathode or an anode. The material for forming the second electrode may be a metal, an alloy, or an electrically conductive compound, which are materials having a low work function, or a mixture thereof. Examples of such materials are, but are not limited to, lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission organic light-emitting device, a transparent cathode formed of a transparent material such as ITO or IZO may be used as the second electrode.

According to embodiments of the present invention, the organic light-emitting device may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

According to embodiments, the organic light-emitting device may include a plurality of organic layers, wherein at least one of the organic layers may be formed of the heterocyclic compound of Formula 1 by using a deposition method or a wet method of coating a solution of the heterocyclic compound of Formula 1.

Hereinafter, synthesis examples of Compounds 1, 14, 24, 70 and 83 and examples will be described in detail. However, these examples are presented for illustrative purposes only, and do not limit the scope of the present invention.

EXAMPLES

Representative Synthetic Routes representative synthetic route 1

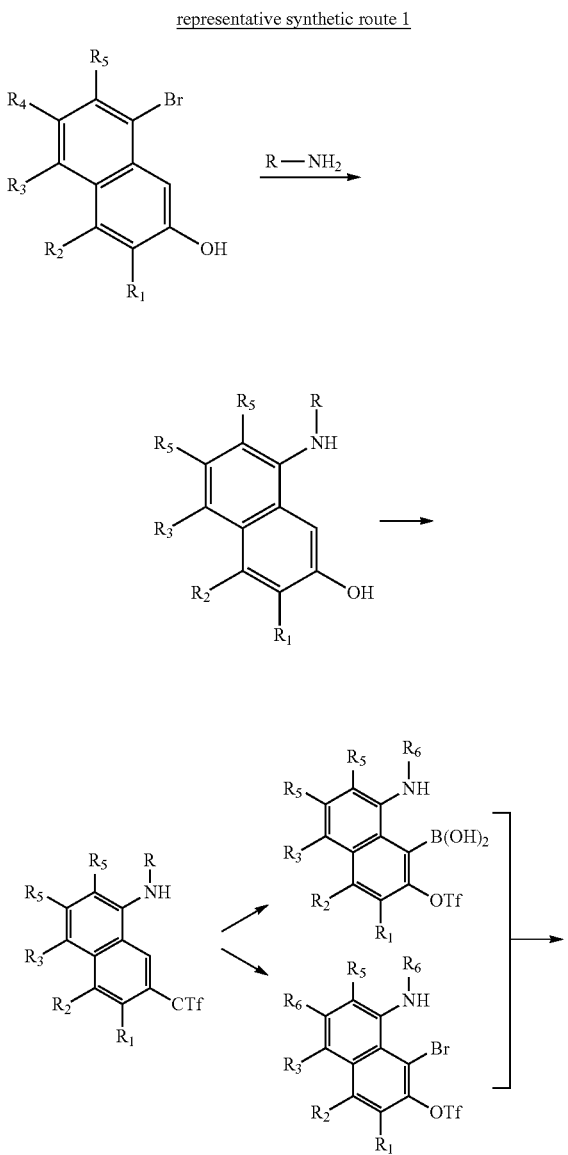

-continued
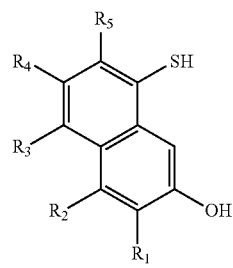
representative synthetic route 2
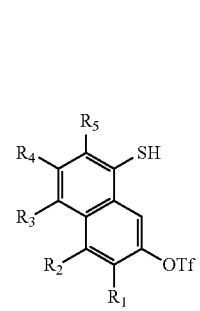
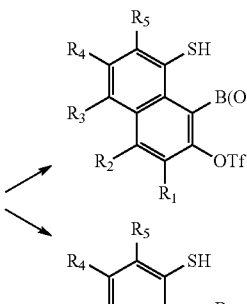
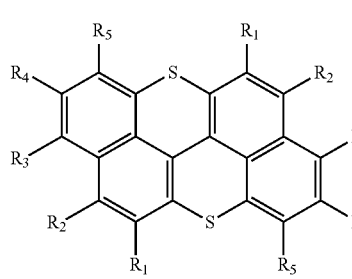
Representative Synthesis Example
Synthesis of Compound 1
Synthesis of Intermediate 1-a
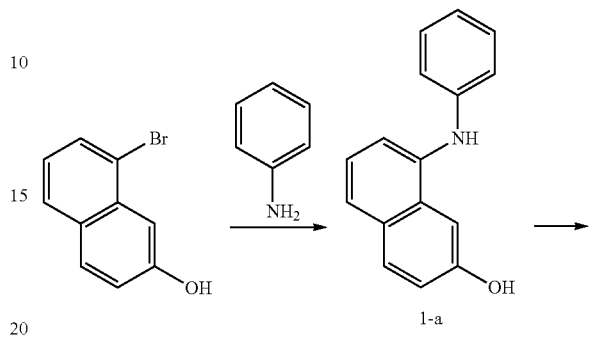
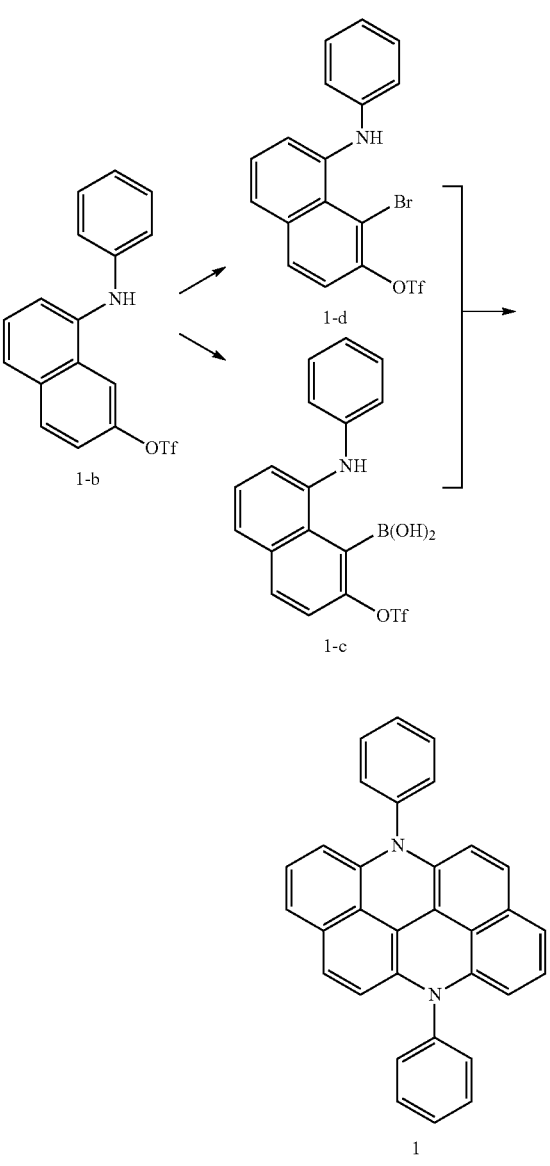

Synthesis of Intermediate 1-a

After 10.0 g (44.83 mmol) of 8-bromo-naphthalene-2-ol was dissolved in 100 mL of toluene, 5 g (53.79 mmol) of aniline, 6.5 g (67.24 mmol) of sodium tert-butoxide and 3.3 g (3.59 mmol) of tris(dibenzylideneacetone)dipalladium(0) were added to the solution and stirred at about 120° C. for about 18 hours. After completion of the reaction, toluene was removed by distillation in a reduced pressure, followed by an addition of 50.0 mL of distilled water and extraction three times each with 70.0 mL of methylene chloride. The organic phase was collected, and was dried using magnesium sulfate and the solvent was evaporated. The residue was separated and purified using silica gel column chromatography to obtain 9.8 g (41.65 mmol) of Intermediate 1-a (Yield: 92.9%). This compound was identified using liquid chromatography-mass spectroscopy (LC-MS). C16H13NO: M+ 236.10

Synthesis of Intermediate 1-b

After 8.0 g (34.00 mmol) of Intermediate 1-a was dissolved in 80 mL of dichloromethane, 6.1 mL (36.26 mmol) of trifluoromethanesulfonic anhydride and 5.7 mL (40.87 mmol) of triethyl amine were added to the solution and stirred for about 4 hours. After completion of the reaction, 20.0 mL of distilled water was added to stop the reaction. After extraction three times each with 50.0 mL of methylene chloride, the organic phase was collected and was dried using magnesium sulfate and the solvent was evaporated. The residue was separated and purified by silica gel column chromatography to obtain 11.5 g (31.31 mmol) of Intermediate 1-b (Yield: 92.1%). This compound was identified using LC-MS. C17H12F3NO3S: M+ 368.05

Synthesis of Intermediate 1-c

After 10.2 mL (20.43 mmol) of lithium diisopropyl amide (LDA, 2M Solution in Et$_2$O) was diluted with 30.0 mL of diethylether in a flask filled with nitrogen, the temperature was lowered to about −78° C. A solution of 5.0 g (13.62 mmol) of the Intermediate 1-b dissolved in 20.0 mL of diethylether was slowly dropwise added into the flask for about 15 minutes and stirred for about 1 hour. 3.7 mL (16.35 mmol) of triisopropylborate was slowly dropwise added to the solution and stirred at room temperature for about 1 hour. After completion of the reaction, 50 mL of an aqueous 5% NaOH solution was slowly added thereto. After a pH adjustment to about 1-2 by an addition of 80 mL of a 3N HCl solution, and extraction three times each with 50.0 mL of ethylacetate, the organic phase was collected and was dried using magnesium sulfate and the solvent was evaporated. The residue was separated and purified by silica gel column chromatography to obtain 1.5 g (3.65 mmol) of Intermediate 1-c (Yield: 26.8%). This compound was identified using LC-MS. C17H13BF3NO5S: M+ 412.07

Synthesis of Intermediate 1-d 4.5 g (12.23 mmol) of the Intermediate 1-b, and 1.8 g (14.67 mmol) of potassium bromide (KBr) were added to 40.0 mL of a mixed acid solution (nitric acid:sulfuric acid=1:2) and vigorously stirred at about 100° C. for about 24 hours. After completion of the reaction, 200.0 mL of water was added to the mixture, followed by a pH adjustment to about 7 using an aqueous NaOH solution. The resulting solid was filtrated and washed with dichloromethane. After extraction three times each with 80.0 mL of dichloromethane, the organic phase was collected and was dried using magnesium sulfate and the solvent was evaporated. The residue was separated and purified by silica gel column chromatography to obtain 1.23 g (2.76 mmol) of Intermediate 1-d (Yield: 22.5%). This compound was identified using LC-MS. C17H11BrF3NO3S: M+ 445.99

Synthesis of Compound 1

2.0 g (4.86 mmol) of the Intermediate 1-c and 1.8 g (4.05 mmol) of the Intermediate 1-d were dissolved in 35.0 mL of tetrahydrofuran (THF). 234.2 mg (0.20 mmol) of Pd(PPh3)$_4$ and 5.0 mL of an aqueous 5% K$_2$CO$_3$ solution (by weight) were added to the solution and stirred at about 120° C. for about 24 hours under reflux. After completion of the reaction, the temperature was cooled to room temperature, and 20.0 mL of water was added to stop the reaction. After extraction three times each with 70.0 mL of ethylacetate, the organic phase was collected and was dried using magnesium sulfate and the solvent was evaporated. The residue was separated and purified by silica gel column chromatography to obtain 0.83 g (1.92 mmol) of Compound 1 (Yield: 39.5%). This compound was identified using LC-MS. C32H20N2: M+ 433.16

Synthesis Example 2

Synthesis of Compound 14

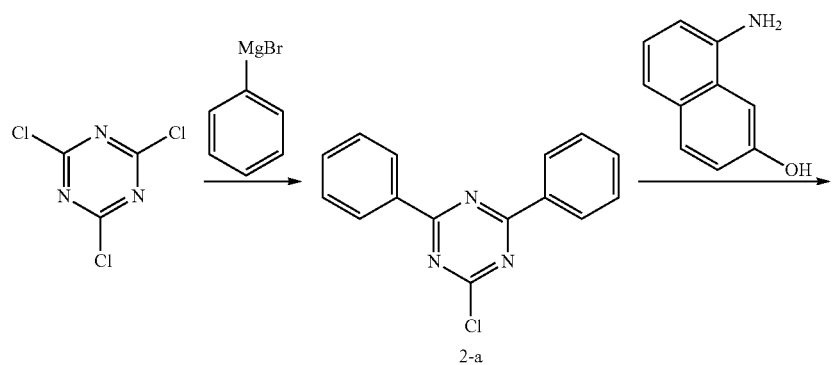

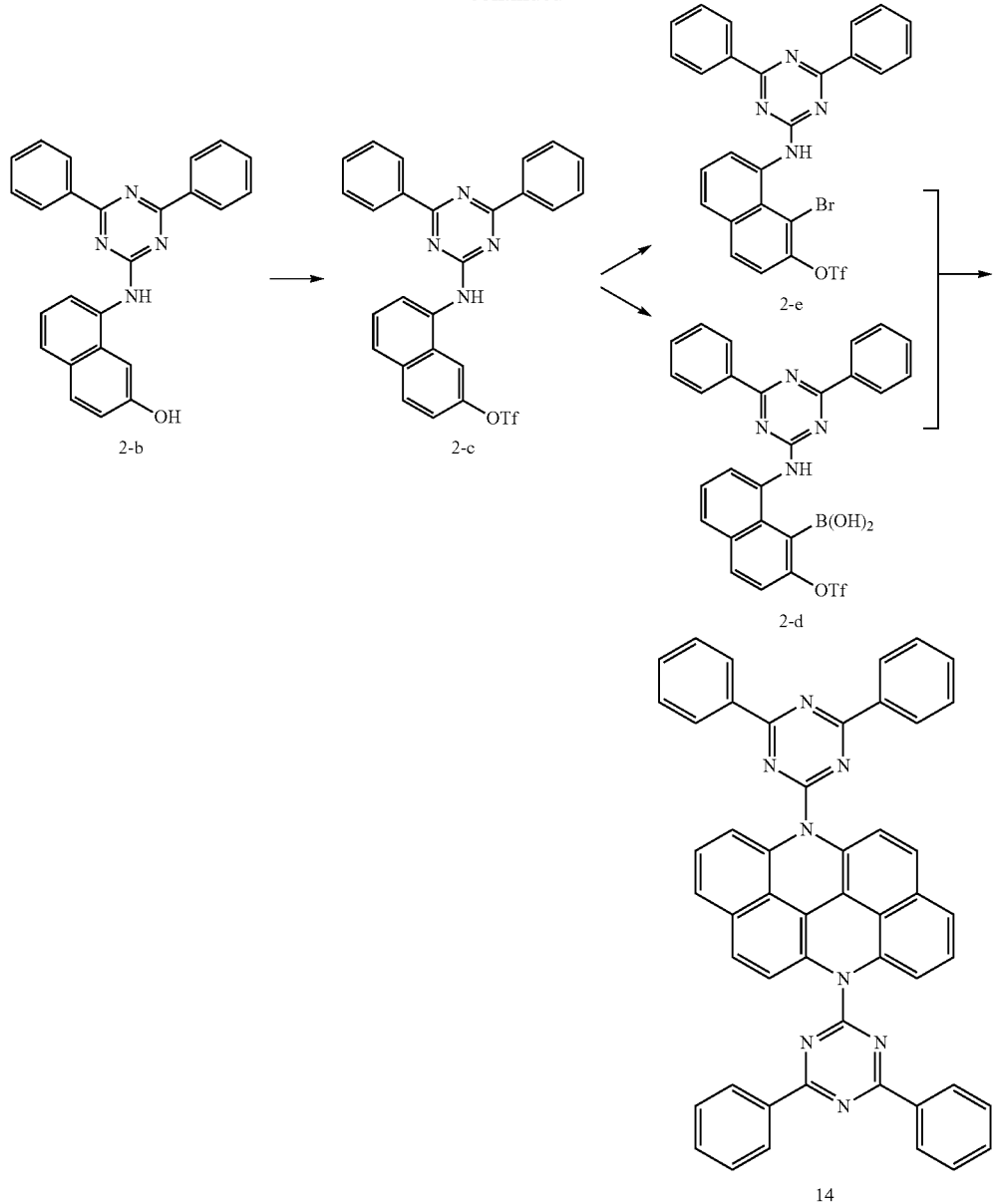

Synthesis of Intermediate 2-a 10.0 g (54.22 mmol) of cyanuric chloride was dissolved in 35 mL of tetrahydrofuran (THF), and the solution was cooled to 0° C. 45.1 mL (135.56 mmol) of phenyl magnesium bromide (3.0M in diethylether) was slowly added to the solution and stirred at room temperature for about 3 hours. The resulting solid was filtrated in a reduced pressure and washed with methanol and hexane to obtain 9.0 g of (33.62 mmol) of Intermediate 2-a (Yield: 62.0%). This compound was identified using LC-MS. C15H10ClN3: M+ 268.06

Synthesis of Intermediate 2-b

After 10.0 g (62.82 mmol) of 8-amino-2-naphthol was dissolved in 100 mL of toluene, 20.2 g (75.38 mmol) of the Intermediate 2-a, 9.1 g (94.23 mmol) of sodium tert-butoxide and 4.6 g (5.03 mmol) of tris(dibenzylideneacetone)dipalladium(0) were added to the solution and stirred at about 120° C. for about 18 hours. After completion of the reaction, toluene was removed by distillation in a reduced pressure, followed by an addition of 50.0 mL of distilled water and extraction three times each with 70.0 mL of methylene chloride. The organic phase was collected, and was dried using magnesium sulfate and the solvent was evaporated. The residue was separated and purified using silica gel column chromatography to obtain 24.8 g (57.1 mmol) of Intermediate 2-b (Yield: 90.9%). This compound was identified using LC-MS. C25H18N4O: M+ 390.15

Synthesis of Intermediate 2-c

After 12.0 g (27.62 mmol) of Intermediate 2-b was dissolved in 80 mL of dichloromethane, 5.4 mL (32.27 mmol) of trifluoromethanesulfonic anhydride and 5.1 mL (36.88 mmol) of triethylamine were added to the solution and stirred for about 4 hours. After completion of the reaction, 20.0 mL of distilled water was added to stop the reaction. After extraction three times each with 50.0 mL of methylene chloride, the organic phase was collected and was dried using magnesium sulfate and the solvent was evaporated. The residue was separated and purified by silica gel column chromatography to obtain 14.2 g (27.18 mmol) of Intermediate 2-c (Yield: 88.4%). This compound was identified using LC-MS. C26H17F3N4O3S: M+ 523.10

Synthesis of Intermediate 2-d

After 5.02 mL (10.1 mmol) of lithium diisopropyl amide (LDA, 2M solution in $Et_2O$) was diluted with 30.0 mL of diethylether in a flask filled with nitrogen, the temperature was lowered to about −78° C. A solution of 3.50 g (6.7 mmol) of the Intermediate 2-c dissolved in 20.0 mL of diethylether was slowly dropwise added into the flask for about 15 minutes and stirred for about 1 hour. 1.86 mL (8.00 mmol) of triisopropylborate was slowly dropwise added to the solution and stirred at room temperature for about 1 hour. After completion of the reaction, 50 mL of an aqueous 5% NaOH solution was slowly added thereto. After a pH adjustment to about 1 to 2 by an addition of 80 mL of a 3N HCl solution, and extraction three times each with 70.0 mL of ethylacetate, the organic phase was collected and was dried using magnesium sulfate and the solvent was evaporated. The residue was separated and purified by silica gel column chromatography to obtain 1.2 g (2.12 mmol) of Intermediate 2-d (Yield: 31.6%). This compound was identified using LC-MS. C26H18BF3N4O5S: M+ 567.10

Synthesis of Intermediate 2-e 4.5 g (8.61 mmol) of the Intermediate 2-c, and 1.8 g (10.33 mmol) of potassium bromide (KBr) were added to 40.0 mL of a mixed acid solution (nitric acid:sulfuric acid=1:2) and vigorously stirred at about 100° C. for about 24 hours. After completion of the reaction, 200.0 mL of water was added to the mixture, followed by a pH adjustment to about 7 using an aqueous NaOH solution. The resulting solid was filtrated and washed with dichloromethane. After extraction three times each with 80.0 mL of dichloromethane, the organic phase was collected and was dried using magnesium sulfate and the solvent was evaporated. The residue was separated and purified by silica gel column chromatography to obtain 1.1 g (1.75 mmol) of Intermediate 2-e (Yield: 20.3%). This compound was identified using LC-MS. C26H16BrF3N4O3S: M+ 601.32

Synthesis of Compound 14

Tdhfjv 1.0 g (1.77 mmol) of the Intermediate 2-d and 0.9 g (1.47 mmol) of the Intermediate 2-e were dissolved in 20.0 mL of tetrahydrofuran (THF). 85.0 mg (0.07 mmol) of Pd(PPh3)4 and 5.0 mL of an aqueous 5% $K_2CO_3$ solution (by weight) were added to the solution and stirred at about 120° C. for about 24 hours under reflux. After completion of the reaction, the temperature was cooled to room temperature, and 30.0 mL of water was added to stop the reaction. After extraction three times each with 40.0 mL of ethylacetate, the organic phase was collected and was dried using magnesium sulfate and the solvent was evaporated. The residue was separated and purified by silica gel column chromatography to obtain 0.22 mg (0.51 mmol) of Compound 14 (Yield: 28.8%). This compound was identified using LC-MS. C50H30N8: M+ 743.00

Synthesis Example 3

Synthesis of Compound 24

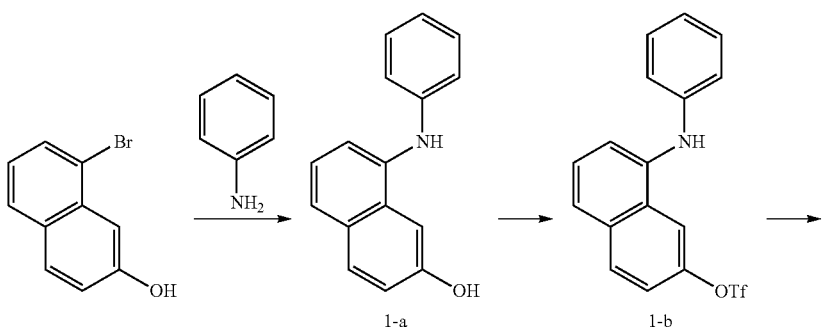

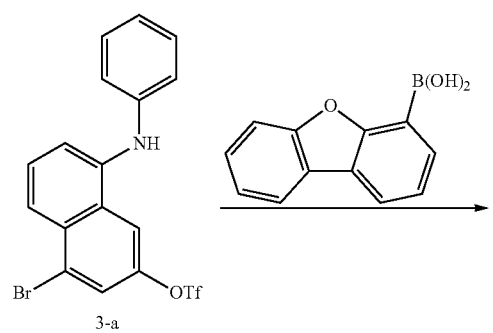

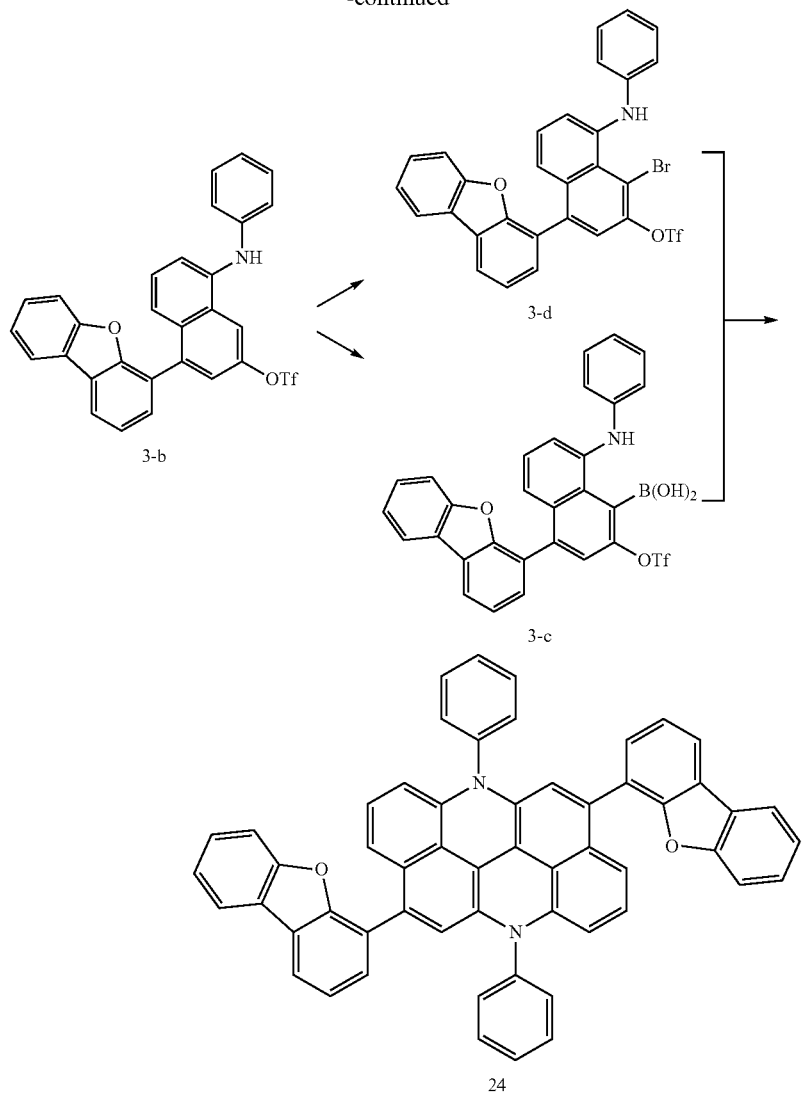

Synthesis of Intermediate 3-a

After 4.5 g (12.25 mmol) of Intermediate 1-b was dissolved in 50 mL of chloroform to obtain a solution, a dilution of 0.7 mL (13.48 mmol) of bromine ($Br_2$) with 5.0 mL of chloroform was slowly dropwise added to the solution for about 10 minutes and stirred at room temperature overnight. The solvent was distilled in a reduced pressure, and the residue was recrystallized using ethylacetate/hexane. The resulting solid was filtrated and dried to obtain 1.1 g (2.35 mmol) of an Intermediate 3-a (Yield: 19.2%). This compound was identified LC-MS. $C_{17}H_{13}BF_3NO_5S$: M+ 445.96

Synthesis of Intermediate 3-b 1.4 g (6.72 mmol) of dibenzofurane boronic acid and 2.0 g (4.48 mmol) of the Intermediate 3-a were dissolved in 30.0 mL of tetrahydrofuran (THF). 260.2 mg (0.22 mmol) of $Pd(PPh3)_4$ and 1.9 g (13.45 mmol) of $K_2CO_3$ were added to the solution and stirred at about 120° C. for about 24 hours under reflux. After completion of the reaction, the temperature was cooled to room temperature, and 50.0 mL of water was added to stop the reaction. After extraction three times each with 70.0 mL of ethylacetate, the organic phase was collected and was dried using magnesium sulfate and the solvent was evaporated. The residue was separated and purified by silica gel column chromatography to obtain 1.2 g (2.25 mmol) of Intermediate 3-b (Yield: 50.2%). This compound was identified using LC-MS. $C_{29}H_{18}F_3NO_4S$: M+ 534.09

Synthesis of Intermediate 3-c

After 4.2 mL (8.43 mmol) of lithium diisopropyl amide (LDA, 2M solution in $Et_2O$) was diluted with 40.0 mL of diethylether in a flask filled with nitrogen, the temperature was lowered to about −78° C. A solution of 3.0 g (5.62 mmol) of the Intermediate 3-b dissolved in 10.0 mL of diethylether was slowly dropwise added into the flask for about 15 minutes and stirred for about 1 hour. 1.56 mL (6.75 mmol) of triisopropylborate was slowly dropwise added to the solution and stirred at room temperature for about 1 hour. After completion of the reaction, 50 mL of an aqueous 5% NaOH solution was slowly added thereto. After a pH adjustment to about 1 to 2 by an addition of 80.0 mL of a 3N HCl solution, and extraction three times each with 50.0 mL of ethylacetate, the organic phase was collected and was dried using magnesium sulfate and the solvent was evaporated. The residue was separated and purified by silica gel column chromatography to obtain 1.1 g (1.91 mmol) of Intermediate 3-c (Yield: 33.9%). This compound was identified using LC-MS. C29H19BF3NO6S: M+ 578.10

Synthesis of Intermediate 3-d 3.0 g (5.62 mmol) of the Intermediate 3-b, and 1.8 g (6.75 mmol) of potassium bromide (KBr) were added to 27.0 mL of a mixed acid solution (nitric acid:sulfuric acid=1:2) and vigorously stirred at about 100° C. for about 24 hours. After completion of the reaction, 250.0 mL of water was added to the mixture, followed by a pH adjustment to about 7 using an aqueous NaOH solution. The resulting solid was filtrated and washed with dichloromethane. After extraction three times each with 70.0 mL of dichloromethane, the organic phase was collected and was dried using magnesium sulfate and the solvent was evaporated. The residue was separated and purified by silica gel column chromatography to obtain 1.1 g (1.71 mmol) of Intermediate 3-d (Yield: 30.5%). This compound was identified using LC-MS. C29H17BrF3NO4S: M+ 612.00

Synthesis of Compound 24

1.5 g (2.60 mmol) of the Intermediate 3-c and 1.3 g (2.17 mmol) of the Intermediate 3-d were dissolved in 40.0 mL of tetrahydrofuran (THF). 125.1 mg (0.11 mmol) of Pd(PPh3)4 and 8.0 mL of an aqueous 5% K2CO3 solution (by weight) were added to the solution and stirred at about 120° C. for about 24 hours under reflux. After completion of the reaction, the temperature was cooled to room temperature, and 30.0 mL of water was added to stop the reaction. After extraction three times each with 50.0 mL of ethylacetate, the organic phase was collected and was dried using magnesium sulfate and the solvent was evaporated. The residue was separated and purified by silica gel column chromatography to obtain 730 mg (0.95 mmol) of Compound 24 (Yield: 36.7%). This compound was identified using liquid LC-MS. C56H32N2O2: M+ 765.25

Synthesis Example 4

Synthesis of Compound 70

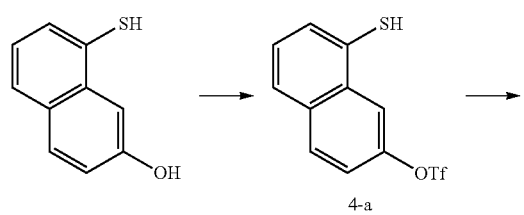

4-a

Synthesis of Intermediate 4-a

After 8.0 g (45.40 mmol) of 8-mercapto-naphthalene-2-ol was dissolved in 80 mL of dichloromethane, 8.0 mL (47.66 mmol) of trifluoromethanesulfonic anhydride and 7.6 mL (54.47 mmol) of triethyl amine were added to the solution and stirred for about 4 hours. After completion of the reaction, 20.0 mL of distilled water was added to stop the reaction. After extraction three times each with 60.0 mL of methylene chloride, the organic phase was collected and was dried using magnesium sulfate and the solvent was evaporated. The residue was separated and purified by silica gel column chroma-

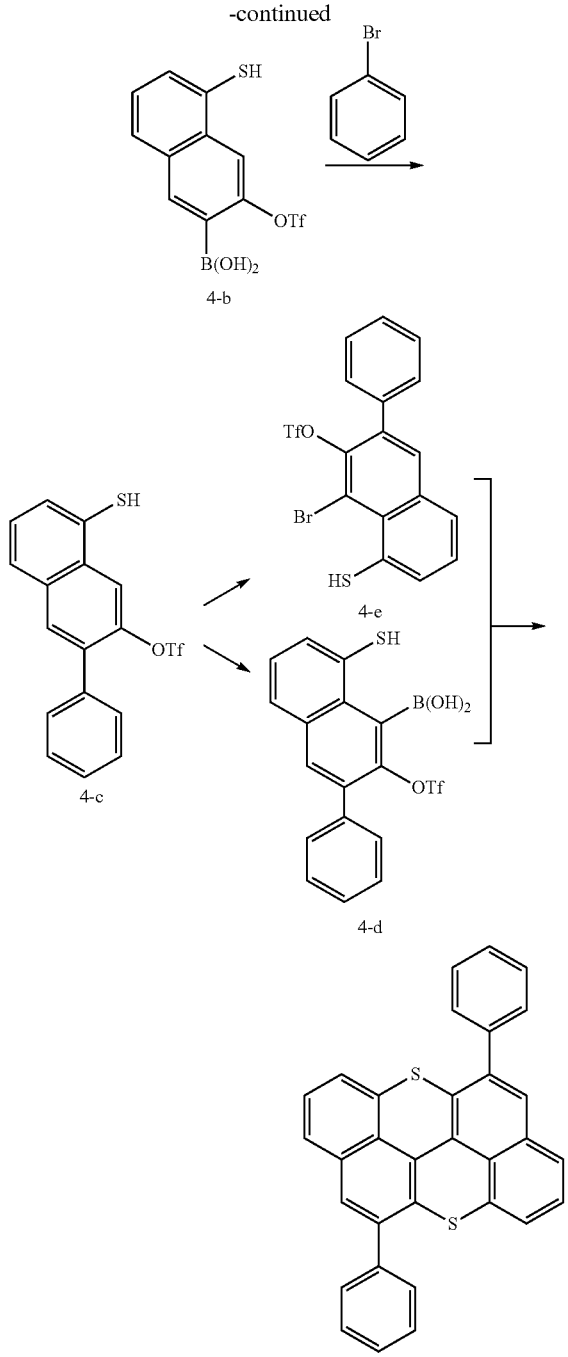

70 tography to obtain 12.5 g (40.54 mmol) of Intermediate 4-a (Yield: 89.3%). This compound was identified using LC-MS. C11H7F3O3S2: M+ 308.99

Synthesis of Intermediate 4-b

After 8.5 mL (17.03 mmol) of lithium diisopropyl amide (LDA, 2M solution in Et$_2$O) was diluted with 35.0 mL of diethylether in a flask filled with nitrogen, the temperature was lowered to about −78° C. A solution of 3.5 g (11.35 mmol) of the Intermediate 4-a dissolved in 30.0 mL of diethylether was slowly dropwise added into the flask for about 15 minutes and stirred for about 1 hour. 3.7 mL (13.62 mmol) of triisopropylborate was slowly dropwise added to the solution and stirred at room temperature for about 1 hour. After completion of the reaction, 80.0 mL of an aqueous 5% NaOH solution was slowly added thereto. After a pH adjustment to about 1 to 2 by an addition of 120.0 mL of a 3N HCl solution, and extraction three times each with 80.0 mL of ethylacetate, the organic phase was collected and was dried using magnesium sulfate and the solvent was evaporated. The residue was separated and purified by silica gel column chromatography to obtain 1.1 g (3.12 mmol) of Intermediate 4-b (Yield: 27.5%). This compound was identified using LC-MS. C11H8BF3O5S2: M+ 352.99

Synthesis of Intermediate 4-c 6.8 g (19.24 mmol) of the Intermediate 4-b and 2.0 g (12.82 mmol) of benzene bromide were dissolved in 100.0 mL of tetrahydrofuran (THF). 740 mg (0.64 mmol) of Pd(PPh3)$_4$ and 5.3 g (38.47 mmol) of K$_2$CO$_3$ were added to the solution and stirred at about 120° C. for about 24 hours under reflux. After completion of the reaction, the temperature was cooled to room temperature, and 80.0 mL of water was added to stop the reaction. After extraction three times each with 100.0 mL of ethylacetate, the organic phase was collected and was dried using magnesium sulfate and the solvent was evaporated. The residue was separated and purified by silica gel column chromatography to obtain 2.8 g (7.28 mmol) of Intermediate 4-c (Yield: 56.8%). This compound was identified using LC-MS. C17H11F3O3S2: M+ 385.01

Synthesis of Intermediate 4-d

After 6.8 mL (13.66 mmol) of lithium diisopropyl amide (LDA, 2M solution in Et$_2$O) was diluted with 50.0 mL of diethylether in a flask filled with nitrogen, the temperature was lowered to about −78° C. A solution of 3.5 g (9.11 mmol) of the Intermediate 4-c dissolved in 25.0 mL of diethylether was slowly dropwise added into the flask for about 15 minutes and stirred for about 1 hour. 2.5 mL (10.93 mmol) of triisopropylborate was slowly dropwise added to the solution and stirred at room temperature for about 1 hour. After completion of the reaction, 80.0 mL of an aqueous 5% NaOH solution was slowly added thereto. After a pH adjustment to about 1 to 2 by an addition of 120.0 mL of a 3N HCl solution, and extraction three times each with 80.0 mL of ethylacetate, the organic phase was collected and was dried using magnesium sulfate and the solvent was evaporated. The residue was separated and purified by silica gel column chromatography to obtain 1.5 g (3.48 mmol) of Intermediate 4-d (Yield: 38.2%). This compound was identified using LC-MS. C17H12BF3O5S2: M+ 429.01

Synthesis of Intermediate 4-e 3.5 g (9.11 mmol) of the Intermediate 4-c, and 1.3 g (10.93 mmol) of potassium bromide (KBr) were added to 32.0 mL of a mixed acid solution (nitric acid:sulfuric acid=1:2) and vigorously stirred at about 100° C. for about 24 hours. After completion of the reaction, 160.0 mL of water was added to the mixture, followed by a pH adjustment to about 7 using an aqueous NaOH solution. The resulting solid was filtrated and washed with dichloromethane. After extraction three times each with 80.0 mL of dichloromethane, the organic phase was collected and was dried using magnesium sulfate and the solvent was evaporated. The residue was separated and purified by silica gel column chromatography to obtain 1.2 g (2.59 mmol) of Intermediate 4-e (Yield: 28.5%). This compound was identified using LC-MS. C17H10BrF3O3S2: M+ 462.95

Synthesis of Compound 70

1.5 g (3.50 mmol) or the Intermediate 4-d and 1.4 g (2.92 mmol) of the Intermediate 4-e were dissolved in 30.0 mL of tetrahydrofuran (THF). 168.7 mg (0.15 mmol) of Pd(PPh3)$_4$ and 5.0 mL of an aqueous 5% K$_2$CO$_3$ solution (by weight) were added to the solution and stirred at about 120° C. for about 24 hours under reflux. After completion of the reaction, the temperature was cooled to room temperature, and 30.0 mL of water was added to stop the reaction. After extraction three times each with 80.0 mL of ethylacetate, the organic phase was collected and was dried using magnesium sulfate and the solvent was evaporated. The residue was separated and purified by silica gel column chromatography to obtain 0.73 g (1.56 mmol) of Compound 70 (Yield: 44.7%). This compound was identified using LC-MS. C32H18S2: M+ 467.05

Synthesis Example 5

Synthesis of Compound 83

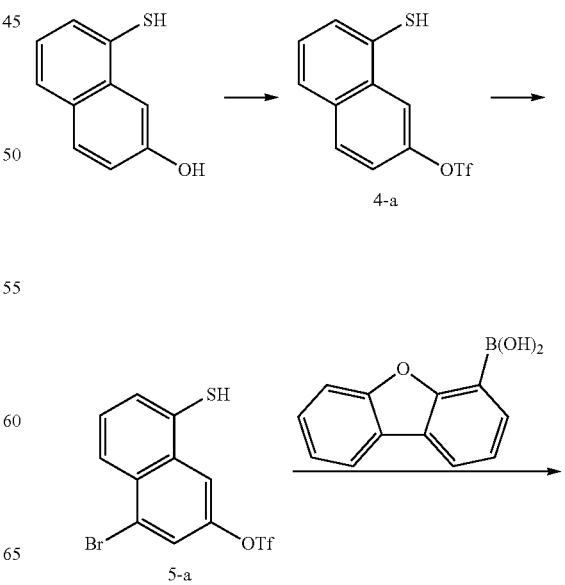

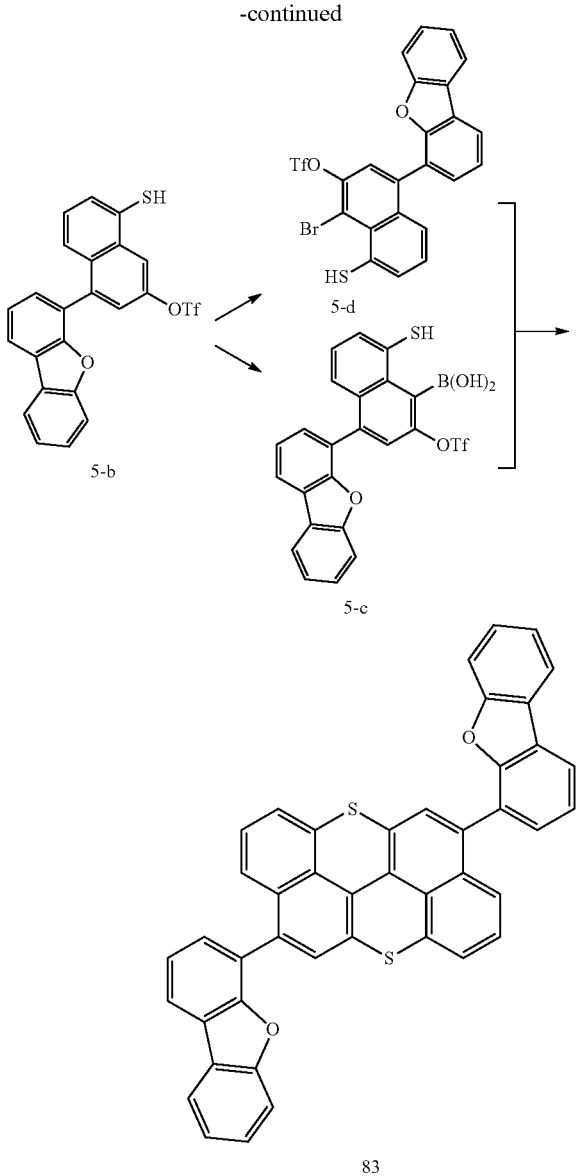

Synthesis of Intermediate 5-a

After 5.0 g (16.22 mmol) of Intermediate 4-a was dissolved in 35.0 mL of chloroform to obtain a solution, a dilution of 0.9 mL (17.84 mmol) of bromine ($Br_2$) with 15.0 mL of chloroform was slowly dropwise added to the solution for about 10 minutes and stirred at room temperature overnight. The solvent was distilled in a reduced pressure, and the residue was recrystallized using ethylacetate/hexane. The resulting solid was filtrated and dried to obtain 1.3 g (3.36 mmol) of an Intermediate 5-a (Yield: 20.1%). This compound was identified using LC-MS. C11H6BrF3O3S2: M+ 386.85

Synthesis of Intermediate 5-b 4.1 g (19.37 mmol) of dibenzofurane boronic acid and 5.0 g (12.91 mmol) of the Intermediate 5-a were dissolved in 80.0 mL of tetrahydrofuran (THF). 750 mg (0.65 mmol) of Pd(PPh3)$_4$ and 5.4 g of $K_2CO_3$ were added to the solution and stirred at about 120° C. for about 24 hours under reflux. After completion of the reaction, the temperature was cooled to room temperature, and 30.0 mL of water was added to stop the reaction. After extraction three times each with 80.0 mL of ethylacetate, the organic phase was collected and was dried using magnesium sulfate and the solvent was evaporated. The residue was separated and purified by silica gel column chromatography to obtain 2.8 g (5.90 mmol) of Intermediate 5-b (Yield: 45.7%). This compound was identified using LC-MS. C23H13F3O4S2: M+474.47

Synthesis of Intermediate 5-c

After 5.5 mL (11.06 mmol) of lithium diisopropyl amide (LDA, 2M solution in $Et_2O$) was diluted with 50.0 mL of diethylether in a flask filled with nitrogen, the temperature was lowered to about −78° C. A solution of 3.5 g (7.38 mmol) of the Intermediate 5-b dissolved in 20.0 mL of diethylether was slowly dropwise added into the flask for about 15 minutes and stirred for about 1 hour. 2.5 mL (8.85 mmol) of triisopropylborate was slowly dropwise added to the solution and stirred at room temperature for about 1 hour. After completion of the reaction, 65.0 mL of an aqueous 5% NaOH solution was slowly added thereto. After a pH adjustment to about 1 to 2 by an addition of 89.0 mL of a 3N HCl solution, and extraction three times each with 90.0 mL of ethylacetate, the organic phase was collected and was dried using magnesium sulfate and the solvent was evaporated. The residue was separated and purified by silica gel column chromatography to obtain 1.7 g (3.28 mmol) of Intermediate 5-c (Yield: 44.5%). This compound was identified using LC-MS. C23H14BF3O6S2: M+ 519.02

Synthesis of Intermediate 5-d 3.5 g (7.38 mmol) of the Intermediate 5-b, and 1.1 g (8.85 mmol) of potassium bromide (KBr) were added to 31.5 mL of a mixed acid solution (nitric acid:sulfuric acid=1:2) and vigorously stirred at about 100° C. for about 24 hours. After completion of the reaction, 158.0 mL of water was added to the mixture, followed by a pH adjustment to about 7 using an aqueous NaOH solution. The resulting solid was filtrated and washed with dichloromethane. After extraction three times each with 70.0 mL of dichloromethane, the organic phase was collected and was dried using magnesium sulfate and the solvent was evaporated. The residue was separated and purified by silica gel column chromatography to obtain 1.1 g (2.01 mmol) of Intermediate 5-d (Yield: 27.2%). This compound was identified using LC-MS. C23H12BrF3O4S2: M+ 552.95

Synthesis of Compound 83

1.5 g (2.89 mmol) of the Intermediate 5-c and 1.33 g (2.41 mmol) of the Intermediate 5-d were dissolved in 50.0 mL of tetrahydrofuran (THF). 139.3 mg (0.12 mmol) of Pd(PPh3)$_4$ and 8.0 mL of an aqueous 5% $K_2CO_3$ solution (by weight) were added to the solution and stirred at about 120° C. for about 24 hours under reflux. After completion of the reaction, the temperature was cooled to room temperature, and 50.0 mL of water was added to stop the reaction. After extraction three times each with 70.0 mL of ethylacetate, the organic phase was collected and was dried using magnesium sulfate and the solvent was evaporated. The residue was separated and purified by silica gel column chromatography to obtain 0.8 g (1.27 mmol) of Compound 83 (Yield: 44.0%). This compound was identified using LC-MS. C44H22O2S2: M+ 647.10

Other compounds were further synthesized using the substituents of I Group to VI groups above based on the equivalents and methods described in the above synthesis examples.

LC-MS and NMR results of these compounds are summarized in the following table.

| No. | LC-MS | $^1$H NMR (CD$_2$Cl$_2$, 300 MHz) |
|---|---|---|
| 1 | C$_{32}$H$_{20}$N$_2$<br>M+ 433.20 | • • • • 7.39 (m, 2H), 7.42~7.61 (m, 4H), 7.82 (d, 2H, J = 7.79), 7.86~7.85 (m, 6H), 7.96 (d, 2H, J = 8.02), 8.01 (dd, 2H, J = 8.32) |
| 2 | C$_{40}$H$_{24}$N$_2$<br>M+ 532.21 | • = 7.41 (d, 1H, J = 8.23), 7.53 (d, 1H, J = 8.00), 7.60 (dd, 2H, J = 8.21), 7.70 (dd, 2H, J = 9.37), 7.91 (dd, 2H, J = 2.43), 7.93 (d, 1H, J = 8.01), 7.95 (d, 1H, J = 2.51), 8.00~8.09 (m, 6H), 8.12 (dd, 2H, J = 8.37), 8.23~8.26 (m, 4H) |
| 3 | C$_{44}$H$_{28}$N$_2$<br>M+ 585.24 | • • = 7.41~7.50 (m, 2H), 7.59~7.63 (m, 2H), 7.65~7.79 (m, 10H), 7.96~8.04 (m, 4H), 8.08~8.32 (m, 10H) |
| 4 | C$_{44}$H$_{28}$N$_2$<br>M+ 585.24 | • • 7.41 (dd, 2H, J = 8.33), 7.49~7.70 (m, 10H), 7.82 (dd, 2H, J = 8.14), 7.85~7.92 (m, 4H), 7.92~7.96 (m, 4H), 8.01 (dd, 2H, J = 8.36), 8.08 (dd, 2H, J = 7.45), 8.23 (dd, 2H, J = 1.91) |
| 5 | C$_{30}$H$_{18}$N$_4$<br>M+ 435.17 | • = 6.99 (dd, 2H, J = 6.64), 7.54 (dd, 2H, J = 8.31), 7.79 (dd, 2H, J = 6.63), 7.91 (dd, 2H, J = 8.31), 7.97~8.00 (m, 6H), 8.47~8.51 (m, 4H) |
| 6 | C$_{30}$H$_{18}$N$_4$<br>M+ 435.19 | • = 7.60~7.61 (m, 4H), 7.91~7.99 (m, 8H), 8.06 (dd, 2H, J = 8.37), 8.36 (d, 2H, J = 2.51), 9.29 (d, 2H, J = 5.42) |
| 7 | C$_{28}$H$_{16}$N$_2$S$_2$<br>M+ 445.11 | • • = 7.31 (d, 2H, J = 1.73), 7.55 (dd, 2H, J = 8.54), 7.68 (dd, 2H, J = 6.42), 7.81~7.85 (m, 4H), 7.95 (dd, 2H, J = 8.32), 8.06~8.07 (m, 4H) |
| 8 | C$_{28}$H$_{16}$N$_2$O$_2$<br>M+ 413.14 | • • = 7.11 (d, 2H, J = 1.72), 7.58~7.60 (m, 4H), 7.83~7.86 (m, 6H), 8.06~8.07 (m, 4H) |
| 9 | C$_{30}$H$_{20}$N$_2$S$_2$<br>M+ 545.10 | • • = 7.27 (d, 1H, J = 7.85), 7.56~7.72 (m, 7H), 7.87 (dd, 2H, J = 2.21), 7.99~8.10 (m, 8H), 8.32 (dd, 2H, J = 7.48) |
| 10 | C$_{36}$H$_{20}$N$_2$O$_2$<br>M+ 513.17 | • • = 7.57~7.62 (m, 6H), 7.80 (dd, 2H, J = 6.62), 7.81~7.92 (m, 4H), 8.05~8.10 (m, 6H), 8.45 (d, 2H, J = 4.67) |
| 11 | C$_{38}$H$_{22}$N$_4$<br>M+ 535.20 | • • = 7.61~7.70 (m, 6H), 7.92 (d, 2H, J = 1.89), 8.01~8.14 (m, 10H), 8.28 (dd, 2H, J = 6.45), 9.51 (dd, 1H, J = 4.91), 9.61 (dd, 1H, J = 5.40) |
| 12 | C$_{50}$H$_{36}$N$_2$<br>M+ 665.190 | • = 2.08 (s, 6H), 7.12 (dd, 2H, J = 8.42), 7.29~7.32 (m, 4H), 7.41 (d, 1H, J = 8.47), 7.50 (dd, 2H, J = 1.75), 7.59 (d, 1H, J = 7.55), 7.73~7.76 (m, 4H), 7.81~7.83 (m, 2H), 7.90 (m, 4H), 7.97 (dd, 2H, J = 8.01), 8.04 (dd, 2H, J = 8.40) |
| 13 | C$_{56}$H$_{34}$N$_4$<br>M+ 763.31 | • • = 7.31 (dd, 1H, J = 7.52), 7.53 (t, 1H, J = 7.54), 7.57~7.64 (m, 6H), 7.75 (dd, 2H, J = 8.76), 7.81~7.90 (m, 8H), 8.17 (dd, 2H, J = 5.58), 8.23~8.26 (m, 4H), 8.30~8.36 (m, 6H), 8.52~8.58 (m, 4H) |
| 14 | C$_{50}$H$_{30}$N$_8$<br>M+ 743.29 | • • = 7.29 (m, 4H), 7.58 (dd, 2H, J = 7.57), 7.66~7.75 (m, 4H), 7.94~8.03 (m, 12H), 8.12~8.18 (m, 4H), 8.29~8.32 (m, 4H) |
| 15 | C$_{32}$H$_{10}$D$_{10}$N$_2$<br>M+ 443.22 | • • = 7.31~7.33 (m, 2H), 7.47~7.52 (m, 2H), 7.65~7.70 (m, 4H), 7.78~7.84 (m, 2H) |
| 16 | C$_{36}$H$_{28}$N$_2$O$_4$<br>M+ 553.22 | • • = 3.64 (s, 12H), 6.22 (dd, 2H, J = 1.81), 7.13 (dd, 2H, J = 1.81), 7.18 (dd, 2H, J = 1.82), 7.62 (dd, 2H, J = 8.67), 7.85~8.04 (m, 8H) |
| 17 | C$_{44}$H$_{28}$N$_2$<br>M+ 585.24 | • • = 7.41 (dd, 2H, J = 7.32), 7.52~7.68 (m, 14H), 7.85~8.08 (m, 10H), 8.20 (d, 2H, J = 8.23) |
| 18 | C$_{36}$H$_{28}$N$_2$<br>M+ 489.22 | • = 1.35 (t, 6H, J = 7.11), 4.62 (q, 4H, J = 7.10), 7.41 (dd, 2H, J = 1.73), 7.45~7.62 (m, 10H), 7.81~7.92 (m, 6H) |
| 19 | C$_{32}$H$_{10}$F$_{10}$N$_2$<br>M+ 613.10 | • • = 7.41 (t, 1H, J = 7.82), 7.59 (t, 1H, J = 7.51), 7.86 (d, 2H, J = 2.18), 7.91~8.02 (m, 6H), |
| 20 | C$_{34}$H$_{26}$N$_4$<br>M+ 491.23 | • • = 1.34 (t, 6H, J = 7.12), 4.59 (q, 4H, J = 7.10), 7.45 (dd, 2H, J = 8.75), 7.62 (q, 2H, J = 1.73), 7.76 (dd, 2H, J = 8.70), 7.85 (dd, 2H, J = 1.73), 7.92 (m, 2H), 8.10~8.19 (m, 4H), 8.50~8.55 (m, 2H) |
| 21 | C$_{40}$H$_{24}$N$_6$<br>M+ 589.20 | • • = 7.37~7.45 (m, 2H), 7.52 (dd, 2H, J = 8.23), 7.58~7.64 (m, 4H), 7.84 (dd, 2H, J = 8.22), 7.89~7.93 (m, 4H), 8.03 (dd, 2H, J = 1.74), 8.05~8.08 (m, 4H), 8.24 (dd, 2H, J = 8.23), 8.80 (dd, 2H, J = 1.99), 9.16 (dd, 2H, J = 1.99) |
| 22 | C$_{32}$H$_{24}$N$_2$S$_2$<br>M+ 502.15 | • • = 1.52 (t, 6H, J = 6.80), 4.59 (q, 4H, J = 6.81), 7.41 (dd, 2H, J = 9.35), 7.56~7.59 (m, 2H), 7.60~7.63 (m, 4H), 7.78 (dd, 2H, J = 6.24), 7.83 (dd, 2H, J = 1.98), 7.90 (dd, 2H, J = 1.82) |
| 23 | C$_{48}$H$_{32}$N$_2$S$_2$<br>M+ 701.22 | • • = 1.51 (t, 6H, J = 2.67), 4.88 (q, 4H, J = 2.66), 7.51 (t, 2H, J = 5.98), 7.75~7.86 (m, 8H), 7.95 (dd, 2H, J = 6.78), 8.24~8.35 (m, 6H), 8.38~8.41 (m, 2H), 8.49~8.53 (m, 2H) |
| 24 | C$_{56}$H$_{32}$N$_2$O$_2$<br>M+ 765.26 | • • = 7.53~7.64 (m, 6H), 7.85 (dd, 2H, J = 5.03), 7.86 (dd, 2H, J = 8.55), 7.88~7.93 (m, 2H), 7.96~8.21 (m, 12H), 8.34~8.37 (m, 2H), 8.45~8.50 (m, 4H), 8.59~8.68 (m, 2H) |
| 25 | C$_{36}$H$_{28}$N$_2$<br>M+ 489.24 | • • = 1.37 (t, 6H, J = 7.13), 4.77 (q, 4H, J = 7.11), 7.45 (dd, 2H, J = 9.10), 7.47 (t, 2H, J = 8.11), 7.53~7.63 (m, 8H), 7.70~7.74 (m, 2H), 7.76~7.79 (m, 2H), 7.83~7.88 (m, 2H) |
| 26 | C$_{56}$H$_{32}$N$_2$S$_2$<br>M+ 797.20 | • • = 7.56 (t, 2H, J = 6.31), 7.79 (dd, 2H, J = 8.45), 7.92~8.06 (m, 8H), 8.54 (dd, 2H, J-8.45), 8.72~8.82 (m, 4H), 8.90~9.09 (m, 6H), 9.15~9.31 (m, 8H) |
| 27 | C$_{54}$H$_{44}$N$_2$<br>M+ 721.37 | • • = 1.36 (t, 6H, J = 6.99), 2.11 (s, 12H), 5.17 (q, 4H, J = 6.99), 7.31~7.37 (m, 2H), 7.51~7.65 (m, 8H), 7.74~7.79 (m, 6H), 7.90~7.95 (m, 6H) |
| 28 | C$_{42}$H$_{26}$N$_4$<br>M+ 587.23 | • • = 7.40~7.44 (m, 2H), 7.51~7.60 (m, 6H), 7.71~7.79 (m, 2H), 7.84 (dd, 2H), J = 8.22), 7.89~7.93 (m, 4H), 7.99~8.08 (m, 6H), 8.63~8.66 (m, 2H), 9.13 (dd, 2H, J = 2.76) |

-continued

| No. | LC-MS | $^1$H NMR (CD$_2$Cl$_2$, 300 MHz) |
|---|---|---|
| 29 | C$_{60}$H$_{42}$N$_4$<br>M+ 818.36 | • • = 1.53 (t, 6H, J = 2.67), 5.28 (q, 4H, J = 2.67), 7.49~7.60 (m, 8H), 7.71 (dd, 2H, J = 7.22), 7.79~7.95 (m, 10H), 8.16~8.29 (m, 4H), 8.39~8.47 (m, 6H), 8.83 (dd, 2H, J = 4.77) |
| 30 | C$_{52}$H$_{32}$N$_6$<br>M+ 741.28 | • • = 7.11~7.18 (m, 1H), 7.31~7.42 (m, 3H), 7.58~7.60 (m, 4H), 7.61~7.63 (m, 2H), 7.82~7.86 (m, 4H), 7.91~8.06 (m, 10H), 8.09~8.12 (m, 2H), 8.18~8.21 (m, 2H), 8.28~8.30 (m, 2H), 9.75 (d, 2H, J = 1.99) |
| 31 | C$_{52}$H$_{32}$N$_6$<br>M+ 741.28 | • • = 7.26~7.34 (m, 5H), 7.57~7.64 (m, 4H), 7.83~7.95 (m, 5H), 8.06~8.16 (m, 10H), 8.28 (d, 2H, J = 1.51), 8.58 (d, 2H, J = 8.46), 8.84 (dd, 2H, J = 1.99), 9.03~9.07 (m, 2H) |
| 32 | C$_{44}$H$_{28}$N$_2$<br>M+ 585.24 | • • = 7.49~7.78 (m, 14H), 7.91 (dd, 2H, J = 8.02), 7.95 (dd, 2H, J = 2.23), 8.00~8.07 (m, 6H), 8.19~8.23 (m, 4H) |
| 33 | C$_{56}$H$_{32}$N$_2$O$_2$<br>M+ 765.23 | • • = 7.74~7.83 (m, 5H), 7.88~7.93 (m, 3H), 8.13~8.18 (m, 2H), 8.60 (dd, 2H, J = 5.04), 8.65~8.77 (m, 8H), 8.81~8.99 (m, 12H) |
| 34 | C$_{54}$H$_{34}$N$_4$<br>M+ 739.29 | • • = 7.54~7.61 (m, 2H), 7.74~7.80 (m, 4H), 7.87~7.93 (m, 8H), 8.07~8.09 (m, 2H), 8.12~8.17 (m, 6H), 8.23~8.29 (m, 2H), 8.32~8.36 (m, 6H), 8.40~8.46 (m, 2H), 8.50~8.57 (m, 2H) |
| 35 | C$_{42}$H$_{26}$N$_4$<br>M+ 587.23 | • • = 7.50~7.70 (m, 12H), 8.00~8.06 (m, 4H), 8.15 (dd, 2H, J = 8.44), 8.22~8.26 (m, 4H), 8.83~8.89 (m, 4H) |
| 36 | C$_{44}$H$_{28}$N$_2$<br>M+ 585.24 | • • = 7.51 (dd, 2H, J = 7.45), 7.54 (dd, 2H, J = 7.77), 7.60 (q, 4H, J = 8.15), 7.61~7.67 (m, 6H), 7.90 (dd, 2H, J = 8.15), 7.92~8.04 (m, 8H), 8.10 (dd, 2H, J = 8.49), 8.26 (dd, 2H, J = 8.48) |
| 37 | C$_{42}$H$_{26}$N$_4$<br>M+ 587.23 | • • = 7.50 (t, 1H, J = 7.79), 7.52 (t, 1H, J = 8.39), 7.55~7.64 (m, 4H), 7.87~7.94 (m, 4H), 7.98 (dd, 2H, J = 8.51), 8.09~8.13 (m, 2H), 8.18~8.24 (m, 5H), 8.5~8.29 (m, 2H), 8.37 (q, 2H, J = 8.49), 9.07~9.14 (m, 4H) |
| 38 | C$_{44}$H$_{32}$N$_2$<br>M+ 589.25 | • = 1.47 (t, 6H, J = 7.06), 4.63 (q, 4H, J = 7.05), 7.56 (dd, 2H, J = 6.75), 7.69~7.81 (m, 5H), 7.85 (dd, 1H, J = 6.58), 7.88 (dd, 1H, J = 6.57), 7.90 (dd, 2H, J = 7.18), 8.06~8.10 (m, 4H), 8.15~8.21 (m, 3H), 8.27~8.31 (m, 1H), 8.55~8.59 (m, 2H) |
| 39 | C$_{56}$H$_{28}$F$_4$N$_2$S$_2$<br>M+ 869.15 | • • = 7.32 (dd, 2H, J = 1.92), 7.71 (dd, 2H, J = 1.74), 7.78 (dd, 1H, J = 8.36), 7.83 (dd, 1H, J = 8.39), 8.01~8.14 (m, 6H), 8.32 (dd, 2H, J = 8.38), 8.61~8.65 (m, 2H), 8.70~8.75 (m, 4H), 8.92~8.98 (m, 4H), 9.05~9.10 (m, 4H) |
| 40 | C$_{52}$H$_{32}$N$_6$<br>M+ 741.23 | • • = 7.38 (dd, 3H, J = 7.83), 7.51~7.58 (m, 2H), 7.65 (dd, 1H, J = 8.40), 7.87 (dd, 2H, J = 6.78), 7.91~7.93 (m, 4H), 8.11 (dd, 2H, J = 5.25), 8.18~8.35 (m, 11H), 8.40 (dd, 1H, J = 6.21), 8.50 (dd, 2H, J = 6.92), 8.78~8.83 (m, 2H), 9.40~9.44 (m, 2H) |
| 41 | C$_{44}$H$_{28}$N$_2$<br>M+ 585.22 | • • = 7.30~7.34 (m, 2H), 7.60~7.73 (m, 12H), 7.89~7.97 (m, 8H), 8.01 (dd, 2H, J = 8.22), 8.06 (dd, 2H, J = 8.44), 8.22 (dd, 2H, J = 8.44) |
| 42 | C$_{44}$H$_{30}$N$_4$O$_2$<br>M+ 647.22 | • • = 3.80 (s, 6H), 7.03 (dd, 4H, J = 8.72), 7.69~7.78 (m, 4H), 7.81~7.90 (m, 3H), 7.94 (dd, 1H, J = 8.70), 7.96 (dd, 2H, J = 1.99), 7.98 (dd, 2H, J = 2.19), 8.05 (dd, 2H, J = 8.44), 8.26 (dd, 2H, J = 8.45), 8.45 (dd, 2H, J = 5.09), 9.35 (dd, 2H, J = 3.05) |
| 43 | C$_{48}$H$_{36}$N$_2$<br>M+ 641.30 | • • = 1.50 (t, 6H, J = 6.73), 4.60 (q, 4H, J = 6.73), 7.53~7.57 (m, 2H), 7.60~7.71 (m, 12H), 7.73~7.84 (m, 4H), 8.00~8.13 (m, 4H), 8.50~8.53 (m, 2H) |
| 44 | C$_{56}$H$_{38}$N$_4$<br>M+ 767.25 | • • = 6.88~6.92 (m, 8H), 7.19~7.39 (m, 16H), 7.53 (dd, 2H, J = 1.81), 7.55 (dd, 4H, J = 8.23), 7.82~7.96 (m, 8H) |
| 45 | C$_{56}$H$_{42}$N$_4$<br>M+ 771.30 | • • = 1.35 (t, 6H, J = 7.00), 4.54 (q, 4H, J = 7.00), 6.90~6.94 (m, 4H), 7.14 (dd, 1H, J = 8.23), 7.16 (dd, 1H, J = 8.22), 7.19~7.49 (m, 20H), 7.76~7.84 (m, 6H) |
| 46 | C$_{72}$H$_{48}$N$_6$<br>M+ 997.40 | • • = 6.59~6.93 (m 8H), 7.19~7.35 (m, 17H), 7.40~7.56 (m, 9H), 7.60 (dd, 2H, J = 8.40), 7.84~7.89 (m, 4H), 7.92~7.98 (m, 4H), 8.00~8.08 (m, 4H) |
| 47 | C$_{56}$H$_{34}$N$_4$<br>M+ 763.29 | • • = 7.29~7.33 (m, 1H), 7.53~7.66 (m, 13H), 7.88 (dd, 2H, J = 8.58), 8.02 (dd, 2H, J = 6.98), 8.11 (dd, 2H, J = 5.52), 8.19~8.28 (m, 12H), 8.50 (dd, 2H, J = 4.40) |
| 48 | C$_{37}$H$_{21}$N$_3$S<br>M+ 540.16 | • • = 7.48~7.52 (m, 1H), 7.60~7.63 (m, 1H), 7.69~7.84 (m, 4H), 7.99~8.26 (m, 12H), 8.33~8.35 (m, 1H), 8.42~8.45 (m, 1H), 8.69~8.73 (m, 1H) |
| 49 | C$_{44}$H$_{29}$N$_3$<br>M+ 600.24 | • • = 6.57~6.60 (m, 4H), 7.26~7.38 (m, 7H), 7.46~7.52 (m, 4H), 7.69 (dd, 2H, J = 7.93), 7.77 (dd, 1H, J = 8.66), 7.84~7.90 (m, 3H), 8.01 (dd, 2H, J = 8.45), 8.08 (dd, 2H, J = 7.88), 8.12~8.20 (m, 4H) |
| 50 | C$_{50}$H$_{29}$N$_3$S<br>M+ 704.21 | • • = 7.31~7.36 (m, 1H), 7.68~7.77 (m, 5H), 7.80~7.92 (m, 6H), 8.80 (dd, 1H, J = 5.54), 8.09~8.37 (m, 13H), 8.39 (dd, 1H, J = 5.34), 8.64~8.70 (m, 1H) |
| 51 | C$_{41}$H$_{25}$N$_5$<br>M+ 588.20 | • • = 7.44 (t, 1H, J = 7.78), 7.51 (dd, 1H, J = 8.23), 7.54 (dd, 1H, J = 8.23), 7.60~7.72 (m, 6H), 7.86~8.09 (m, 12H), 8.10~8.24 (m, 4H) |
| 52 | C$_{54}$H$_{34}$N$_4$<br>M+ 739.28 | • • = 7.48 (t, 2H, J = 7.43), 7.53 (dd, 2H, J = 8.55), 7.59~7.64 (m, 8H), 7.68~7.73 (m, 4H), 7.88 (dd, 2H, J = 7.89), 7.92 (dd, 2H, J = 8.00), 7.99 (dd, 2H, J = 1.76), 8.06~8.14 (m, 4H), 8.19~8.25 (m, 4H), 8.42~8.46 (m, 2H), 9.19~9.24 (m, 2H) |
| 53 | C$_{61}$H$_{37}$N$_5$<br>M+ 840.32 | • • = 7.35~7.41 (m, 2H), 7.65~7.70 (m, 1H), 7.74 (dd, 1H, J = 7.75), 7.80~8.01 (m, 11H), 8.05~8.09 (m, 6H), 8.12 (dd, 2H, J = 3.76), 8.20~8.25 (m, 4H), 8.28~8.30 (m, 2H), 8.46~8.50 (m, 2H), 8.55~8.58 (m, 1H), 8.66~8.71 (m, 3H), 8.83~8.85 (m, 1H), 9.49~9.52 (m, 1H) |

| No. | LC-MS | $^1$H NMR (CD$_2$Cl$_2$, 300 MHz) |
|---|---|---|
| 54 | C$_{53}$H$_{43}$N$_5$<br>M+ 750.35 | • • = 1.62 (s, 9H), 1.63 (s, 9H), 7.35~7.42 (m, 2H), 7.46~7.57 (m, 3H), 7.68~7.72 (m, 1H), 7.80~7.99 (m, 8H), 8.09~8.20 (m, 4H), 8.29~8.34 (m, 1H) 8.65~8.71 (m, 2H), 8.90~8.95 (m, 1H), 9.32~9.36 (m, 1H), 9.38 (dd, 1H, J = 5.04) |
| 55 | C$_{60}$H$_{40}$N$_2$S$_2$<br>M+ 853.24 | • • = 2.11 (t, 6H, J = 6.94), 4.82 (q, 4H, J = 6.93), 7.60~7.63 (m, 2H), 7.69~7.76 (m, 6H), 7.95~7.98 (m, 2H), 8.02~8.07 (m, 3H), 8.14~8.17 (m, 1H), 8.29~8.32 (m, 2H), 8.64 (dd, 2H, J = 5.47), 8.69 (dd, 2H, J = 5.00), 8.71~8.75 (m, 4H), 8.85 (d, 2H, J = 5.13), 9.02 (dd, 2H, J = 5.47), 9.09 (dd, 2H, J = 5.47) |
| 56 | C$_{43}$H$_{27}$N$_3$<br>M+ 586.22 | • = 7.39~7.45 (m, 2H), 7.47~7.52 (m, 1H), 7.58 (t, 1H, J = 8.02), 7.60~7.65 (m, 5H), 7.70~7.73 (m, 1H), 7.80~7.85 (m, 2H), 7.89~7.93 (m, 5H), 7.99~8.08 (m, 3H), 8.19~8.24 (m, 1H), 8.30 (q, 1H, J = 1.93), 8.36 (dd, 1H, J = 1.82), 8.62~8.65 (m, 1H) |
| 57 | C$_{46}$H$_{28}$N$_4$<br>M+ 637.24 | • = 7.29~7.37 (m, 2H), 7.52 (dd, 1H, J = 8.23), 7.56 (dd, 1H, J = 7.89), 7.58~7.72 (m, 5H), 7.82~7.86 (m, 2H), 7.90~7.92 (m, 1H), 7.93~7.95 (m, 3H), 7.98~8.03 (m, 1H), 8.06 (dd, 1H, J = 7.87), 8.09~8.14 (m, 1H), 8.17 (dd, 1H, J = 6.45), 8.20~8.25 (m, 3H), 8.28~8.33 (m, 3H), 8.43~8.45 (m, 1H), 8.51~8.55 (m, 1H) |
| 58 | C$_{40}$H$_{24}$N$_2$<br>M+ 533.19 | • • = 7.31~7.38 (m, 6H), 7.49 (dd, 2H, J = 8.82), 7.52 (dd, 2H, J = 8.47), 7.58~7.66 (m, 12H), 7.71~7.73 (m, 2H) |
| 59 | C$_{48}$H$_{34}$N$_4$<br>M+ 667.29 | • • = 1.64 (t, 6H, J = 2.67), 5.19 (q, 4H, J = 2.66), 7.30~7.35 (m, 2H), 7.53~7.55 (m, 2H), 7.58~7.65 (m, 4H), 7.70~7.77 (m, 2H), 7.82~7.84 (m, 1H), 7.91~8.06 (m, 9H), 8.32~8.38 (m, 4H) |
| 60 | C$_{38}$H$_{22}$N$_4$<br>M+ 535.20 | • • = 7.32~7.38 (m, 2H), 7.50~7.54 (m, 4H), 7.59~7.65 (m, 4H), 7.66 (dd, 1H, J = 7.80), 7.74 (dd, 1H, J = 7.80), 7.78~7.84 (m, 4H), 7.90~7.94 (m, 4H), 9.27~9.32 (m, 2H) |
| 61 | C$_{42}$H$_{24}$N$_2$O<br>M+ 573.20 | • • = 6.80~6.82 (m, 1H), 7.13~7.16 (m, 1H), 7.26~7.39 (m, 4H), 7.44~7.75 (m, 16H), 7.86 (dd, 1H, J = 8.83), 8.10~8.13 (m, 1H) |
| 62 | C$_{52}$H$_{32}$N$_2$<br>M+ 685.27 | • • = 7.19~7.24 (m, 2H), 7.31~7.34 (m, 2H), 7.38~7.42 (m, 2H), 7.46~7.69 (m, 16H), 7.75 (dd, 2H, J = 1.91), 7.79~7.84 (m, 4H), 7.94~7.98 (m 2H) |
| 63 | C$_{58}$H$_{34}$N$_4$<br>M+ 787.29 | • • = 7.19~7.21 (t, 1H, J = 7.83), 7.32~7.37 (m, 1H), 7.49~7.70 (m, 14H), 7.86~7.95 (m, 4H), 8.03~8.10 (m, 6H), 8.28~8.32 (m, 1H), 8.42 (dd, 2H, J = 5.64), 8.48 (dd, 2H, J = 5.64), 8.78~8.80 (m, 2H) |
| 64 | C$_{58}$H$_{40}$N$_6$<br>M+ 821.35 | • = 2.01 (t, 6H, J = 6.95), 5.30 (q, 4H, J = 6.95), 7.60~7.68 (m, 5H), 7.74~7.78 (m, 1H), 7.92~7.95 (m, 4H), 8.31~8.33 (m, 1H), 8.48~8.50 (m, 4H), 8.53~8.58 (m, 1H), 8.60~8.65 (m, 5H), 8.69 (dd, 1H, J = 5.28), 8.70 (dd, 1H, J = 5.26), 8.80~8.82 (m, 2H), 9.07~9.10 (m, 2H), 9.10~9.14 (m, 2H) |
| 65 | C$_{56}$H$_{40}$F$_2$N$_4$<br>M+ 807.34 | • = 1.07 (t, 6H, J = 7.03), 4.53 (q, 4H, J = 7.03), 6.97 (dd, 2H, J = 8.90), 7.00 (dd, 2H, J = 8.75), 7.16~7.36 (m, 22H), 7.58~7.64 (m, 4H) |
| 66 | C$_{58}$H$_{46}$N$_4$O$_2$<br>M+ 831.38 | • • = 1.39 (t, 6H, 7.11) 3.80 (s, 6H), 4.79 (q, 4H, J = 7.10), 6.46 (dd, 2H, J = 8.53), 6.99 (d, 1H, J = 8.42), 7.02 (d, 1H, J = 8.46), 7.17~7.30 (m, 15H), 7.37 (dd, 2H, J = 1.80), 7.56 (dd, 1H, J = 3.17), 7.57~7.62 (m, 6H), 7.95 (dd, 1H, J = 8.53), 8.13~8.16 (m, 1H) |
| 67 | C$_{46}$H$_{26}$N$_2$S<br>M+ 639.20 | • • = 7.33~7.38 (m, 3H), 7.48 (dd, 2H, J = 8.83), 7.50 (dd, 1H, J = 8.82), 7.53~7.69 (m, 14H), 7.73~7.79 (m, 3H), 7.84~7.89 (m, 1H), 8.06 (dd, 1H, J = 7.74), 8.12 (dd, 1H, J = 3.75) |
| 68 | C$_{64}$H$_{46}$N$_4$S$_2$<br>M+ 935.33 | • • = 1.76 (t, 6H, J = 6.80), 2.20 (t, 6H, J = 6.94), 5.10 (q, 4H, J = 6.94), 5.23 (q, 4H, J = 6.80), 8.08~8.14 (m, 3H), 8.41~8.43 (m, 2H), 8.47~8.51 (m, 3H), 8.56 (dd, 2H, J = 5.14), 8.66 (dd, 2H, J = 5.13), 8.69~8.8.86 (m, 11H), 8.92~8.95 (m, 3H), 9.04~9.10 (m, 2H) |
| 69 | C$_{48}$H$_{38}$N$_4$O$_2$<br>M+ 703.32 | • • = 1.54 (t, 6H, J = 2.67), 1.72 (t, 6H, J = 2.66), 4.90 (q, 4H, J = 2.67), 5.02 (q, 4H, J = 2.66), 6.84 (dd, 2H, J = 3.00), 6.92 (dd, 2H, J = 2.99), 7.44~7.51 (m, 4H), 7.70~7.77 (m, 4H), 7.87 (dd, 1H, J = 5.88), 8.05 (dd, 1H, J = 5.81), 8.19 (d, 1H, J = 5.21), 8.39 (d, 1H, J = 5.53), 8.47 (d, 1H, J = 4.08), 8.83 (d, 1H, J = 4.37) |
| 70 | C$_{32}$H$_{18}$S$_2$<br>M+ 467.08 | • • = 7.49 (t, 2H, J = 7.76), 7.67~7.80 (m, 8H), 8.06 (dd, 2H, J = 7.01), 8.12~8.16 (m, 2H), 8.61 (dd, 2H, J = 5.77), 8.68 (dd, 2H, J = 1.82) |
| 71 | C$_{44}$H$_{26}$S$_2$<br>M+ 619.15 | • • • 7.33~7.38 (m, 2H), 7.48 (dd, 2H, J = 8.83), 7.51~7.69 (m, 14H), 7.73~7.79 (m, 4H), 7.84~7.89 (m, 2H), 8.06 (dd, 1H, J = 7.74), 8.12 (dd, 1H, J = 3.75) |
| 72 | C$_{40}$H$_{22}$S$_2$<br>M+ 567.12 | • • = 7.61~7.70 (m, 6H), 7.91 (d, 2H, J = 1.89), 8.01~8.12 (m, 10H), 8.30 (dd, 2H, J = 6.45), 9.49 (dd, 2H, J = 4.91) |
| 73 | C$_{50}$H$_{34}$S$_2$<br>M+ 699.20 | • • = 7.53 (dd, 2H, J = 7.54), 7.57~7.62 (m, 6H), 7.71 (dd, 2H, J = 8.75), 7.81~7.90 (m, 8H), 8.16 (dd, 2H, J = 5.58), 8.23~8.26 (m, 4H), 8.30~8.60 (m, 10H) |
| 74 | C$_{44}$H$_{22}$S$_4$<br>M+ 679.05 | • • = 7.35~7.54 (m, 6H), 7.59~7.65 (m, 4H), 7.69 (dd, 2H, J = 7.58), 7.81~7.92 (m, 8H), 9.27~9.32 (m, 2H) |
| 75 | C$_{30}$H$_{16}$N$_2$S$_2$<br>M+ 469.08 | • • = 7.43 (dd, 2H, J = 1.70), 7.51 (dd, 2H, J = 8.55) 7.71~7.85 (m, 6H), 7.95 (dd, 2H, J = 8.32), 8.06~8.07 (m, 4H) |
| 76 | C$_{56}$H$_{32}$N$_2$S$_2$<br>M+ 797.20 | • • = 7.49~7.55 (m, 6H), 7.83~7.93 (m, 4H), 7.96~8.08 (m, 12H), 8.21~8.25 (m, 2H), 8.35~8.40 (m, 4H), 8.59~8.68 (m, 2H) |
| 77 | C$_{36}$H$_{20}$N$_2$S$_2$<br>M+ 545.10 | • • = 7.44~7.52 (m, 6H), 7.80~7.90 (m, 6H), 8.05~8.10 (m, 6H), 8.45 (d, 2H, J = 4.67) |

-continued

| No. | LC-MS | $^1$H NMR (CD$_2$Cl$_2$, 300 MHz) |
|---|---|---|
| 78 | C$_{50}$H$_{28}$N$_6$S$_2$<br>M+ 777.19 | • • = 7.30~7.35 (m, 2H), 7.54~7.72 (m, 7H), 7.82~7.86 (m, 2H),<br>7.93~8.08 (m, 6H), 8.17 (dd, 2H, J = 6.45), 8.20~8.33 (m, 6H),<br>8.43~8.45 (m, 1H), 8.51~8.55 (m, 1H) |
| 79 | C$_{40}$H$_{22}$S$_4$<br>M+ 630.07 | • • = 7.51~7.61 (m, 6H), 7.83~7.88 (m, 2H), 7.93 (dd, 2H, J = 7.44),<br>8.05~8.10 (m, 8H), 8.57 (d, 2H, J = 4.71) |
| 80 | C$_{46}$H$_{26}$N$_4$S$_2$<br>M+ 699.15 | • • = 7.55~7.68 (m, 10H), 7.94~8.03 (m, 6H), 8.11 (dd, 2H, J = 8.03),<br>8.23 (dd, 2H, J = 5.32), 8.29~8.31 (m, 2H), 8.77 (dd, 2H, J = 4.99), 8.85 (dd,<br>2H, J = 4.97) |
| 81 | C$_{44}$H$_{28}$N$_2$S$_2$<br>M+ 649.17 | • • = 7.51~7.78 (m, 12H), 7.82~8.02 (m, 12H), 8.08 (dd, 2H, J = 7.45),<br>8.23 (dd, 2H, J = 1.91) |
| 82 | C$_{32}$H$_{14}$F$_4$S$_2$<br>M+ 539.05 | • • = 7.48 (dd, 2H, J = 8.76), 7.60 (dd, 2H, J = 8.76), 7.73~7.79 (m, 4H),<br>8.09 (d, 2H, J = 4.51), 8.11 (dd, 2H, J = 7.33), 8.60~8.64 (m, 2H) |
| 83 | C$_{44}$H$_{22}$O$_2$S$_2$<br>M+ 647.11 | • • = 8.27~8.31 (m, 2H), 8.93~9.00 (m, 6H), 9.04~9.10 (m, 8H),<br>9.20 (d, 2H, J = 4.86), 9.28 (dd, 2H, J = 5.02), 9.34~9.37 (m, 2H) |
| 84 | C$_{40}$H$_{22}$N$_4$S$_2$<br>M+ 623.13 | • • = 7.92~8.05 (m, 6H), 8.24 (d, 2H, J = 4.04), 8.43 (dd, 2H, J = 5.63),<br>8.66~8.74 (m, 4H), 9.04~9.10 (m, 4H), 9.51~9.55 (m, 4H) |
| 85 | C$_{32}$H$_{18}$N$_4$S$_2$<br>M+ 52311 | • • = 6.47~6.52 (m, 4H), 6.67 (s, 2H), 7.18 (dd, 2H, J = 3.09),<br>7.82 (dd, 2H, J = 7.84), 7.98 (d, 2H, J = 1.01), 8.12~8.20 (m, 4H), 8.43 (s, 2H) |
| 86 | C$_{28}$H$_{26}$S$_2$<br>M+ 427.14 | • • = 1.45 (s, 18H), 7.51 (dd, 2H, J = 8.56), 7.76~7.80 (m, 2H),<br>8.04 (d, 2H, J = 1.86), 8.16 (dd, 2H, J = 8.56) |
| 87 | C$_{52}$H$_{32}$N$_2$S$_2$<br>M+ 749.21 | • • = 7.23~7.42 (m, 4H), 7.58~7.63 (m, 6H), 7.83~7.87 (m, 4H),<br>7.91~8.13 (m, 6H), 8.19~8.21 (m, 2H), 8.28~8.30 (m, 2H), 9.75 (d, 2H,<br>J = 1.99) |
| 88 | C$_{42}$H$_{24}$N$_2$S$_2$<br>M+ 620.11 | • • = 7.12~7.16 (m, 2H), 7.26~7.39 (m, 4H), 7.44~7.75 (m, 16H),<br>7.86 (dd, 1H, J = 8.79), 8.10~8.13 (m, 1H) |
| 89 | C$_{32}$H$_{16}$F$_2$S$_2$<br>M+ 503.05 | • • = 7.54~7.78 (m, 8H), 8.13 (d, 2H, J = 8.50), 8.26 (d, 2H,<br>J = 5.58), 8.42 (dd, 2H, J = 8.50), 8.54 (dd, 2H, J = 5.58) |
| 90 | C$_{40}$H$_{22}$N$_4$S$_2$<br>M+ 623.11 | • • = 7.05~7.09 (m, 2H), 7.21~7.30 (m, 4H), 7.50~7.78 (m, 14H),<br>7.90 (dd, 1H, J = 5.43), 8.10~8.13 (m, 1H) |
| 91 | C$_{28}$H$_{14}$O$_2$S$_2$<br>M+ 447.05 | • • = 6.47~6.52 (m, 2H), 6.67 (s, 2H), 7.82 (dd, 2H, J = 7.84),<br>7.98 (d, 2H, J = 1.01), 8.12~8.20 (m, 4H), 8.43 (s, 1H) |
| 92 | C$_{38}$H$_{20}$N$_2$S$_2$<br>M+ 569.10 | • • = 7.94~8.02 (m, 4H), 8.43~8.45 (m, 2H), 8.49 (d, 2H, J = 6.80),<br>8.55 (d, 2H, J = 6.80), 8.61~8.74 (m, 6H), 9.15 (dd, 2H, J = 5.05),<br>9.38~9.42 (m, 2H) |
| 93 | C$_{44}$H$_{26}$S$_2$<br>M+ 619.15 | • • = 7.35~7.48 (m, 6H), 7.58~7.71 (m, 14H), 7.84~7.92 (m, 4H),<br>8.06 (dd, 1H, J = 7.74), 8.12 (dd, 1H, J = 3.75) |
| 94 | C$_{42}$H$_{20}$F$_4$N$_2$S$_2$<br>M+ 693.09 | • • = 7.41~7.51 (m, 6H), 7.69~7.79 (m, 8H), 7.91~7.95 (m, 4H),<br>8.21 (dd, 2H, J = 5.32) |
| 95 | C$_{56}$H$_{36}$N$_2$S$_2$<br>M+ 801.22 | • • = 7.18~7.22 (m, 6H), 7.28~7.34 (m, 8H), 7.43~7.46 (m, 6H),<br>7.48~7.52 (m, 4H), 7.54~7.63 (m, 6H), 7.76 (dd, 2H, J = 4.38), 7.93 (dd,<br>2H, J = 8.32), 8.69 (dd, 2H, J = 8.32) |
| 96 | C$_{48}$H$_{26}$O$_2$S$_2$<br>M+ 699.14 | • • = 7.33~7.38 (m, 3H), 7.48~7.50 (m, 2H), 7.57~7.70 (m, 14H),<br>7.74~7.89 (m, 4H), 8.06 (dd, 1H, J = 7.74), 8.12 (dd, 1H, J = 3.75) |
| 97 | C$_{40}$H$_{22}$S$_4$<br>M+ 631.05 | • • = 7.44~7.52 (m, 6H), 7.63~7.75 (m, 2H), 8.05 (dd, 2H, J = 5.32),<br>8.10~8.19 (m, 8H), 8.43 (d, 2H, J = 5.33) |
| 98 | C$_{62}$H$_{42}$S$_2$<br>M+ 851.27 | • • = 2.85 (s, 12H), 7.58~7.72 (m, 6H), 7.81~7.90 (m, 6H),<br>8.07~8.10 (m, 2H), 8.27~8.31 (m, 6H), 8.51~8.54 (m, 4H),<br>8.86~8.90 (m, 4H), 9.10 (dd, 2H, J = 5.49) |
| 99 | C$_{54}$H$_{28}$N$_2$O$_2$S$_2$<br>M+ 801.15 | • • = 8.01 (dd, 2H, J = 8.62), 8.17~8.20 (m, 2H), 8.96~9.17 (m,<br>16H), 9.34~9.42 (m, 6H), 9.63 (dd, 2H, J = 5.35) |
| 100 | C$_{36}$H$_{30}$O$_2$S$_2$<br>M+ 559.15 | • • = 1.88 (s, 18H), 6.66 (dd, 2H, J = 2.80), 7.10 (dd, 2H, J = 2.81),<br>7.65 (d, 1H, J = 1.75), 7.90 (d, 1H, J = 1.75), 8.42 (d, 2H, J = 5.50),<br>8.54 (d, 2H, J = 8.03), 9.04 (dd, 2H, J = 5.50) |
| 101 | C$_{46}$H$_{20}$F$_{10}$O$_2$S$_2$<br>M+ 859.05 | • • = 4.13 (s, 6H), 7.14~7.18 (m, 4H), 7.56~7.60 (m, 2H),<br>7.71~7.74 (m, 2H), 8.08 (d, 2H, J = 5.35), 8.38 (d, 2H, J = 5.15),<br>8.64 (dd, 2H, J = 5.51) |
| 102 | C$_{38}$H$_{20}$N$_2$O$_2$S$_2$<br>M+ 601.10 | • • = 4.13 (s, 6H), 7.14~7.18 (m, 4H), 7.56~7.60 (m, 2H),<br>7.71~7.74 (m, 2H), 8.08 (d, 2H, J = 5.35), 8.38 (d, 2H, J = 5.15),<br>8.64 (dd, 2H, J = 5.51) |
| 103 | C$_{46}$H$_{36}$N$_2$O$_2$S$_2$<br>M+ 713.22 | • • = 2.30 (s, 18H), 6.76 (dd, 2H, J = 4.03), 6.95 (dd, 2H, J = 4.03),<br>7.73~7.76 (m, 2H), 7.98 (dd, 2H, J = 1.75), 8..70~8.83 (m, 6H), 9.26 (d,<br>4H, J = 5.07) |
| 104 | C$_{30}$H$_{16}$OS$_2$<br>M+ 457.05 | • • = 7.62~7.76 (m, 8H), 7.99 (dd, 2H, J = 1.82), 8.10~8.13 (m, 2H),<br>8.56 (dd, 2H, J = 1.83), 8.75 (dd, 2H, J = 1.82) |
| 105 | C$_{38}$H$_{20}$S$_3$<br>M+ 573.07 | • • = 7.90~7.95 (m, 4H), 8.41~8.43 (m, 2H), 8.50 (d, 2H, J = 8.23),<br>8.53 (d, 2H, J = 6.80), 8.60~8.69 (m, 6H), 9.14~9..39 (m, 4H) |
| 106 | C$_{38}$H$_{23}$NS$_2$<br>M+ 558.13 | • • = 7.18~7.34 (m, 7H), 7.40 (dd, 1H, J = 8.54), 7.57~7.69 (m, 8H),<br>7.84~7.90 (m, 1H), 8.01 (dd, 1H, J = 6.12), 8.19 (dd, 1H, J = 7.38),<br>8.24~8.30 (m, 2H), 8.38 (dd, 1H, J = 7.53) |
| 107 | C$_{38}$H$_{23}$NS$_2$<br>M+ 558.12 | • • = 7.16~7.25 (m, 6H), 7.33 (dd, 1H, J = 8.49), 7.56~7.70 (m, 8H),<br>7.85~7.92 (m, 2H), 8.07 (dd, 1H, J = 8.12), 8.19 (dd, 1H, J = 6.75),<br>8.31~8.35 (m, 2H), 8.71 (dd, 1H, J = 2.11) |
| 108 | C$_{29}$H$_{15}$NOS$_2$<br>M+ 458.05 | • • = 6.68 (dd, 1H, J = 2.79), 7.28 (dd, 1H, J = 2.79), 7.54~7.60 (m,<br>1H), 8.17 (d, 1H, J = 4.97), 8.18~8.21 (m, 1H), 8.86~8.89 (m, 1H),<br>8.94~8.90 (m, 5H), 9.12 (dd, 1H, J = 5.08), 9.27~9.30 (m, 1H),<br>9.50~9.52 (m, 1H) |

| No. | LC-MS | $^1$H NMR (CD$_2$Cl$_2$, 300 MHz) |
|---|---|---|
| 109 | C$_{38}$H$_{18}$F$_2$S$_3$<br>M+ 609.05 | • • = 6.45~6.49 (m, 4H), 6.64 (dd, 2H, J = 4.01), 7.15 (dd, 2H, J = 3.91), 7.79 (dd, 2H, J = 4.08), 7.98 (d, 2H, J = 1.01), 8.10~8.15 (m, 4H), 8.38 (m, 2H) |
| 110 | C$_{44}$H$_{33}$NS$_2$<br>M+ 640.21 | • • = 1.48 (t, 3H, J = 2.67), 2.21 (s, 9H), 5.11 (q, 2H, J = 2.67), 7.33 (dd, 1H, J = 7.56), 7.64~7.70 (m, 2H), 7.81~7.89 (m, 2H), 8.34~8.42 (m, 2H), 8.47~8.51 (m, 2H), 8.72 (dd, 1H, J = 7.56), 8.80~8.86 (m, 2H), 8.94 (d, 1H, J = 5.08), 9.06~9.23 (m, 5H) |
| 111 | C$_{42}$H$_{31}$NOS$_2$<br>M+ 630.18 | • • = 1.45 (t, 3H, J = 3.11), 2.19 (s, 9H), 5.05 (q, 2H, J = 3.15), 7.31 (dd, 1H, J = 7.56), 7.64~7.70 (m, 2H), 7.79~7.85 (m, 2H), 8.29~8.31 (m, 2H), 8.56 (dd, 1H, J = 3.15), 8.79~8.81 (m, 2H), 8.94~9.06 (m, 6H) |
| 112 | C$_{46}$H$_{30}$O$_2$S$_2$<br>M+ 679.17 | • • = 2.23 (s, 9H), 7.35 (dd, 1H, J = 4.33), 7.55~7.60 (m, 2H), 7.75~7.80 (m, 4H), 8.33~8.35 (m, 2H), 8.55~8.58 (m, 2H), 8.71 (dd, 2H, J = 4.10), 8.80~8.85 (m, 2H), 9.09~9.15 (m, 6H) |
| 113 | C$_{36}$H$_{18}$O$_2$S$_2$<br>M+ 547.07 | • • = 6.72 (dd, 1H, J = 3.86), 7.26 (dd, 1H, J = 3.86), 7.95~8.09 (m, 3H), 8.21~8.25 (m, 1H), 8.68~8.71 (m, 1H), 8.98~9.03 (m, 7H), 9.15 (dd, 1H, J = 5.07), 9.29~9.31 (m, 1H) |
| 114 | C$_{38}$H$_{21}$N$_3$S$_2$<br>M+ 584.12 | • • = 7.52~7.68 (m, 6H), 7.80~7.84 (m, 1H), 7.91 (d, 1H, J = 7.67), 8.05~8.23 (m, 4H), 8.35 (dd, 1H, J = 8.44), 8.44 (d, 1H, J = 8.44), 8.53 (d, 1H, J = 5.54), 8.60 (dd, 1H, J = 6.83), 8.63~8.68 (m, 2H), 8.82 (dd, 1H, J = 5.42), 8.88 (dd, 1H, J = 5.54), 9.13~9.15 (m, 1H) |
| 115 | C$_{37}$H$_{22}$N$_2$S$_2$<br>M+ 559.12 | • • = 7.22~7.28 (m, 2H), 7.45~7.51 (m, 4H), 7.59~7.62 (m, 4H), 7.66 (dd, 1H, J = 3.52), 7.70 (dd, 1H, J = 3.52), 7.78~7.85 (m, 4H), 7.91~7.94 (m, 4H), 9.30~9.34 (m, 2H) |
| 116 | C$_{47}$H$_{31}$NS$_2$<br>M+ 674.19 | • • = 2.35 (s, 6H), 7.19~7.45 (m, 11H), 7.55~7.70 (m, 7H), 7.99 (dd, 1H, J = 1.99), 8.09~8.16 (m, 2H), 8.28~8.29 (m, 1H), 8.55~8.58 (m, 1H), 8.60 (d, 1H, J = 0.77) |
| 117 | C$_{44}$H$_{28}$N$_2$S$_2$<br>M+ 649.17 | • • = 7.31 (dd, 2H, J = 1.85), 7.72 (dd, 2H, J = 1.85), 7.79 (dd, 1H, J = 2.01), 7.85 (dd, 1H, J = 8.39), 8.01~8.15 (m, 6H), 8.33 (dd, 2H, J = 8.38), 8.53~8.58 (m, 2H), 8.68~8.72 (m, 4H), 8.94~8.97 (m, 4H), 9.08~9.11 (m, 4H) |
| 118 | C$_{36}$H$_{18}$S$_6$<br>M+ 642.97 | • • = 7.49~7.55 (m, 3H), 7.61~7.65 (m, 4H), 7.84~7.89 (m, 2H), 8.09~8.14 (m, 3H), 8.72 (s, 1H), 8.73 (d, 2H, J = 1.82), 8.79 (d, 2H, J = 4.96), 8.98 (dd, 1H, J = 5.16) |
| 119 | C$_{36}$H$_{18}$O$_4$S$_2$<br>M+ 579.06 | • • = 7.35~7.44 (m, 3H), 7.55~7.60 (m, 4H), 7.70~7.79 (m, 2H), 8.00~8.12 (m, 3H), 8.55 (s, 1H), 8.65 (d, 2H, J = 8.41), 8.77 (d, 2H, J = 8.41), 8.85 (dd, 1H, J = 8.35) |
| 120 | C$_{55}$H$_{34}$N$_2$S$_2$<br>M+ 787.22 | • • = 4.31 (s, 3H), 7.45~7.50 (m, 1H), 7.63~7.71 (m, 3H), 7.80~7.82 (m, 1H), 7.90~8.08 (m, 15H), 8.86~8.98 (m, 6H), 9.08~9.13 (m, 3H), 9.20~9.22 (m, 2H) |
| 121 | C$_{60}$H$_{36}$N$_2$S$_2$<br>M+ 849.23 | • • = 7.33~7.39 (m, 2H), 7.45~7.51 (m, 4H), 7.75~7.80 (m, 2H), 7.92~8.10 (m, 16H), 8.75~8.80 (m, 6H), 9.01~9.11 (m, 4H), 9.19~9.23 (m, 2H) |
| 122 | C$_{60}$H$_{36}$N$_2$S$_2$<br>M+ 849.21 | • • = 7.63~7.70 (m, 4H), 7.98~8.03 (m, 8H), 8.36~8.40 (m, 8H), 8.54~8.58 (m, 4H), 8.90~8.95 (m, 2H), 9.03~9.05 (m, 2H), 9.21~9.28 (m, 4H), 9.53~9.59 (m, 4H) |
| 123 | C$_{68}$H$_{40}$N$_2$S$_4$<br>M+ 1012.21 | • • = 7.68~7.73 (m, 4H), 8.00~8.05 (m, 8H), 8.40~8.43 (m, 8H), 8.60~8.65 (m, 4H), 8.75~8.79 (m, 4H) 8.91~8.96 (m, 2H), 9.10~9.16 (m, 2H), 9.20~9.27 (m, 4H), 9.49~9.53 (m, 4H) |
| 124 | C$_{44}$H$_{22}$S$_4$<br>M+ 679.06 | • • = 8.82~8.91 (m, 8H), 8.96~9.00 (m, 2H), 9.02~9.04 (m, 1H), 9.16~9.20 (m, 2H), 9.24~9.28 (m, 1H), 9.32~9.40 (m, 8H) |
| 125 | C$_{36}$H$_{18}$O$_2$S$_2$<br>M+ 547.07 | • • = 6.70 (dd, 2H, J = 4.18), 7.29 (dd, 2H, J = 4.18), 8.06 (dd, 2H, J = 1.75), 8.73~8.75 (m, 2H), 8.82~8.85 (m, 2H), 9.21 (d, 2H, J = 5.06), 9.31~9.42 (m, 6H) |
| 126 | C$_{46}$H$_{24}$N$_2$O$_2$S$_2$<br>M+ 701.13 | • • = 6.59 (dd, 2H, J = 4.41), 7.84 (dd, 2H, J = 4.41), 8.09 (dd, 2H, J = 1.75), 8.65~8.68 (m, 2H), 8.73~8.78 (m, 4H), 8.82~8.88 (m, 6H), 9.34~9.39 (m, 4H), 9.41 (s, 2H) |

Example 1

To manufacture an anode, a corning 15 Ω/cm² (1200 Å) ITO glass substrate was cut to a size of 50 mm×50 mm×0.7 mm and then sonicated in isopropyl alcohol and pure water each for live minutes, and then cleaned by irradiation of ultraviolet rays for 30 minutes and exposure to ozone. The resulting glass substrate was loaded into a vacuum deposition device.

Then, 2-TNATA, which is a HIL material, was vacuum-deposited on the glass substrate to form a HIL having a thickness of about 600 Å. Then, 4,4'-bis[N-(1-naphthyl)-N-phenylamino-]biphenyl (NPB), which is a hole transporting compound, was vacuum-deposited on the HIL to form a HTL having a thickness of about 300 Å.

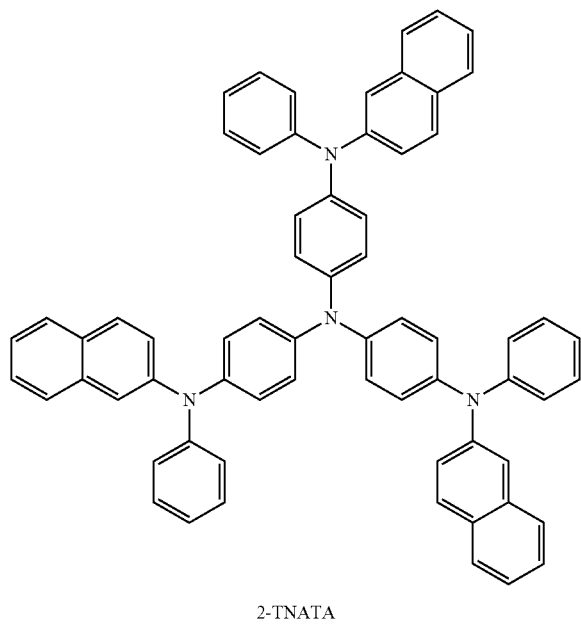

2-TNATA

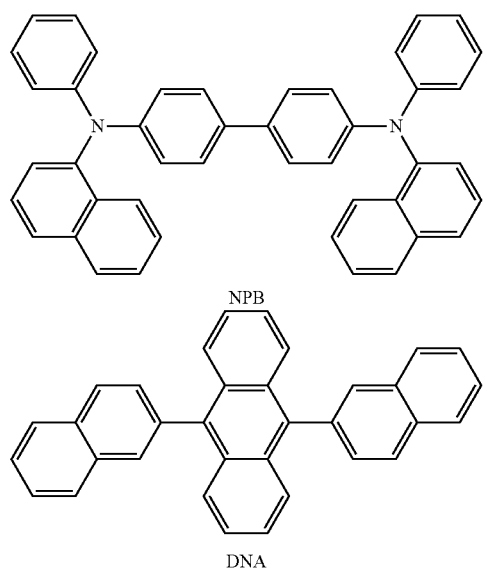

NPB

DNA

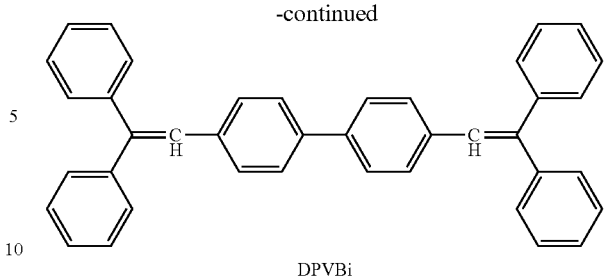

DPVBi

A blue fluorescent host 9,10-di-naphthalene-2-yl-anthracene (DNA) and a blue fluorescent dopant 1,4-bis-(2,2-diphenylvinyl)biphenyl (DPV81), which are both widely known compounds, were deposited at the same time on the HTL in a weight ratio of 98:2 to form an EML having a thickness of 300 Å.

Then, Compound 3 was deposited on the EML to form an ETL, and then LiF, which is a halogenated alkali metal, was deposited on the ETL to form an EIL having a thickness of 10 Å. Then, Al was vacuum-deposited on the EIL to form a cathode having a thickness of 3000 Å, thereby forming a LiF/Al electrode and completing the manufacture of an organic light-emitting device.

Example 2

An organic light-emitting device was manufactured in the same manner as in Example 1, except that Compound 14 was used, instead of Compound 3, to form the ETL.

Example 3

An organic light-emitting device was manufactured in the same manner as in Example 1, except that Compound 34 was used, instead of Compound 3, to form the ETL.

Example 4

An organic light-emitting device was manufactured in the same manner as in Example 1, except that Compound 51 was used, instead of Compound 3, to form the ETL.

Example 5

An organic light-emitting device was manufactured in the same manner as in Example 1, except that Compound 24 was used, instead of the known host DNA, to form the EML, and a widely-known Alq3 was used to form an ETL on the EML.

Example 6

An organic light-emitting device was manufactured in the same manner as in Example 5, except that Compound 26 was used, instead of Compound 24, to form the EML.

Example 7

An organic light-emitting device was manufactured in the same manner as in Example 1, except that Compound 1 was used, instead of the widely known NPB, to form the HTL, and a blue fluorescent host 9,10-di-naphthalene-2-yl-anthracene (DNA) and a blue fluorescent dopant 1,4-bis-(2,2-diphenylvinyl)biphenyl (DPVBi), which are both widely known compounds, were deposited at the same time on the HTL in a weight ratio of 98:2 to form an EML having a thickness of 300 Å.

Example 8

An organic light-emitting device was manufactured in the same manner as in Example 7, except that Compound 13 was used, instead of Compound 1, to form the HTL.

Example 9

An organic light-emitting device was manufactured in the same manner as in Example 7, except that Compound 44 was used, instead of Compound 1, to form the HTL.

Example 10

An organic light-emitting device was manufactured in the same manner as in Example 1, except that Compound 26 was used as a blue fluorescent host to form the EML, and Compound 34 was used to form the ETL.

Example 11

An organic light-emitting device was manufactured in the same manner as in Example 7, except that Compound 51 was used, instead of Compound 34, to form the ETL.

Example 12

An organic light-emitting device was manufactured in the same manner as in Example 1, except that Compound 13 was used to form the HTL, Compound 26 was used as a blue fluorescent host to form the EML, and Compound 3 was used, instead of Alq3, to form the ETL.

Comparative Example 1

An organic light-emitting device was manufactured in the same manner as in Example 1, except that a widely known blue fluorescent host 9,10-di-naphthalene-2-yl-anthracene (DNA) was used, instead of Compound 7, to form the EML.

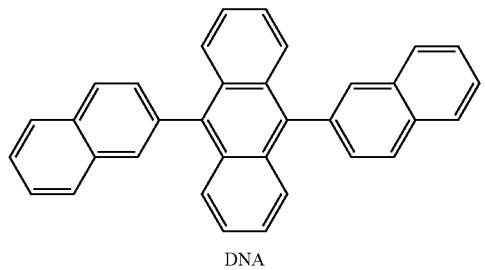 [SMILES: c1ccc2cc(-c3c4ccccc4c(-c4ccc5ccccc5c4)c4ccccc34)ccc2c1]

DNA

When the heterocyclic compounds of Formula 1 wherein $X_1$ and $X_2$ are —$N(R_{20})$— were used as a HTL material, a host in EML, and/or an ETL material of an organic light-emitting device, driving voltages were lower by about 1V or greater than those of the organic light-emitting devices in which the widely-known material 2-TNATA, DNA, NPB, and/or Alq3 was used. In addition, good I-V-L characteristics with improved efficiency, and remarkable improvements in luminance and lifetime were attained. The organic light-emitting devices of Example 1-4 including the heterocyclic compounds of Formula 1 as ETL materials are found to have higher efficiencies and longer lifetimes than the organic light-emitting device of Comparative Example 1. The organic light-emitting devices of Examples 5-6 including the heterocyclic compounds of Formula 1 as hosts are found to have lower driving voltages by about 1.5V or greater, higher efficiencies by about 150% or greater, and longer lifetimes than the organic light-emitting device of Comparative Example 1. The organic light-emitting devices of Examples 7-9 including the heterocyclic compounds of Formula 1 as HTL materials are found to have lower driving voltages by about 1.0V or greater than the organic light-emitting device of Comparative Example 1. The organic light-emitting devices of Examples 10-11 including the heterocyclic compounds of Formula 1 as a host or an ETL material are found to have lower driving voltages by about 1.4V or greater, higher efficiencies, and longer lifetimes than the organic light-emitting device of Comparative Example 1. The organic light-emitting device of Example 12 including the heterocyclic compounds of Formula 1 as a HTL material, a host of an EML, and an ETL material are found to have a lower driving voltage by about 2.1V, a higher efficiency by about 200%, and a longer lifetime by about 100% or greater than the organic light-emitting device of Comparative Example 1. The characteristics of the organic light-emitting devices of Examples 1-12 and Comparative Example 1 are shown in Table 1 below.

TABLE 1

| | EML, HTL, or ETL material | Driving voltage (V) | Current density (mA/cm$^2$) | Luminance (cd/m$^2$) | Efficiency (cd/A) | Luminescent color | Half life-span (hr @100 mA/cm$^2$) |
|---|---|---|---|---|---|---|---|
| Example 1 | Compound 3 | 6.20 | 50 | 1,982 | 3.96 | blue | 204 hr |
| Example 2 | Compound 14 | 6.78 | 50 | 2,104 | 4.21 | blue | 181 hr |
| Example 3 | Compound 34 | 6.61 | 50 | 2,414 | 4.82 | blue | 175 hr |
| Example 4 | Compound 51 | 6.09 | 50 | 2,067 | 4.13 | blue | 189 hr |
| Example 5 | Compound 24 | 6.35 | 50 | 2,431 | 4.86 | blue | 202 hr |
| Example 6 | Compound 26 | 6.24 | 50 | 2,574 | 5.14 | blue | 207 hr |
| Example 7 | Compound 1 | 5.98 | 50 | 2,248 | 4.50 | blue | 179 hr |
| Example 8 | Compound 13 | 6.83 | 50 | 2,399 | 4.79 | blue | 196 hr |
| Example 9 | Compound 44 | 5.79 | 50 | 2,117 | 4.23 | blue | 172 hr |

TABLE 1-continued

| | EML, HTL, or ETL material | Driving voltage (V) | Current density (mA/cm$^2$) | Luminance (cd/m$^2$) | Efficiency (cd/A) | Luminescent color | Half life-span (hr @100 mA/cm$^2$) |
|---|---|---|---|---|---|---|---|
| Example 10 | EML's host Compound 26, ETL Compound 34 | 6.46 | 50 | 3,080 | 6.16 | blue | 223 hr |
| Example 11 | EML's host Compound 26, ETL Compound 51 | 6.21 | 50 | 3,230 | 6.46 | blue | 218 hr |
| Example 12 | HTL Compound 13 EML's host Compound 26, ETL Compound 3 | 5.68 | 50 | 2,896 | 5.79 | blue | 234 hr |
| Comparative Example 1 | DNA-DPVBi | 7.85 | 50 | 1,560 | 3.12 | blue | 113 hr |

Example 13

To manufacture an anode, a corning 15 Ω/cm$^2$ (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

Then, 2-TNATA, which is a HIL material, was vacuum-deposited on the glass substrate to form a HIL having a thickness of about 600 Å. Then, 4,4'-bis[N-(1-naphthyl)-N-phenylamino]biphenyl (NPB), which is a hole transporting compound, was vacuum-deposited on the HIL to form a HTL having a thickness of about 300 Å.

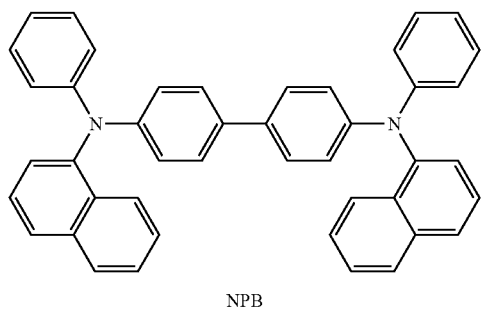

NPB

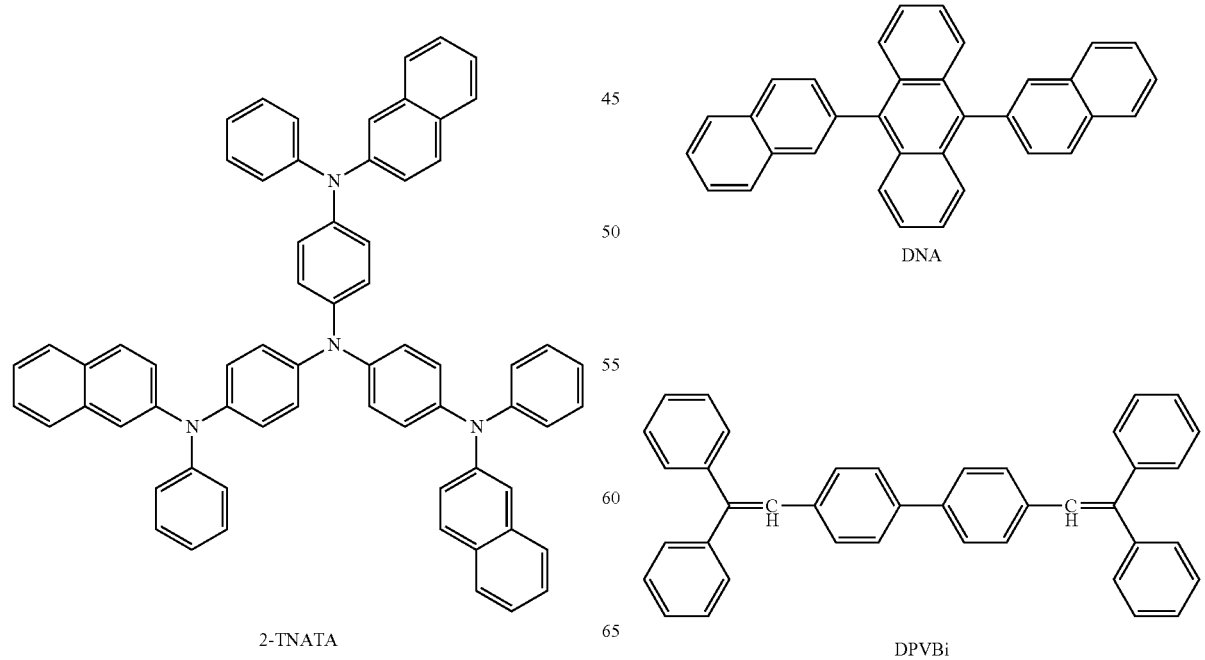

2-TNATA

DNA

DPVBi

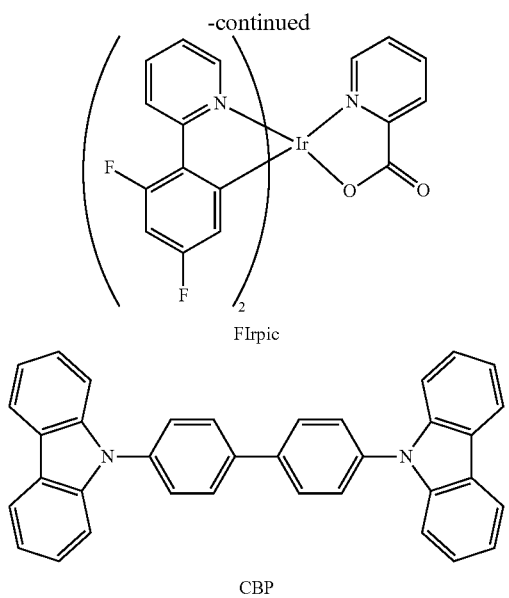

FIrpic

CBP

Then, the Compound 70 as a blue phosphorescent host and a widely known compound FIrpic as a blue phosphorescent dopant were simultaneously deposited on the HTL in a weight ratio of 90:10 to form an EML having a thickness of about 300 Å.

Then, Alq3 was deposited on the EML to form an ETL having a thickness of 300 Å, and then LiF, which is a halogenated alkali metal, was deposited on the ETL to form an EIL having a thickness of 10 Å. Then, Al was vacuum-deposited on the EEL to form a cathode having a thickness of 3000 Å, thereby forming an LiF/Al electrode and completing the manufacture of an organic light-emitting device.

Example 14

An organic light-emitting device was manufactured in the same manner as in Example 13, except that Compound 74 was used, instead of Compound 70, to form the EML.

Example 15

An organic light-emitting device was manufactured in the same manner as in Example 13, except that Compound 82 was used, instead of Compound 70, to form the EML.

Example 16

An organic light-emitting device was manufactured in the same manner as in Example 13, except that Compound 83 was used, instead of Compound 70, to form the EML.

Example 17

An organic light-emitting device was manufactured in the same manner as in Example 13, except that the known host CBP and known dopant FIrpic were used to form the EML, and Compound 72 was used, instead of the known Alq3, used to form the ETL on the EML.

Example 18

An organic light-emitting device was manufactured in the same manner as in Example 17, except that Compound 84 was used, instead of Compound 72, to form the ETL.

Example 19

An organic light-emitting device was manufactured in the same manner as in Example 17, except that Compound 92 was used, instead of Compound 72, to form the ETL.

Example 20

An organic light-emitting device was manufactured in the same manner as in Example 13, except that Compound 87 was used, instead of NPB, to form the HTL, and a widely known host CBP and a widely-known dopant FIrpic were used to form the EML.

Example 21

An organic light-emitting device was manufactured in the same manner as in Example 13, except that Compound 74 was used as a blue phosphorescent host to form the EML, and Compound 72 was used to form the ETL.

Example 22

An organic light-emitting device was manufactured in the same manner as in Example 21, except that Compound 92 was used, instead of Compound 72, to form the ETL.

Example 23

An organic light-emitting device was manufactured in the same manner as in Example 13, except that Compound 87 was used, instead of NPB, to form the HTL, Compound 82 was used as a blue phosphorescent host to form the EML, and Compound 84 was used, instead of Alq3, to form the ETL.

Comparative Example 2

An organic light-emitting device was manufactured in the same manner as in Example 13, except that a widely known blue phosphorescent host CBP was used, instead of Compound 70, to form the EML.

Comparative Example 3

An organic light-emitting device was manufactured in the same manner as in Example 22, except that a widely known blue fluorescent dopant DPVBi was used to form the EML.

When the heterocyclic compounds of Formula 1 wherein $X_1$ and $X_2$ are —S— were used as a fluorescent/phosphorescent host or a fluorescent dopant of an EML, an ETL material and/or a HTL material of an organic light-emitting device, in the phosphorescent organic light-emitting devices driving voltages were lower by about 1V or greater than the organic light-emitting device of Comparative Example 2, and good I-V-L characteristics with improved efficiency were attained. The organic light-emitting devices of Examples 13-16 including the heterocyclic compounds of Formula 1 as phosphorescent hosts are found to have lower driving voltages by about 1V, higher efficiencies, and longer lifetimes than the organic light-emitting device of Comparative Example 2. The organic light-emitting devices of Examples 17-19 including the heterocyclic compounds of Formula 1 as ETL materials are found to have higher efficiencies by about 145% or greater, and longer lifetimes than the organic light-emitting device of Comparative Example 2. The organic light-emitting device of Example 20 including the heterocyclic compound of Formula 1 as a HTL material is found to have a longer lifetime by about 185% or greater than the organic light-emitting device of Comparative Example 2. The organic light-emitting devices of Examples 21 and 22 including the heterocyclic compounds of Formula 1 as a phosphorescent host or an ETL material are found to have higher efficiencies by about 160% than the organic light-emitting device of Comparative Example 2. The organic light-emitting device of Example 23 including the heterocyclic compounds of Formula 1 as a phosphorescent host of an EML, a HTL material, and an ETL material is found to have a lower driving voltage by about 1.1V, a higher efficiency by about 170%, and a longer lifetime by about 180% or greater than the organic light-emitting device of Comparative Example 2. The characteristics of the organic light-emitting devices of Examples 13-23 and Comparative Examples 2 and 3 are shown in Table 1 below.

TABLE 2

| | EML or HTL material | Driving voltage (V) | Current density (mA/cm$^2$) | Luminance (cd/m$^2$) | Efficiency (cd/A) | Luminescent color | Half life-span (hr @100 mA/cm$^2$) |
|---|---|---|---|---|---|---|---|
| Example 13 | Phosphorescent host Compound 70 | 6.79 | 50 | 2,288 | 4.58 | blue | 168 hr |
| Example 14 | Phosphorescent host Compound 74 | 6.85 | 50 | 2,342 | 4.68 | blue | 176 hr |
| Example 15 | Phosphorescent host Compound 82 | 6.81 | 50 | 2,478 | 4.95 | blue | 204 hr |
| Example 16 | Phosphorescent host Compound 83 | 6.70 | 50 | 2,413 | 4.83 | blue | 183 hr |
| Example 17 | HTL material Compound 72 | 6.76 | 50 | 2,349 | 4.69 | blue | 212 hr |
| Example 18 | HTL material Compound 84 | 6.89 | 50 | 2,372 | 4.74 | blue | 198 hr |
| Example 19 | ETL material Compound 92 | 6.91 | 50 | 2,290 | 4.58 | blue | 201 hr |
| Example 20 | HTL material Compound 87 | 6.68 | 50 | 2,412 | 4.82 | blue | 210 hr |
| Example 21 | Phosphorescent host Compound 74, ETL material Compound 72 | 6.53 | 50 | 2.472 | 4.94 | blue | 216 hr |
| Example 22 | Phosphorescent host Compound 74, ETL material Compound 92 | 6.81 | 50 | 2,602 | 5.20 | blue | 227 hr |
| Example 23 | HTL material Compound 87, Phosphorescent host Compound 82, ETL material Compound 84 | 6.67 | 50 | 2,608 | 5.21 | blue | 208 hr |
| Comparative Example 2 | CBP-Firpic | 7.85 | 50 | 1,560 | 3.12 | blue | 113 hr |
| Comparative Example 3 | CBP-DPVBi | 8.12 | 50 | 1,432 | 2.86 | blue | 121 hr |

As described above, novel heterocyclic compounds according to the one or more of the above embodiments of the present invention have good emission characteristics and charge transporting capabilities, and thus may be used as an electron injecting/transporting material for most color-fluorescent and phosphorescent devices, such as red, green, blue, and white fluorescent and phosphorescent devices, especially as a light-emitting material of green, blue, or white fluorescent device. Thus, an organic light-emitting device with high-efficiency, low-driving voltage, high luminance and long lifespan may be manufactured using the heterocyclic compounds.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A compound represented by Formula 1 below:

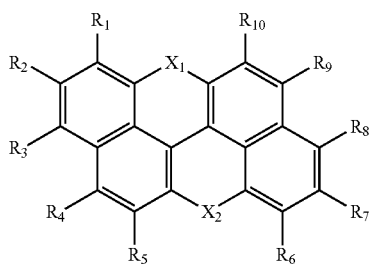

Formula 1 wherein, in Formula 1, $R_2$ to $R_4$ and $R_7$ to $R_9$ are each independently a hydrogen atom, a deuterium atom, a halogen group, a cyano group, a substituted or unsubstituted $C_1$-$C_{60}$ alkyl group, a substituted or unsubstituted $C_1$-$C_{50}$ alkenyl group, a substituted or unsubstituted $C_5$-$C_{60}$ aryl group, an amino group substituted with a substituted or unsubstituted $C_5$-$C_{60}$ aryl group, a substituted or unsubstituted $C_3$-$C_{60}$ heteroaryl group, or a substituted or unsubstituted $C_6$-$C_{60}$ condensed polycyclic group;

$R_1$, $R_5$, $R_{10}$ and $R_6$ are each independently a substituted or unsubstituted ethyl group, a propyl group, an isobutyl group, a sec-butyl group, a pentyl group, an iso-amyl group, a hexyl group, a heptyl group, an octyl group, a nonanyl group, or a dodecyl group;

$X_1$ and $X_2$ are each independently —N($R_{20}$)— or —S—;

adjacent substituents among $R_1$ to $R_5$ or those among $R_6$ to $R_{10}$ are optionally linked to form a ring; and $R_{20}$ is a hydrogen atom, a deuterium atom, a halogen group, a cyano group, a substituted or unsubstituted $C_1$-$C_{60}$ alkyl group, a substituted or unsubstituted $C_1$-$C_{50}$ alkenyl group, a substituted or unsubstituted $C_5$-$C_{60}$ aryl group, an amino group substituted with a substituted or unsubstituted $C_5$-$C_{60}$ aryl group, a substituted or unsubstituted $C_3$-$C_{60}$ heteroaryl group, or a substituted or unsubstituted $C_6$-$C_{60}$ condensed polycyclic group.

2. A compound of claim 1, wherein, in Formula 1, $R_2$ to $R_4$, $R_7$ to $R_9$, and $R_{20}$ are each independently a hydrogen atom, a deuterium atom, a halogen group, a cyano group, a substituted or unsubstituted $C_1$-$C_{20}$ alkyl group, a substituted or unsubstituted $C_1$-$C_{20}$ alkenyl group, a substituted or unsubstituted $C_5$-$C_{30}$ aryl group, an amino group substituted with a substituted or unsubstituted $C_5$-$C_{30}$ aryl group, a substituted or unsubstituted $C_3$-$C_{30}$ heteroaryl group, or a substituted or unsubstituted $C_6$-$C_{30}$ condensed polycyclic group.

3. A compound of claim 1, wherein, in Formula 1, $R_2$ to $R_4$, $R_7$ to $R_9$, and $R_{20}$ are each independently selected from the group consisting of a hydrogen atom, a deuterium atom, a halogen atom, a cyano group, a substituted or unsubstituted $C_1$-$C_{20}$ alkyl group, a substituted or unsubstituted $C_1$-$C_{20}$ alkenyl group, and groups represented by Formulae 2a to 2j below:

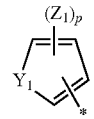

2a

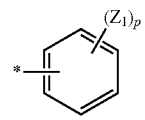

2b

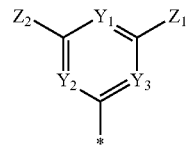

2c

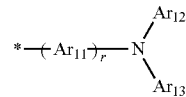

2d

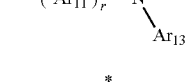

2e

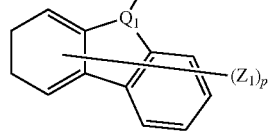

2f

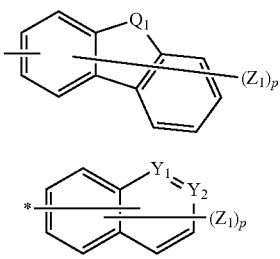

2g

2h

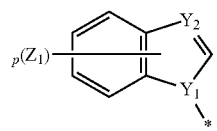

2i

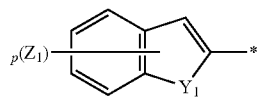

2j

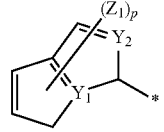

wherein, in Formulae 2a to 2j, $Q_1$ is represented by —$C(R_{30})(R_{31})$—, —$N(R_{32})$—, —N(-*)-, —S—, or —O—;

$Y_1$, $Y_2$, and $Y_3$ are each independently represented by —N=, —N(-*)-, —S—, —O—, —$C(R_{33})$=, or —C(-*)=;

$Z_1$, $Z_2$, $Ar_{12}$, $Ar_{13}$, $R_{30}$, $R_{31}$, $R_{32}$, and $R_{33}$ are each independently selected from the group consisting of a lone pair electron, a hydrogen atom, a deuterium atom, a halogen group, a cyano group, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a nitro group, a hydroxyl group, and a carboxy group;

$Ar_{11}$ is selected from the group consisting of a substituted or unsubstituted $C_1$-$C_{20}$ alkylene group, a substituted or unsubstituted $C_5$-$C_{20}$ arylene group, and a substituted or unsubstituted $C_3$-$C_{20}$ heteroarylene group;

p is an integer from 1 to 10;

r is an integer from 0 to 5; and

* is a binding site.

4. A compound of claim 1, wherein, in Formula 1, $R_2$ to $R_4$, $R_7$ to $R_9$, and $R_{20}$ are each independently selected from the group consisting of a hydrogen atom, a deuterium atom, a halogen group, a cyano group, a substituted or unsubstituted $C_1$-$C_{20}$ alkyl group, a substituted or unsubstituted $C_1$-$C_{20}$ alkenyl group, and groups represented by Formulae 3a to 3h below:

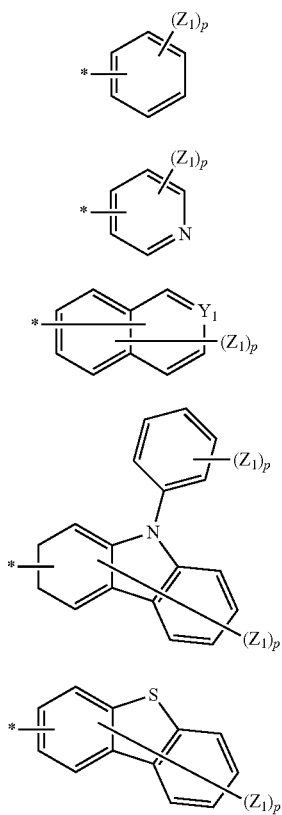

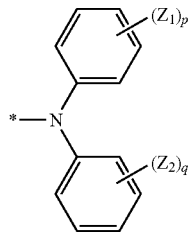

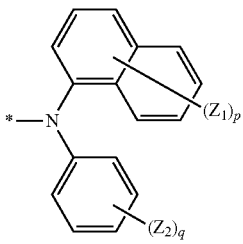

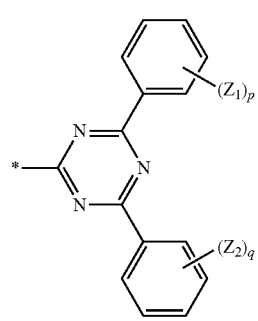

wherein, in Formulae 3a to 3h, $Y_1$ is represented by —N=, —S—, —O—, or —$C(R_{34})$=;

$Z_1$ and $Z_2$ are each independently selected from the group consisting of a hydrogen atom, a deuterium atom, a halogen group, a cyano group, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a nitro group, a hydroxyl group, and a carboxy group;

p and q are each independently an integer from 1 to 7; and

* is a binding site.

5. A compound of claim 1, wherein the compound represented by Formula 1 is symmetrical.

6. A compound of claim 1, wherein, in Formula 1, $R_2$ to $R_4$, $R_7$ to $R_9$, and $R_{20}$ are each independently selected from the group consisting of a hydrogen atom, a deuterium atom, a halogen group, a cyano group, a substituted or unsubstituted $C_1$-$C_{20}$ alkyl group, a substituted or unsubstituted $C_1$-$C_{20}$ alkenyl group, and groups represented by Formulae 2a to 2j below; and the compound represented by Formula 1 is symmetrical:

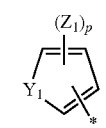

-continued

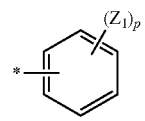   2b

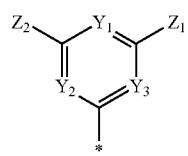   2c

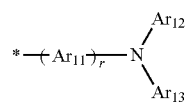   2d

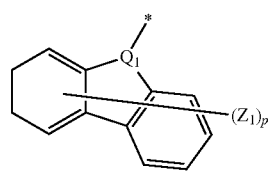   2e

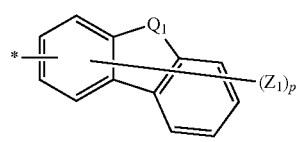   2f

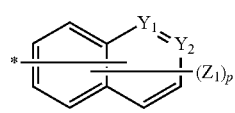   2g

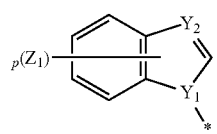   2h

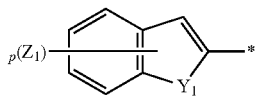   2i

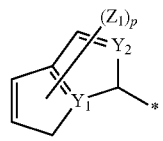   2j wherein, in Formulae 2a to 2j, $Q_1$ is represented by —C($R_{30}$)($R_{31}$)—, —N($R_{32}$)—, —N(-*)-, —S—, or —O—;

$Y_1$, $Y_2$, and $Y_3$ are each independently represented by —N=, —N(-*)-, —S—, —O—, —C($R_{33}$)=, or —C(-*)=;

$Z_1$, $Z_2$, $Ar_{12}$, $Ar_{13}$, $R_{30}$, $R_{31}$, $R_{32}$, and $R_{33}$ are each independently selected from the group consisting of a lone pair electron, a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, and a carboxy group;

$Ar_{11}$ is selected from the group consisting of a substituted or unsubstituted $C_1$-$C_{20}$ alkylene group, a substituted or unsubstituted $C_5$-$C_{20}$ arylene group, and a substituted or unsubstituted $C_3$-$C_{20}$ heteroarylene group;

p is an integer from 1 to 10;

r is an integer from 0 to 5; and

* is a binding site.

7. A compound of claim 1, wherein the compound of Formula 1 is one of the compounds below:

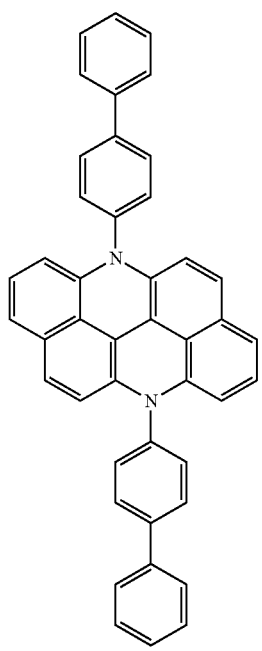   3

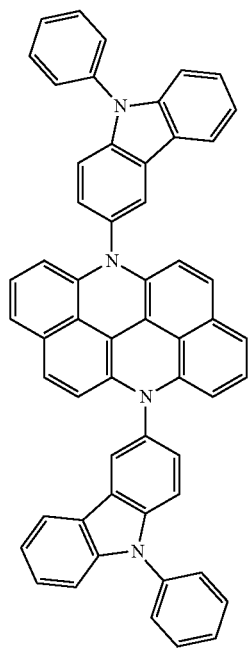   13

-continued
26
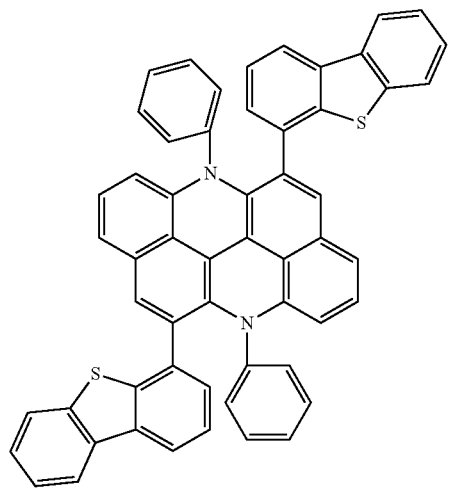
51
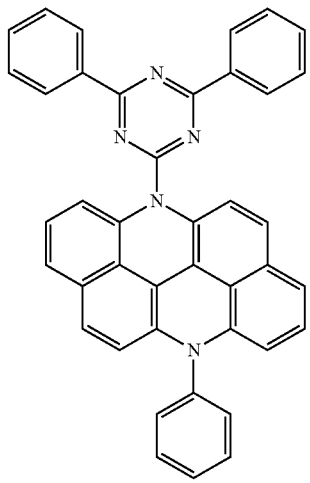
34
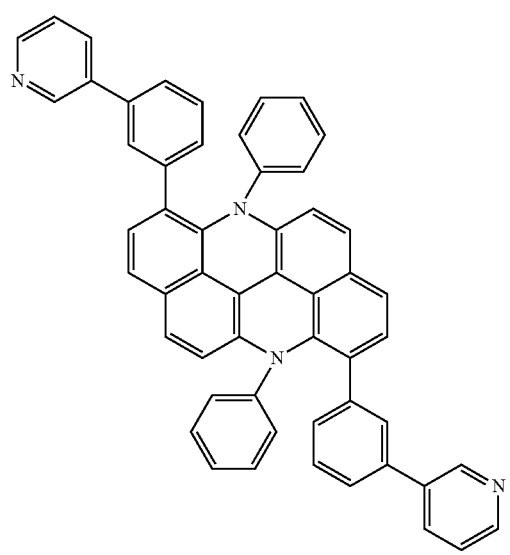
72
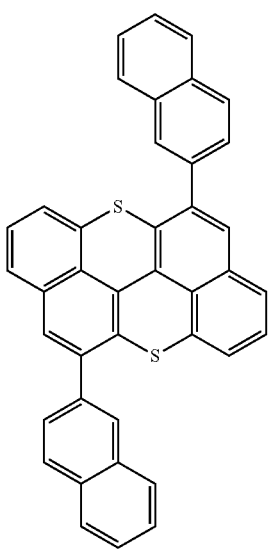
44
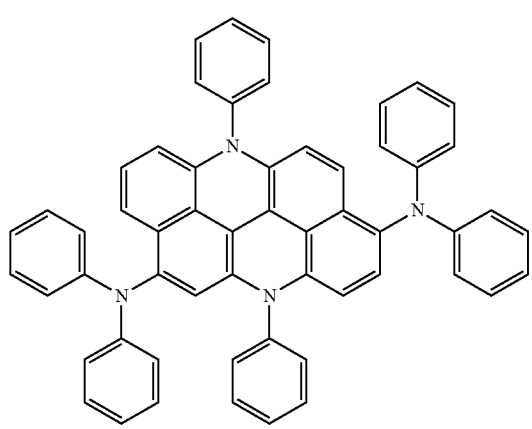
84
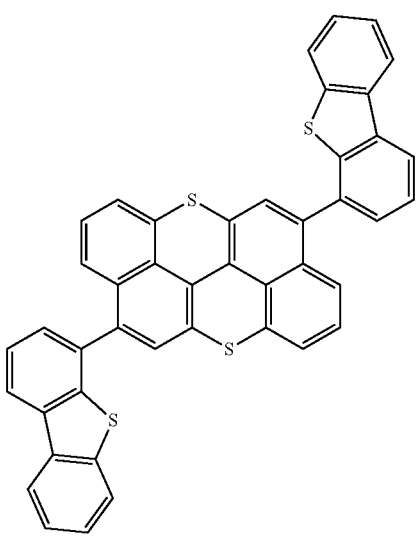

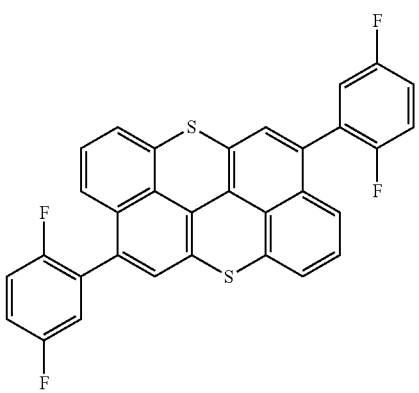

82

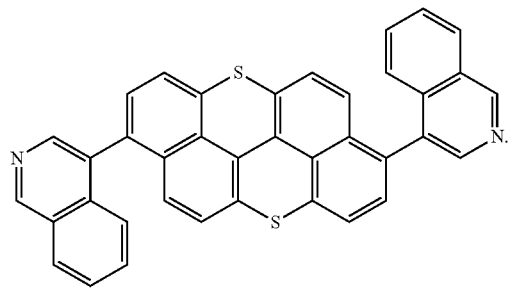

92

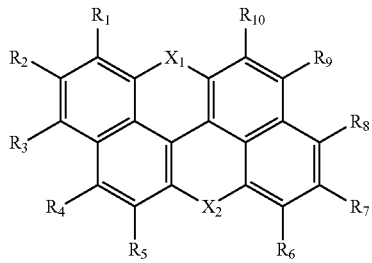

84

87

8. An organic light-emitting device comprising:
a first electrode;
a second electrode; and
an organic layer between the first electrode and the second electrode,
wherein the organic layer comprises a first layer including a compound represented by Formula 1 below:

Formula 1 wherein, in Formula 1, $R_1$ to $R_{10}$ are each independently a hydrogen atom, a deuterium atom, a halogen group, a cyano group, a substituted or unsubstituted $C_1$-$C_{60}$ alkyl group, a substituted or unsubstituted $C_1$-$C_{50}$ alkenyl group, a substituted or unsubstituted $C_5$-$C_{60}$ aryl group, an amino group substituted with a substituted or unsubstituted $C_5$-$C_{60}$ aryl group, a substituted or unsubstituted $C_3$-$C_{60}$ heteroaryl group, or a substituted or unsubstituted $C_6$-$C_{60}$ condensed polycyclic group;

$X_1$ and $X_2$ are each independently —N($R_{20}$)— or —S—;

adjacent substituents among $R_1$ to $R_5$ or those among $R_6$ to $R_{10}$ are optionally linked to form a ring; and $R_{20}$ is a hydrogen atom, a deuterium atom, a halogen group, a cyano group, a substituted or unsubstituted $C_1$-$C_{60}$ alkyl group, a substituted or unsubstituted $C_1$-$C_{50}$ alkenyl group, a substituted or unsubstituted $C_5$-$C_{60}$ aryl group, an amino group substituted with a substituted or unsubstituted $C_5$-$C_{60}$ aryl group, a substituted or unsubstituted $C_3$-$C_{60}$ heteroaryl group, or a substituted or unsubstituted $C_6$-$C_{60}$ condensed polycyclic group.

9. The organic light-emitting device of claim 8, wherein the first layer comprises at least one layer selected from the group consisting of a hole injection layer, a hole transport layer, a layer having both hole injection and hole transport capabilities, an electron injection layer, an electron transport layer, and a functional layer having both electron injection and electron transport capabilities.

10. The organic light-emitting device of claim 8, wherein the organic layer is an emission layer comprising a compound of Formula 1.

11. The organic light-emitting device of claim 8, wherein the organic layer comprises an emission layer, a hole transport layer, and an electron transport layer; and the first layer is an emission layer that further comprises an anthracene compound, an arylamine compound, or a styryl compound.

12. The organic light-emitting device of claim 8, wherein the organic layer comprises an emission layer, a hole transport layer, and an electron transport layer; and the first layer is an emission layer which further comprises a phosphorescent compound.

13. The organic light-emitting device of claim 8, wherein the first layer is a blue emission layer.

14. The organic light-emitting device of claim 8, wherein the first layer is a blue emission layer, and comprises a compound of Formula 1.

15. The organic light-emitting device of claim 8, wherein the organic layer further comprises a hole injection layer, a hole transport layer, a layer having both hole injection and hole transport capabilities, an emission layer, a hole blocking layer, an electron transport layer, an electron injection layer, or a combination of at least two thereof.

16. The organic light-emitting device of claim 15, wherein at least one of the hole injection layer, the hole transport layer, and the layer having hole injection and hole transport capabilities further comprises a charge generating material.

17. The organic light-emitting device of claim 15, wherein the electron transport layer comprises an electron transporting organic material and a metal-containing material.

18. The organic light-emitting device of claim 17, wherein the metal-containing material comprises a lithium (Li) complex.

19. The organic light-emitting device of claim 8, wherein the first layer is formed from the compound of Formula 1 below using a wet process:

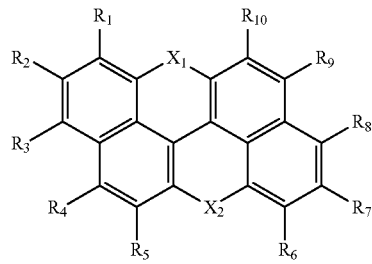

Formula 1 wherein, in Formula 1, $R_1$ to $R_{10}$ are each independently a hydrogen atom, a deuterium atom, a halogen group, a cyano group, a substituted or unsubstituted $C_1$-$C_{60}$ alkyl group, a substituted or unsubstituted $C_1$-$C_{50}$ alkenyl group, a substituted or unsubstituted $C_5$-$C_{60}$ aryl group, an amino group substituted with a substituted or unsubstituted $C_5$-$C_{60}$ aryl group, a substituted or unsubstituted $C_3$-$C_{60}$ heteroaryl group, or a substituted or unsubstituted $C_6$-$C_{60}$ condensed polycyclic group;

$X_1$ and $X_2$ are each independently —N($R_{20}$)— or —S—;

adjacent substituents among $R_1$ to $R_5$ or those among $R_6$ to $R_{10}$ are optionally linked to form a ring; and $R_{20}$ is a hydrogen atom, a deuterium atom, a halogen group, a cyano group, a substituted or unsubstituted $C_1$-$C_{60}$ alkyl group, a substituted or unsubstituted $C_1$-$C_{50}$ alkenyl group, a substituted or unsubstituted $C_5$-$C_{60}$ aryl group, an amino group substituted with a substituted or unsubstituted $C_5$-$C_{60}$ aryl group, a substituted or unsubstituted $C_3$-$C_{60}$ heteroaryl group, or a substituted or unsubstituted $C_6$-$C_{60}$ condensed polycyclic group.

20. A flat panel display device comprising the organic light-emitting device of claim 8, wherein the first electrode of the organic light-emitting device is electrically connected to a source electrode or a drain electrode of a thin-film transistor.

* * * * *